(12) United States Patent
Brasso et al.

(10) Patent No.: US 11,286,512 B2
(45) Date of Patent: Mar. 29, 2022

(54) COMPOSITIONS, METHODS, SYSTEMS AND/OR KITS FOR DETECTING ANTIMICROBIAL RESISTANCE IN BACTERIA

(71) Applicant: BECTON, DICKINSON AND COMPANY, Franklin Lakes, NJ (US)

(72) Inventors: William B. Brasso, Columbia, MD (US); David J. Turner, York, PA (US); Susan M. Kircher, Hanover, PA (US); Fatimah Alrashidi-Brooks, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 214 days.

(21) Appl. No.: 16/313,846

(22) PCT Filed: Jun. 26, 2017

(86) PCT No.: PCT/US2017/039305
§ 371 (c)(1),
(2) Date: Dec. 27, 2018

(87) PCT Pub. No.: WO2018/005370
PCT Pub. Date: Jan. 4, 2018

(65) Prior Publication Data
US 2019/0153503 A1 May 23, 2019

Related U.S. Application Data

(60) Provisional application No. 62/466,987, filed on Mar. 3, 2017, provisional application No. 62/443,590, filed on (Continued)

(51) Int. Cl.
*C12Q 1/18* (2006.01)
*C12Q 1/10* (2006.01)
*C12Q 1/34* (2006.01)

(52) U.S. Cl.
CPC .......... *C12Q 1/18* (2013.01); *C12Q 1/10* (2013.01); *C12Q 1/34* (2013.01); *G01N 2333/986* (2013.01)

(58) Field of Classification Search
None
See application file for complete search history.

(56) References Cited

U.S. PATENT DOCUMENTS

| 5,922,593 | A | 7/1999 | Livingston |
| 6,096,272 | A | 8/2000 | Clark et al. |
| (Continued) | | | |

FOREIGN PATENT DOCUMENTS

| CN | 103443288 A | 12/2013 |
| JP | 2001-500057 A | 1/2001 |
| (Continued) | | |

OTHER PUBLICATIONS

Maurer et al., J. Clin. Microbiol 53(1): 95-104 (2015).*
(Continued)

*Primary Examiner* — Erin M. Bowers
(74) *Attorney, Agent, or Firm* — Knobbe, Martens, Olson & Bear LLP

(57) ABSTRACT

Provided herein are compositions, methods, systems and/or kits for detection of bacteria expressing enzymes that confer resistance to antimicrobial agents. Certain embodiments of the compositions, methods, systems and/or kits of the present disclosure are related to detection of carbapenemase-producing gram negative bacteria. Certain embodiments of the compositions, methods, systems and/or kits of the present disclosure are related to detection of Ambler Class A, B and/or D carbapenemase-producing enteric and non-fermenting gram negative rod bacteria.

14 Claims, 39 Drawing Sheets

Related U.S. Application Data on Jan. 6, 2017, provisional application No. 62/355,169, filed on Jun. 27, 2016.

(56) References Cited

U.S. PATENT DOCUMENTS

| | | | |
|---|---|---|---|
| 6,110,856 | A | 8/2000 | Flick et al. |
| 6,372,485 | B1 | 4/2002 | Clark et al. |
| 7,115,384 | B2 | 10/2006 | Clark et al. |
| 9,304,141 | B2 | 4/2016 | Berndt |
| 2009/0142796 | A1 | 6/2009 | Yu et al. |
| 2013/0330756 | A1 | 12/2013 | Ghirardi et al. |
| 2014/0134656 | A1 | 5/2014 | Dortet et al. |
| 2014/0308693 | A1 | 10/2014 | Nordmann et al. |
| 2015/0160211 | A1* | 6/2015 | Devigne .......... G01N 33/56911 435/7.72 |
| 2016/0102334 | A1 | 4/2016 | Jung et al. |

FOREIGN PATENT DOCUMENTS

| | | |
|---|---|---|
| JP | 2014-519833 A | 8/2014 |
| JP | 2014-533951 A | 12/2014 |
| JP | 2016-010399 A | 1/2016 |
| WO | WO 2013/004779 A1 | 1/2013 |

OTHER PUBLICATIONS

Rosco Diagnostica, Kits for β-lactamase identification—insert for KPC/MBL in P. aeruginosa/Acinetobacter kit, version 2, Apr. 20, 2016.*

Birgy et al., Phenotypic screening of carbapenemases and associated β-lactamases in carbapenem-resistant Enterobacteriaceae.J Clin Microbiol. (2012) 50(4):1295-1302.

Hrabák et al., Detection of carbapenemases in Enterobacteriaceae: a challenge for diagnostic microbiological laboratories. Clin Microbiol Infect. (2014) 20(9):839-853.

Hartl et al., Temocillin and meropenem to discriminate resistance mechanisms leading to decreased carbapenem susceptibility with focus on OXA-48 in Enterobacteriaceae. Clin Microbiol Infect. (2013) 19(5):E230-232.

Jeong et al., Broth microdilution methods using β-lactamase inhibitors for the identification of *Klebsiella pneumoniae* carbapenemases and metallo-β-lactamases in Gram-negative bacilli. Ann Clin Lab Sci. (2014) 44(1):49-55.

ROSCO Diagnostica, Kits for beta-lactamase identification—Insert for KPC/Metallo-ß-Lactamase Confirm Kit; Feb. 4, 2013, in 4 pages.

ROSCO Diagnostica, Kits for beta-lactamase identification—Insert for KPC/MBL in P. aeruginosa/cinetobacter Kit, Version 2; Apr. 20, 2016, in 4 pages.

Hammoudi, D., et al., How to Detect Carbapenemase Producers? A literature Review of Phenotypic and Molecular Methods, Journal of Microbiological Methods, vol. 107, pp. 106-118, 2014.

International Search Report and Written Opinion, dated Sep. 25, 2017, in International Application No. PCT/US2017/039305.

Nordmann, P., et al., Identification and Screening of Carbapenemase-Producing Enterobacterlaceae, Clinical Microbiology and Infection, vol. 18, pp. 432-438, 2012.

Woodford, N., et al., In vitro activity of temocillin against multidrug-resistant clinical isolates of *Escherichia coli*, *Klebsiella* spp. and *Enterobacter* spp., and evaluation of high-level temocillin resistance as a diagnostic marker for OXA-48 carbapenemase, Journal of Antimicrobial Chemotherapy, pp. 564-567, 2014.

Stuart J.C., et al., Guideline for Phenotypic Screening and Confirmation if Carbapenemases in Enterobacteriaceae, International Journal of Antimicrobial Agents, vol. 36, No. 3, pp. 205-210, 2010.

Extended European Search Report, dated Jan. 31, 2020, in European Application No. EP 17821016.7.

Yoshikazu I., About early (rapid) detection. Animus (2011) 69(4): 11-18.

Japanese Office Action for Application No. 2018-567784, filed Dec. 26, 2018.

* cited by examiner

COMPOSITIONS, METHODS, SYSTEMS AND/OR KITS FOR DETECTING ANTIMICROBIAL RESISTANCE IN BACTERIA

BACKGROUND

Field

The present disclosure is generally related to detection tests comprising compositions, methods, systems and/or kits for detection of bacteria with enzymes that confer resistance to drugs. Certain embodiments of the present disclosure are related to detection tests comprising compositions, methods, systems and/or kits for the detection and/or identification of carbapenemase-producing gram negative bacteria.

Description of the Related Art

Carbapenemase-producing gram-negative bacteria represent a major and critical threat to public health worldwide because there are few choices available as next-in-line antibiotics to use against these pathogens. While pharmaceutical companies are now targeting a number of new antibiotics in their pipelines, none possess coverage over all of the carbapenemase enzyme types (classes) that can be acquired by these bacteria.

Accurate detection of carbapenemase production, and differentiation of the β-lactamase class, is critical for determination of antimicrobial therapy, epidemiology and infection control measures.

SUMMARY

An embodiment includes a method for determining the presence of none, one or more Ambler class carbapenemases expressed by enteric bacteria, the method comprising: providing a sample comprising the enteric bacteria, applying the enteric bacteria in the test sample to a plurality of at least four test compositions for a duration of time, wherein each of the plurality of at least four test compositions comprises a growth medium and an antibiotic, and at least one of the at least four test compositions further comprises at least one carbapenemase inhibitor, and determining the presence of none, one or more Ambler class carbapenemases expressed by the enteric bacteria by detecting a presence or an inhibition of growth of the enteric bacteria in each of the plurality of at least four test compositions after the duration of time. In any of the embodiments disclosed herein, the antibiotic and carbapenamase inhibitor in at least one test composition comprises, consists of, or consists essentially of, a first concentration of TEM, and a carbapenemase inhibitor of ambler class B. In any of the embodiments disclosed herein, the antibiotic and carbapenamase inhibitor in at least one test composition comprises, consists of, or consists essentially of, a first concentration of DOR, a carbapenemase inhibitor of ambler class C, and a carbapenemase inhibitor of ambler class B. In any of the embodiments disclosed herein, the antibiotic and carbapenamase inhibitor in at least one test composition comprises, consists of, or consists essentially of, a first concentration of MEM, a carbapenemase inhibitor of ambler class C, and a carbapenemase inhibitor of ambler A. In any of the embodiments disclosed herein, the antibiotic in at least one test composition comprises, consists of, or consists essentially of, a second concentration of DOR. In any of the embodiments disclosed herein, the method can include determining the one or more Ambler class carbapenemases expressed by enteric bacteria is Class D by detecting: the presence of growth in a first test composition, wherein the antibiotic and inhibitor comprise, consist of, or consist essentially of, a first concentration of TEM and a carbapenemase inhibitor of ambler class B. In any of the embodiments disclosed herein, the method can include determining the one or more Ambler class carbapenemases expressed by enteric bacteria is Class A by detecting: the inhibition of growth in the first test composition, wherein the antibiotic and inhibitor comprise, consist of, or consist essentially of, a first concentration of TEM, and a carbapenemase inhibitor of ambler class B, the presence of growth in a second test composition, wherein the antibiotic and inhibitors comprise, consist of, or consist essentially of, a first concentration of DOR, a carbapenemase inhibitor of ambler class C, and a carbapenemase inhibitor of ambler class B, and the inhibition of growth in a third test composition, wherein the antibiotic and inhibitors comprise, consist of, or consist essentially of, a first concentration of MEM, a carbapenemase inhibitor of ambler class C, and a carbapenemase inhibitor of ambler class A. In any of the embodiments disclosed herein, the method can include determining the one or more Ambler class carbapenemases expressed by enteric bacteria is Class B by detecting: the inhibition of growth in the first test composition, wherein the antibiotic and inhibitors comprise, consist of, or consist essentially of, a first concentration of TEM as the antibiotic and further comprising a carbapenemase inhibitor of ambler class B, the inhibition of growth in the second test composition, wherein the antibiotic and inhibitors comprise, consist of, or consist essentially of, a first concentration of DOR, a carbapenemase inhibitor of ambler class C, and a carbapenemase inhibitor of ambler class B, and the presence of growth in a fourth test composition, wherein the antibiotic comprises, consists of, or consists essentially of, a second concentration of DOR. In any of the embodiments disclosed herein, the method can include determining the one or more Ambler class carbapenemases expressed by enteric bacteria is Class D by detecting: the inhibition of growth in the first test composition, wherein the antibiotic and inhibitor comprise, consist of, or consist essentially of, a first concentration of TEM, and a carbapenemase inhibitor of ambler class B, the inhibition of growth in the second test composition, wherein the antibiotic and inhibitors comprise, consist of, or consist essentially of, a first concentration of DOR, a carbapenemase inhibitor of ambler class C, and a carbapenemase inhibitor of ambler class B, and the inhibition of growth in the fourth test composition, wherein the antibiotic comprises, consists of, or consists essentially of, a second concentration of DOR. In any of the embodiments disclosed herein, the method can include determining the presence of one or more Ambler class carbapenemases expressed by enteric bacteria, wherein the Ambler class is not identified, by detecting: the inhibition of growth in the first test composition, wherein the antibiotic and inhibitor comprise, consist of, or consist essentially of, a first concentration of TEM, and a carbapenemase inhibitor of ambler class B, the presence of growth in the second test composition, wherein the antibiotic and inhibitors comprise, consist of, or consist essentially of, a first concentration of DOR, a carbapenemase inhibitor of ambler class C, and a carbapenemase inhibitor of ambler class B, and the presence of growth in the third test composition of the plurality of at least four test compositions, wherein the antibiotic and inhibitors comprise, consist of, or consist essentially of, a first concentration of MEM as the antibiotic and further comprising a carbapenemase inhibitor of ambler class C and a carbapenemase inhibitor of ambler class A. In any of the embodiments disclosed herein, the method can include determining the presence of one or more Ambler class A, B or D carbapenemases expressed by enteric bacteria by detecting: the inhibition of growth in the first test composition, wherein the antibiotic and inhibitor comprise, consist of, or consist essentially of, a first concentration of TEM, a carbapenemase inhibitor of ambler class B, the presence of growth in the second test composition, wherein the antibiotic and inhibitors comprise, consist of, or consist essentially of, a first concentration of, comprising DOR, a carbapenemase inhibitor of ambler class C, and a carbapenemase inhibitor of ambler class B, and the presence of growth in the third test composition, wherein the antibiotic and inhibitors comprise, consist of, or consist essentially of, a first concentration of MEM, a carbapenemase inhibitor of ambler class C, and a carbapenemase inhibitor of ambler class A. In any of the embodiments disclosed herein, the antibiotic and carbapenamase inhibitor in at least one test composition comprises, consists of, or consists essentially of, a third concentration of MEM, and a carbapenemase inhibitor of ambler class C. In any of the embodiments disclosed herein, the method can include determining that no answer is obtained regarding identifying the one or more Ambler class carbapenemases expressed by enteric bacteria by detecting: the inhibition of growth in a first test composition, wherein the antibiotic and inhibitor comprise, consist of, or consist essentially of, a first concentration of TEM, and a carbapenemase inhibitor of ambler class B, the presence of growth in a second test composition, wherein the antibiotic and inhibitors comprise, consist of, or consist essentially of, a first concentration of DOR, a carbapenemase inhibitor of ambler class C, and a carbapenemase inhibitor of ambler class B, the presence of growth in a third test composition of the plurality of at least four test compositions wherein the antibiotic and inhibitors comprise, consist of, or consist essentially of, a first concentration of MEM, a carbapenemase inhibitor of ambler class C, and a carbapenemase inhibitor of ambler class A, and the inhibition of growth in a fifth test composition, wherein the antibiotic and inhibitor comprise, consist of, or consist essentially of, a third concentration of MEM, and a carbapenemase inhibitor of ambler class C. In any of the embodiments disclosed herein, the method can include determining the presence of one or more Ambler class A, B or D carbapenemases expressed by enteric bacteria by detecting: the inhibition of growth in the first test composition, wherein the antibiotic and inhibitor comprise, consist of, or consist essentially of, a first concentration of TEM, and a carbapenemase inhibitor of ambler class B, the presence of growth in the second test composition, wherein the antibiotic and inhibitors comprise, consist of, or consist essentially of, a first concentration of DOR, a carbapenemase inhibitor of ambler class C, and a carbapenemase inhibitor of ambler class B, the presence of growth in the third test composition, wherein the antibiotic and inhibitors comprise, consist of, or consist essentially of, a first concentration of MEM, a carbapenemase inhibitor of ambler class C, and a carbapenemase inhibitor of ambler class A, and the presence of growth in the fifth test composition, wherein the antibiotic and inhibitor comprise, consist of, or consist essentially of, the third concentration of MEM, and a carbapenemase inhibitor of ambler class C.

An embodiment includes a method for determining the presence of none, one or more Ambler class carbapenemases expressed by enteric bacteria, the method comprising: providing a sample comprising the enteric bacteria, applying the enteric bacteria in the test sample to a plurality of at least four test compositions for a duration of time, wherein each of the plurality of at least four test compositions comprises a growth medium and an antibiotic, and at least one of the at least four test compositions further comprises at least one carbapenemase inhibitor, and determining the presence of none, one or more Ambler class carbapenemases expressed by the enteric bacteria by detecting a presence or an inhibition of growth of the enteric bacteria in each of the plurality of at least four test compositions after the duration of time. In any of the embodiments disclosed herein, the antibiotic and carbapenamase inhibitor in at least one test composition comprises, consists of, or consists essentially of, a first concentration of MEM, a carbapenemase inhibitor of ambler class C, and a carbapenemase inhibitor of ambler class B. In any of the embodiments disclosed herein, the antibiotic and carbapenamase inhibitor in at least one test composition comprises, consists of, or consists essentially of, a first concentration of MEM, a carbapenemase inhibitor of ambler class C, and a carbapenemase inhibitor of ambler A. In any of the embodiments disclosed herein, the antibiotic and carbapenamase inhibitor in at least one test composition comprises, consists of, or consists essentially of, a first concentration of DOR, a carbapenemase inhibitor of ambler class C, and a carbapenemase inhibitor of ambler class D. In any of the embodiments disclosed herein, the antibiotic and carbapenamase inhibitor in at least one test composition comprises, consists of, or consists essentially of, a second concentration of MEM, a carbapenemase inhibitor of ambler class C, and a carbapenemase inhibitor of ambler A. In any of the embodiments disclosed herein, the method can include determining the one or more Ambler class carbapenemases expressed by enteric bacteria is Class A by detecting: the inhibition of growth in a first test composition, wherein the antibiotic and inhibitors comprise, consist of, or consist essentially of, a first concentration of MEM, a carbapenemase inhibitor of ambler class B, and a carbapenemase inhibitor of ambler class C, and the inhibition of growth in a second test composition, wherein the antibiotic and inhibitors comprise, consist of, or consist essentially of, a second concentration of MEM, a carbapenemase inhibitor of ambler class C, and a carbapenemase inhibitor of ambler class A. In any of the embodiments disclosed herein, the method can include determining the one or more Ambler class carbapenemases expressed by enteric bacteria is Class B by detecting: the inhibition of growth in the first test composition, wherein the antibiotic and inhibitors comprise, consist of, or consist essentially of, a first concentration of MEM, a carbapenemase inhibitor of ambler class B, and a carbapenemase inhibitor of ambler class C, the presence of growth in the second test composition, wherein the antibiotic and inhibitors comprise, consist of, or consist essentially of, a second concentration of MEM, a carbapenemase inhibitor of ambler class C, and a carbapenemase inhibitor of ambler class A. In any of the embodiments disclosed herein, the method can include determining the one or more Ambler class carbapenemases expressed by enteric bacteria is Class A by detecting: the presence of growth in the first test composition, wherein the antibiotic and inhibitors comprise, consist of, or consist essentially of, a first concentration of MEM, a carbapenemase inhibitor of ambler class B, and a carbapenemase inhibitor of ambler class C, and by detecting the inhibition of growth in a third test composition, wherein the antibiotic and inhibitors comprise, consist of, or consist essentially of, a first concentration of MEM, a carbapenemase inhibitor of ambler class C, and a carbapenemase inhibitor of ambler class A. In any of the embodiments disclosed herein, the method can include determining the one or more Ambler class carbapenemases expressed by enteric bacteria is Class D by detecting: the presence of growth in the first test composition, wherein the antibiotic and inhibitors comprise, consist of, or consist essentially of, a first concentration of MEM, a carbapenemase inhibitor of ambler class B, and a carbapenemase inhibitor of ambler class C, the presence of growth in the third test composition, wherein the antibiotic and inhibitors comprise, consist of, or consist essentially of, a first concentration of MEM, a carbapenemase inhibitor of ambler class C, and a carbapenemase inhibitor of ambler class A, and the inhibition of growth in a fourth test composition, wherein the antibiotic and inhibitors comprise, consist of, or consist essentially of, a first concentration of DOR, a carbapenemase inhibitor of ambler class C, and a carbapenemase inhibitor of ambler class D. In any of the embodiments disclosed herein, the method can include determining the presence of one or more Ambler class A, B or D carbapenemases expressed by enteric bacteria by detecting: the presence of growth in the first test composition, wherein the antibiotic and inhibitors comprise, consist of, or consist essentially of, a first concentration of MEM, a carbapenemase inhibitor of ambler class B, and a carbapenemase inhibitor of ambler class C, the presence of growth in the third test composition, wherein the antibiotic and inhibitors comprise, consist of, or consist essentially of, a first concentration of MEM, a carbapenemase inhibitor of ambler class C, and a carbapenemase inhibitor of ambler class A, and the presence of growth in the fourth test composition, wherein the antibiotic and inhibitors comprise, consist of, or consist essentially of, a first concentration of DOR, a carbapenemase inhibitor of ambler class C, and a carbapenemase inhibitor of ambler class D. In any of the embodiments disclosed herein, the method can include determining that no answer is obtained regarding identifying the one or more Ambler class carbapenemases expressed by enteric bacteria by detecting: the presence of growth in the first test composition, wherein the antibiotic and inhibitors comprise, consist of, or consist essentially of, a first concentration of MEM, a carbapenemase inhibitor of ambler class B, and a carbapenemase inhibitor of ambler class C, the presence of growth in the third test composition, wherein the antibiotic and inhibitors comprise, consist of, or consist essentially of, a first concentration of MEM, a carbapenemase inhibitor of ambler class C, and a carbapenemase inhibitor of ambler class A, and the presence of growth in the fourth test composition, wherein the antibiotic and inhibitors comprise, consist of, or consist essentially of, a first concentration of DOR, a carbapenemase inhibitor of ambler class C, and a carbapenemase inhibitor of ambler class D.

In any of the embodiments disclosed herein, the method can include applying the enteric bacteria in the test sample to a plurality of at least five test compositions for a duration of time, wherein the antibiotic and carbapenamase inhibitor in at least one test composition comprises, consists of, or consists essentially of, a first concentration of MEM and a carbapenemase inhibitor of ambler class C. In any of the embodiments disclosed herein, the method can include determining the presence of one or more Ambler class A, B or D carbapenemases expressed by enteric bacteria by detecting: the presence of growth in a first test composition, wherein the antibiotic and inhibitor comprise, consist of, or consist essentially of, a first concentration of MEM and a carbapenemase inhibitor of ambler class C. In any of the embodiments disclosed herein, the method can include determining the absence of one or more Ambler class A, B or D carbapenemases expressed by enteric bacteria by detecting: the inhibition of growth in a first test composition, wherein the antibiotic and inhibitor comprise, consist of, or consist essentially of, a first concentration of MEM and a carbapenemase inhibitor of ambler class C. In any of the embodiments disclosed herein, the method can include a method for identifying none, one or more Ambler class carbapenemases expressed by non-fermenting bacteria, the method comprising: providing a sample comprising the non-fermenting bacteria, applying the non-fermenting bacteria in the test sample to a composition for a duration of time, wherein the test composition comprises a growth medium and an antibiotic and a carbapenemase inhibitor, and determining the presence of none, one or more Ambler class carbapenemases expressed by non-fermenting bacteria by detecting a presence or an inhibition of growth of the non-fermenting bacteria in the test compositions after the duration of time. In any of the embodiments disclosed herein, the antibiotic and carbapenamase inhibitor in at least one test composition comprises, consists of, or consists essentially of, a third concentration of DOR and a carbapenemase inhibitor of ambler class C. In any of the embodiments disclosed herein, the method can include determining the presence of one or more Ambler class A, B or D carbapenemases expressed by non-fermenting bacteria by detecting: the presence of growth in a test composition, wherein the antibiotic and inhibitor comprise, consist of, or consist essentially of, a third concentration of DOR, and a carbapenemase inhibitor of ambler class C. In any of the embodiments disclosed herein, the method can include determining the absence of one or more Ambler class A, B or D carbapenemases expressed by non-fermenting bacteria by detecting: the inhibition of growth in a test composition, wherein the antibiotic and inhibitor comprise, consist of, or consist essentially of, a third concentration of DOR, and a carbapenemase inhibitor of ambler class C.

In any of the embodiments disclosed herein, the method can further include a method for determining the presence of none, one, or more Ambler class carbapenemases expressed by non-fermenting bacteria, the method comprising: providing a sample comprising the non-fermenting bacteria, applying the non-fermenting bacteria in the test sample to a plurality of at least three test compositions for a duration of time, wherein each of the plurality of at least three test compositions comprises a growth medium and an antibiotic, and at least one of the at least three test compositions further comprises at least one carbapenemase inhibitor, and determining the presence of none, one, or more one or more Ambler class carbapenemases expressed by the non-fermenting bacteria by detecting a presence or an inhibition of growth of the non-fermenting bacteria in each of the plurality of at least three test compositions after the duration of time.

An embodiment includes a method for determining the presence of none, one, or more Ambler class carbapenemases expressed by non-fermenting bacteria, the method comprising: providing a sample comprising the non-fermenting bacteria, applying the non-fermenting bacteria in the test sample to a plurality of at least three test compositions for a duration of time, wherein each of the plurality of at least three test compositions comprises a growth medium and an antibiotic, and at least one of the at least three test compositions further comprises at least one carbapenemase inhibitor, and determining the presence of none, one, or more one or more Ambler class carbapenemases expressed by the non-fermenting bacteria by detecting a presence or an inhibition of growth of the non-fermenting bacteria in each of the plurality of at least three test compositions after the duration of time. In any of the embodiments disclosed herein, the antibiotic and carbapenamase inhibitor in at least one test composition comprises, consists of, or consists essentially of, a third concentration of DOR, a carbapenemase inhibitor of ambler class C, and a carbapenemase inhibitor of ambler class B. In any of the embodiments disclosed herein, the antibiotic and carbapenamase inhibitor in at least one test composition comprises, consists of, or consists essentially of, a fourth concentration of MEM, a carbapenemase inhibitor of ambler class C, and a carbapenemase inhibitor of ambler class D. In any of the embodiments disclosed herein, the antibiotic and carbapenamase inhibitor in at least one test composition comprises, consists of, or consists essentially of, a fifth concentration of DOR, and a carbapenemase inhibitor of ambler class C, and a carbapenemase inhibitor of ambler class D. In any of the embodiments disclosed herein, the method can include determining the one or more Ambler class carbapenemases expressed by non-fermenting bacteria as Class B by detecting: the inhibition of growth in a first test composition, wherein the antibiotic and inhibitor comprise, consist of, or consist essentially of, a third concentration of DOR, a carbapenemase inhibitor of ambler class C, and a carbapenemase inhibitor of ambler class B. In any of the embodiments disclosed herein, the method can include determining the one or more Ambler class carbapenemases expressed by non-fermenting bacteria as Class D by detecting: the presence of growth in the first test composition, wherein the antibiotic and inhibitor comprise, consist of, or consist essentially of, a third concentration of DOR, a carbapenemase inhibitor of ambler class C, and a carbapenemase inhibitor of ambler class B, and the inhibition of growth in a second test composition, wherein the antibiotic and inhibitor comprise, consist of, or consist essentially of, a fourth concentration of MEM, a carbapenemase inhibitor of ambler class C, and a carbapenemase inhibitor of ambler class D. In any of the embodiments disclosed herein, the method can include determining the one or more Ambler class carbapenemases expressed by non-fermenting bacteria as Class A by detecting: the presence of growth in the first test composition, wherein the antibiotic and inhibitor comprise, consist of, or consist essentially of, a third concentration of DOR, a carbapenemase inhibitor of ambler class C, and a carbapenemase inhibitor of ambler class B, the presence of growth in the second test composition, wherein the antibiotic and inhibitor comprise, consist of, or consist essentially of, a fourth concentration of MEM, a carbapenemase inhibitor of ambler class C, and a carbapenemase inhibitor of ambler class D, and the inhibition of growth in an third test composition, wherein the antibiotic and inhibitor comprise, consist of, or consist essentially of, a fifth concentration of DOR, a carbapenemase inhibitor of ambler class C, and a carbapenemase inhibitor of ambler class D. In any of the embodiments disclosed herein, the method can include determining the presence of one or more Ambler class A, B or D carbapenemases expressed by non-fermenting bacteria by detecting: the presence of growth in the first test composition, wherein the antibiotic and inhibitor comprise, consist of, or consist essentially of, a third concentration of DOR, a carbapenemase inhibitor of ambler class C, and a carbapenemase inhibitor of ambler class B, the presence of growth in the second test composition, wherein the antibiotic and inhibitor comprise, consist of, or consist essentially of, a fourth concentration of MEM, a carbapenemase inhibitor of ambler class C, and a carbapenemase inhibitor of ambler class D, and the presence of growth in the third test composition, wherein the antibiotic and inhibitor comprise, consist of, or consist essentially of, a fifth concentration of DOR, a carbapenemase inhibitor of ambler class C, and a carbapenemase inhibitor of ambler class D. In any of the embodiments disclosed herein, the antibiotic and carbapenamase inhibitor in at least one test composition comprises, consists of, or consists essentially of, a third concentration of DOR, a carbapenemase inhibitor of ambler class C, and a carbapenemase inhibitor of ambler class B. In any of the embodiments disclosed herein, the antibiotic and carbapenamase inhibitor in at least one test composition comprises, consists of, or consists essentially of, a fourth concentration of MEM, a carbapenemase inhibitor of ambler class C, and a carbapenemase inhibitor of ambler class D. In any of the embodiments disclosed herein, the antibiotic and carbapenamase inhibitor in at least one test composition comprises, consists of, or consists essentially of, a fourth concentration of DOR, and a carbapenemase inhibitor of ambler class C. In any of the embodiments disclosed herein, the method can include determining the one or more Ambler class carbapenemases expressed by non-fermenting bacteria is either Class A, B, or D by detecting: the presence of growth in a first test composition, wherein the antibiotic and inhibitor comprise, consist of, or consist essentially of, a third concentration of DOR, a carbapenemase inhibitor of ambler class C, and a carbapenemase inhibitor of ambler class B, and the presence of growth in a second test composition, wherein the antibiotic and inhibitor comprise, consist of, or consist essentially of, a fourth concentration of MEM, a carbapenemase inhibitor of ambler class C, and a carbapenemase inhibitor of ambler class D. In any of the embodiments disclosed herein, the method can include determining the one or more Ambler class carbapenemases expressed by non-fermenting bacteria is Class D by detecting: the presence of growth in a first test composition, wherein the antibiotic and inhibitor comprise, consist of, or consist essentially of, a third concentration of DOR, a carbapenemase inhibitor of ambler class C, and a carbapenemase inhibitor of ambler class B, and the inhibition of growth in a second test composition, wherein the antibiotic and inhibitor comprise, consist of, or consist essentially of, a fourth concentration of MEM, a carbapenemase inhibitor of ambler class C, and a carbapenemase inhibitor of ambler class D. In any of the embodiments disclosed herein, the method can include determining the one or more Ambler class carbapenemases expressed by non-fermenting bacteria is Class B by detecting: the inhibition of growth in the first test composition, wherein the antibiotic and inhibitor comprise, consist of, or consist essentially of, a third concentration of DOR, a carbapenemase inhibitor of ambler class C, and a carbapenemase inhibitor of ambler class B, and the presence of growth in a third test composition, wherein the antibiotic and inhibitor comprise, consist of, or consist essentially of, a fourth concentration of DOR, and a carbapenemase inhibitor of ambler class C. In any of the embodiments disclosed herein, the method can include determining that no answer is obtained regarding identifying the one or more Ambler class carbapenemases expressed by non-fermenting bacteria by detecting: the inhibition of growth in the first test composition, wherein the antibiotic and inhibitor comprise, consist of, or consist essentially of, a third concentration of DOR, a carbapenemase inhibitor of ambler class C, and a carbapenemase inhibitor of ambler class B, and the inhibition of growth in the third test composition, wherein the antibiotic and inhibitor comprise, consist of, or consist essentially of, a fourth concentration of DOR, and a carbapenemase inhibitor of ambler class C. In any of the embodiments disclosed herein, the method can include determining the one or more Ambler class carbapenemases expressed by non-fermenting bacteria is either Class A, B, or D by detecting: the inhibition of growth in the first test composition, wherein the antibiotic and inhibitor comprise, consist of, or consist essentially of, a third concentration of DOR, a carbapenemase inhibitor of ambler class C, and a carbapenemase inhibitor of ambler class B, and the inhibition of growth in the third test composition, wherein the antibiotic and inhibitor comprise, consist of, or consist essentially of, a fourth concentration of DOR, and a carbapenemase inhibitor of ambler class C.

In any of the embodiments disclosed herein, the method can include applying the non-fermenting bacteria in the test sample to a plurality of at least four test compositions for a duration of time, wherein the antibiotic and carbapenamase inhibitor in at least one test composition comprises, consists of, or consists essentially of, a fifth concentration of DOR, a carbapenemase inhibitor of ambler class C, and a carbapenemase inhibitor of ambler class D. In any of the embodiments disclosed herein, the method can include determining the one or more Ambler class carbapenemases expressed by non-fermenting bacteria is either Class A, B, or D by detecting: the presence of growth in a first test composition, wherein the antibiotic and inhibitor comprise, consist of, or consist essentially of, a third concentration of DOR, a carbapenemase inhibitor of ambler class C, and a carbapenemase inhibitor of ambler class B, the presence of growth in a second test composition, wherein the antibiotic and inhibitor comprise, consist of, or consist essentially of, a fourth concentration of MEM, a carbapenemase inhibitor of ambler class C, and a carbapenemase inhibitor of ambler class D, and the presence of growth in an fourth test composition, wherein the antibiotic and inhibitor comprise, consist of, or consist essentially of, a fifth concentration of DOR, a carbapenemase inhibitor of ambler class C, and a carbapenemase inhibitor of ambler class D. In any of the embodiments disclosed herein, the method can include determining the one or more Ambler class carbapenemases expressed by non-fermenting bacteria is Class A by detecting: the presence of growth in a first test composition, wherein the antibiotic and inhibitor comprise, consist of, or consist essentially of, a third concentration of DOR, a carbapenemase inhibitor of ambler class C, and a carbapenemase inhibitor of ambler class B, the presence of growth in a second test composition, wherein the antibiotic and inhibitor comprise, consist of, or consist essentially of, a fourth concentration of MEM, a carbapenemase inhibitor of ambler class C, and a carbapenemase inhibitor of ambler class D, and the inhibition of growth in an fourth test composition, wherein the antibiotic and inhibitor comprise, consist of, or consist essentially of, a fifth concentration of DOR, a carbapenemase inhibitor of ambler class C, and a carbapenemase inhibitor of ambler class D.

In any of the embodiments disclosed herein, the method can further include determining whether a bacteria in a sample is enteric, non-fermenting, or both.

In any of the embodiments disclosed herein, the first concentration of TEM is about 6 µg/ml to about 128 µg/ml, about 32 µg/ml to about 128 µg/ml, about 32 µg/ml to about 80 µg/ml, or about 64 µg/ml. In any of the embodiments disclosed herein, the first concentration of DOR is about 0.006 µg/ml to about 0.75 µg/ml, about 0.03125 µg/ml to about 0.1 µg/ml, or about 0.0625 µg/ml or about 0.06 µg/ml. In any of the embodiments disclosed herein, the second concentration of DOR is about 0.0125 µg/ml to about 2 µg/ml, 0.0625 µg/ml to about 0.25 µg/ml, or about 0.125 µg/ml. In any of the embodiments disclosed herein, the third concentration of DOR is about 0.1 µg/ml to about 400 µg/ml, about 0.5 µg/ml to about 3 µg/ml, or about 1 µg/ml. In any of the embodiments disclosed herein, the fourth concentration of DOR is about 0.2 µg/ml to about 40 µg/ml, about 0.5 µg/ml to about 4 µg/ml, or about 2 µg/ml. In any of the embodiments disclosed herein, the fifth concentration of DOR is about 0.03125 µg/ml to about 80 µg/ml, about 2 µg/ml to about 24 µg/ml, or about 8 µg/ml. In any of the embodiments disclosed herein, the first concentration of MEM is 0.03125 µg/ml to 1 µg/ml, 0.03125 µg/ml to 0.125 µg/ml, 0.015625 µg/ml to 0.125 µg/ml, about 0.006 µg/ml to about 0.60 µg/ml, about 0.015 µg/ml to about 0.24 µg/ml, about 0.03 µg/ml to about 0.25 µg/ml, about 0.03 µg/ml to about 0.2 µg/ml, about 0.0625 µg/ml or about 0.060 µg/ml. In any of the embodiments disclosed herein, the second concentration of MEM is about 0.015625 µg/ml to about 0.125 µg/ml, about 0.003 µg/ml to about 0.3 µg/ml, about 0.0075 µg/ml to about 0.12 µg/ml, about 0.01 µg/ml to about 0.12 µg/ml, or about 0.03 µg/ml. In any of the embodiments disclosed herein, the third concentration of MEM is about 0.0125 µg/ml to about 5 µg/ml, about 0.125 µg/ml to about 1 µg/ml, or about 0.5 µg/ml. In any of the embodiments disclosed herein, the fourth concentration of MEM is about 0.4 µg/ml to about 40 µg/ml, about 1 µg/ml to about 16 µg/ml, about 2 µg/ml to about 8 µg/ml, or about 4 µg/ml.

In any of the embodiments disclosed herein, the carbapenemase inhibitor of ambler class D comprises a compound selected from the group consisting AVI, Clavulanic acid, boronic acid, tazobactam, sulbactam, vaborbactam (RPX-7009) and BLI-489. In any of the embodiments disclosed herein, the carbapenemase inhibitor of ambler class B is a metal chelator. In any of the embodiments disclosed herein, the carbapenemase inhibitor of ambler class B comprises a compound selected from the group consisting EDTA, DPA and deferoxamine. In any of the embodiments disclosed herein, the carbapenemase inhibitor of ambler class C comprises a compound selected from the group consisting CLOX, dicloxacillin and flucloxacillin. In any of the embodiments disclosed herein, the carbapenemase inhibitor of ambler class A comprises a compound selected from the group consisting of vaborbactam (RPX-7009), AVI, Clavulanic acid, boronic acid, tazobactam, sulbactam, and BLI-489. In any of the embodiments disclosed herein, the carbapenemase inhibitor of ambler class D comprises a compound selected from the group consisting BLI, AVI, Clavulanic acid, boronic acid, tazobactam, sulbactam, vaborbactam and (RPX-7009).

In any of the embodiments disclosed herein, the carbapenemase inhibitor of ambler class B in combination with the first concentration of TEM and/or the first concentration of DOR comprises, consists of, or consists essentially of, EDTA. In any of the embodiments disclosed herein, the carbapenemase inhibitor of ambler class C comprises, consists of, or consists essentially of, CLOX. In any of the embodiments disclosed herein, the carbapenemase inhibitor of ambler class A in combination with the first and/or second concentration of MEM comprises, consists of, or consists essentially of, RPX. In any of the embodiments disclosed herein, the carbapenemase inhibitor of ambler class B in combination with the first concentration of MEM and/or the third concentration of DOR comprises, consists of, or consists essentially of, DPA. In any of the embodiments disclosed herein, the carbapenemase inhibitor of ambler class D in combination with the first and/or fifth concentration of DOR comprises, consists of, or consists essentially of, AVI. In any of the embodiments disclosed herein, the carbapenemase inhibitor of ambler class D in combination with the fourth concentration of MEM comprises, consists of, or consists essentially of, a first concentration of BLI. In any of the embodiments disclosed herein, the concentration of EDTA is about 0.025 mg/ml to about 10 mg/ml, about 0.05 mg/ml to about 1.25 mg/ml, or about 0.25 mg/ml. In any of the embodiments disclosed herein, the concentration of CLOX is about 0.0025 mg/ml to about 40 mg/ml, about 0.020 mg/ml to about 0.5 mg/ml, or about 0.1 mg/ml. In any of the embodiments disclosed herein, the concentration of RPX is about 0.2 µg/ml to about 320 µg/ml, about 1.5 µg/ml to about 40 µg/ml, or about 8 µg/ml. In any of the embodiments disclosed herein, the concentration of DPA is about 0.018 mg/ml to about 1.8 mg/ml, about 0.07 mg/ml to about 0.73 mg/ml, or about 0.178 mg/ml. In any of the embodiments disclosed herein, the concentration of AVI is about 0.1 µg/ml to about 40 µg/ml, about 0.5 µg/ml to about 20 µg/ml, or about 4 µg/ml. In any of the embodiments disclosed herein, the concentration of BLI is about 0.1 µg/ml to about 200 µg/ml, about 1 µg/ml to about 25 µg/ml, or about 5 µg/ml.

In any of the embodiments disclosed herein, the duration of time for detecting a presence or an inhibition of growth less than about 24 hours, less than about 18 hours, less than about 16, or less than about 14 hours. In any of the embodiments disclosed herein, the duration of time for detecting a presence or an inhibition of growth of enteric bacteria is about 6 hours to about 8 hours. In any of the embodiments disclosed herein, the duration of time for detecting a presence or an inhibition of growth of enteric bacteria is about 7 hours. In any of the embodiments disclosed herein, the duration of time for detecting a presence or an inhibition of growth of non-fermenting bacteria is about 8 hours to about 11 hours. In any of the embodiments disclosed herein, wherein the duration of time for detecting a presence or an inhibition of growth of non-fermenting bacteria is about 10 hours. In any of the embodiments disclosed herein, wherein the enteric bacteria comprises a bacteria selected from the group consisting of *Klebsiella pneumoniae, Escherichia coli*, and *Enterobacter aerogenes*. In any of the embodiments disclosed herein, the non-fermenting bacteria comprises a bacteria selected from the group consisting of *Pseudomonas aeruginosa*, and *Acinetobacter baumanii* complex.

In any of the embodiments disclosed herein, detecting a presence or an inhibition of growth is not performed by imaging a change in cell morphology.

An embodiment includes a system for performing the method of any of the embodiments disclosed herein, the automated system comprising: a plurality of compartments, each of the plurality of the compartments comprising a test composition according to any method of any of the preceding claims, a means for providing a sample comprising an enteric bacteria, a non-fermenting bacteria, or both to the plurality of compartments, an instrument for obtaining a first signal from the plurality of compartments provided with the enteric bacteria, non-fermenting bacteria, or both, an incubator for incubating the plurality of compartments provided with the enteric bacteria, non-fermenting bacteria, or both for a duration of time, an instrument for obtaining a second signal from the plurality of compartments comprising enteric bacteria, non-fermenting bacteria, or both, a detector for detecting a presence or an inhibition of growth in the plurality of compartments provided with the enteric bacteria, non-fermenting bacteria, or both by comparing the first and second signals, a computer for generating a output of results from the detector, and an analyzer for interpreting the output of results. In any of the embodiments disclosed herein, the plurality of compartments comprises a compartment selected from the group consisting of wells, plates, and tubes. In any of the embodiments disclosed herein, the system comprises BD Phoenix panels and/or system.

An embodiment includes a kit for identifying one or more Ambler class carbapenemases expressed by enteric bacteria and/or non-fermenting bacteria, the kit comprising: a substrate or panel with a plurality of compartments, wherein each of the plurality of compartments comprises a test composition according to the method of any of the embodiments disclosed herein. In any of the embodiments disclosed herein, a the substrate comprises at least three, or at least four different test compositions. In any of the embodiments disclosed herein, the kit comprises a second substrate comprising a plurality of compartments, wherein each of the plurality of compartments comprises a test composition according to the method of any of claims 1-90, and wherein the plurality of test compositions in the first substrate differ by at least one test composition from the plurality of test compositions in the second substrate.

In any of the embodiments disclosed herein a plurality of test compositions, wherein the test compositions comprise, consist of, or consist essentially of, test compositions selected from the test compositions disclosed in Boxes 1-14. In any of the embodiments disclosed herein, the test compositions comprise, consist of, or consist essentially of, the test compositions disclosed in Boxes 1-5. In any of the embodiments disclosed herein, the test compositions comprise, consist of, or consist essentially of, the test compositions disclosed in Boxes 1, 6, 7, 3, 8 and 9. In any of the embodiments disclosed herein, the test compositions comprise, consist of, or consist essentially of, the test compositions disclosed in Boxes 10, 11, 12 and 13. In any of the embodiments disclosed herein, the test compositions comprise, consist of, or consist essentially of, the test compositions disclosed in Boxes 10, 11, 12, 13 and 14. In any of the embodiments disclosed herein, the test compositions comprise, consist of, or consist essentially of, the test compositions disclosed in Boxes 1, 6, 7, 3 and 9. In any of the embodiments disclosed herein, the test compositions comprise, consist of, or consist essentially of, the test compositions disclosed in Boxes 1, 6, 7, 9, 3 and 10. In any of the embodiments disclosed herein, the test compositions comprise, consist of, or consist essentially of, the test compositions disclosed in Boxes 1, 6, 7, 3, 9, 10, 11, 12 and 14. In any of the embodiments disclosed herein, the test compositions comprise, consist of, or consist essentially of, the test compositions disclosed in Boxes 1, 10, 11, 12 and 14.

DETAILED DESCRIPTION

Figure 1:
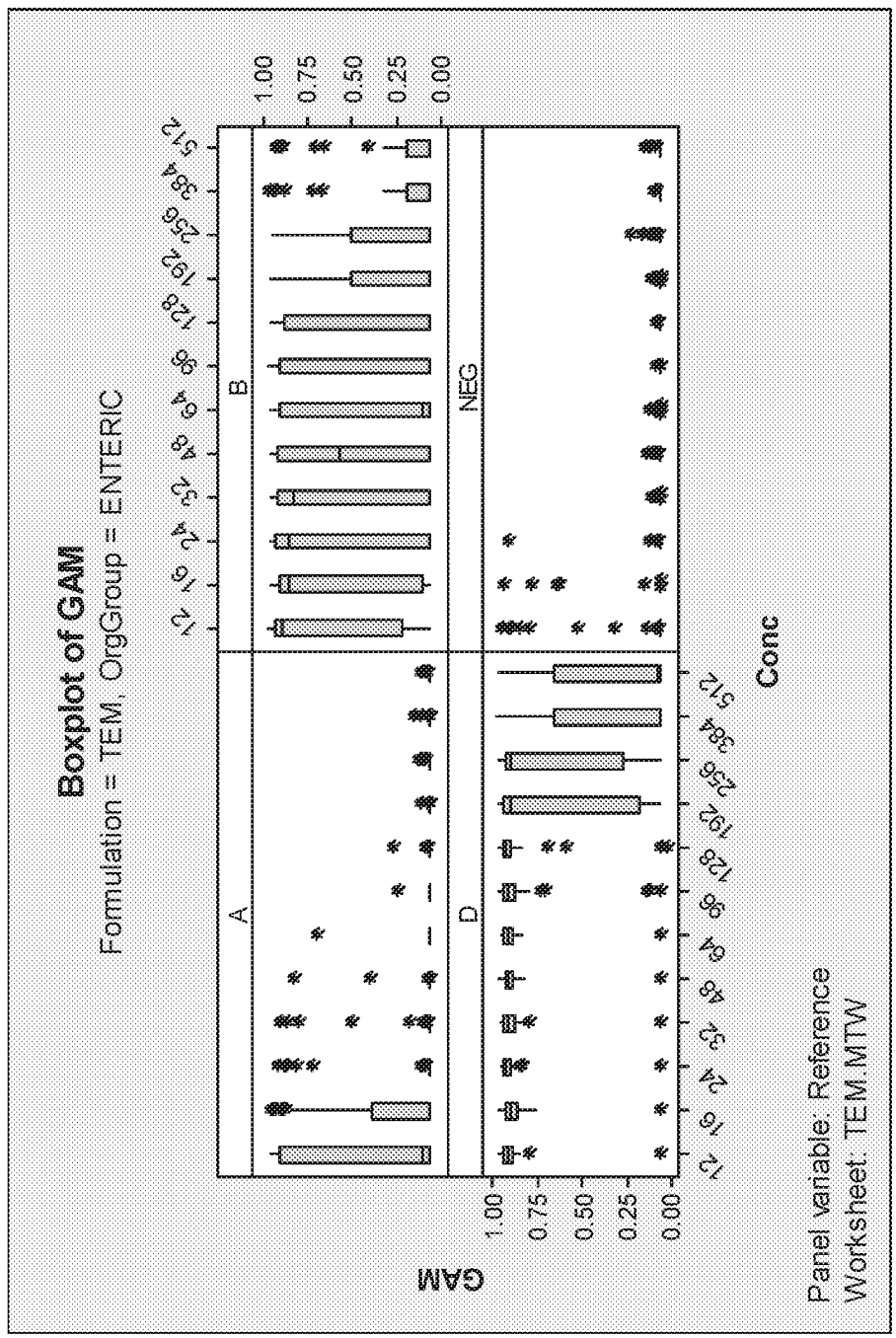
FIG. 1 shows a boxplot of TEM GAM data for enteric bacteria expressing either Class A, Class B or Class D carbapenemase.

Increasing antibiotic resistance and a dwindling antibiotic pipeline have created a global public health crisis in which an increasing number of patients are infected with totally or almost totally antibiotic-resistant gram-negative bacteria. Carbapenemase-producing organisms (CPOs) have become the driving force behind the development of untreatable pathogens which threaten not only treatment of bacterial infections but also the use of antibiotics to protect patients undergoing cancer chemotherapy, transplant surgery, heart surgery, joint replacement surgery and even childbirth.

It is a major challenge for clinical laboratories to rapidly and accurately detect CPOs. Unlike most bacterial infections, optimal therapy of infections by CPOs requires at least two active antibiotics to prevent the emergence and transmission of total antibiotic resistance and death of the patient. That is, physicians may have only a single opportunity to select effective therapy for these infections. It is therefore critical for laboratories to rapidly and accurately detect CPOs to alert physicians of the need for combination therapy.

Most laboratories currently use inaccurate phenotypic carbapenemase detection tests that require overnight incubation. A minority use accurate but inconvenient phenotypic tests or higher priced PCR-based tests that have some unresolved accuracy problems. No current phenotypic test is automated. Therefore, rapid diagnostic tests to advance the detection and control of antimicrobial resistant bacteria are needed.

The currently marketed bioMérieux Rapidec® Carba NP test is a manual stand-alone test, which detects but does not classify carbapenemases. Thus, there is also a therapeutic need to classify carbapenemases into molecular groups.

Disclosed herein are novel detection tests comprising compositions, methods, systems and/or kits for detecting CPOs and further identifying and classifying the Ambler class of carbapenemase enzyme expressed by bacteria. In an embodiment, these novel CPO detection tests have been incorporated into the previously developed BD Phoenix Gram-Negative Identification (ID)/Antimicrobic Susceptibility Test (AST) panel for detecting carbapenemase expressing bacteria. In some embodiments, the detection tests can be applied to all gram-negative bacteria in a sample (e.g., a clinical isolate) and further identifying the Ambler class of carbapenemase in the sample.

In some embodiments, the detection tests incorporate one or more antibiotics and, optionally, one or more inhibitors in a test that allows for a more accurate and rapid identification of one or more Ambler class carbapenemases expressed by bacteria. The one or more antibiotics inhibit the growth of the gram negative bacteria in the sample. However, if the gram negative bacteria are resistant to the one or more antibiotics owing to their expression of one or more Ambler class carbapenemases, one or more inhibitors can be included to allow for a more accurate and rapid identification of the one or more Ambler class carbapenemases expressed by the bacteria. In some embodiments, the identification test comprises exposing the sample to only one antibiotic or combination of antibiotics with/without inhibitor(s). In other embodiments, the test can comprise exposing portions of the sample to multiple different antibiotic(s) with/without inhibitor(s) in multiple wells, such that the sample is tested against more than one antibiotic or combination of antibiotics with/without inhibitor(s) in a test. These multiple combinations are typically run in parallel, such that portions of the sample are exposed to all of the combinations at the same time, with each combination in a separate well, although, it is also possible to run the test by exposing portions of the sample to the various combinations in series. As explained herein, multiple wells comprising a particular antibiotic(s) with/without inhibitor(s) can be run for a given sample (e.g., duplicate, triplicates, etc. of a particular combination of antibiotic and inhibitor).

At least four Ambler Classes of β-lactamases are known, namely Classes A, B, C and D; however, only Class A, B and D are considered carbapenemases Infections by CPOs producing one class of carbapenemase may be susceptible to an antibiotic, whereas infections by CPOs producing another class of carbapenemase may not be susceptible to the same antibiotic. For example, Ambler Class A carbapenemases are candidates for therapy with the new antibiotic ceftazidime/avibactam, while Class B-producing CPOs are intrinsically resistant to this agent, and therefore, patient management will be significantly more effective by distinguishing CPOs that produce Class A and Class B carbapenemases. In short, there is an urgent and unmet need for rapid, accurate and convenient detection and classification of CPOs.

In some embodiments, the detection tests incorporate combinations of one or more antibiotics and one or more inhibitors in a test that allows for a more accurate and rapid identification of Ambler Class A carbapenemase.

In some embodiments, the detection tests incorporate combinations of one or more antibiotics and one or more inhibitors in a test that allows for a more accurate and rapid identification of Ambler Class B carbapenemase.

In some embodiments, the detection tests may incorporate combinations of one or more antibiotics and one or more inhibitors in a test that allows for a more accurate differentiation of Ambler Class C β-lactamases.

In some embodiments, the detection tests incorporate combinations of one or more antibiotics and one or more inhibitors in a test that allows for a more accurate and rapid identification of Ambler Class D carbapenemase. For example, the detection tests incorporate temocillin (TEM), a carboxypenicillin antibiotic, and select inhibitors in a single test that allows for a more accurate and rapid identification of Ambler Class D carbapenemase enzyme.

The various detection tests provided herein can be combined with automated detection systems which utilize one or more algorithms to automate the phenotypic detection of carbapenemase expression by bacteria and optionally Ambler classification of carbapenemase expression by bacteria.

BD Phoenix Panels and Systems

Systems for diagnostic microbiological testing and microorganism identification (ID) and antimicrobial susceptibility determinations (AST) have been described, for example, in patents U.S. Pat. Nos. 5,922,593, 6,096,272, 6,372,485, 7,115,384, 9,304,141 and application publication US 2009/0142796 A1, which are hereby incorporated by in their entireties. These references disclose panels and systems, referred to as the BD Phoenix Gram-negative Identification (ID)/Antimicrobic Susceptibility Test (AST) panels and systems (BD Phoenix panels and systems), for the ID/AST of microorganisms and their susceptibility to one or more antibiotics. The BD Phoenix panels and systems are amenable to a variety of AST determination methods. For example, alamarBlue™, a redox-buffered oxidation-reduction indicator, is added to the AST inoculum fluid and mixed just prior to addition of the microorganism sample to be tested by the instrument. Visible and UV light sources are used to take readings corresponding to red, green, blue, and fluorescent wavelengths of light (For example, see, US 2009/0142796 A1, which is hereby incorporated by in its entirety).

The BD Phoenix panels and systems comprise a substrate with plurality of test wells adapted to receive bacteria suspended in broth and a specific combination of reagents (e.g., antibiotic(s) with/without inhibitor(s)). The bacterial response to the specific combination reagents in the panels is measured by placing the panel instrument systems comprising multiple sources of light (e.g., visible and UV sources) emitting at different wavelengths (e.g., red, green, blue, and fluorescent wavelengths). The instrument systems receive the panels and based on colorimetric and/or fluorometric detection allow for the ID/AST of the microorganisms to be performed (For example, see, US 2009/0142796 A1, which is hereby incorporated by in their entirety). Based on the results of the BD Phoenix panels and systems, the susceptibility of microorganisms (e.g., gram-negative bacteria) to the antibiotics is determined. In addition, the BD Phoenix panels and systems can distinguish between enteric and non-fermenting bacteria.

One of ordinary skill in the art would readily understand the state of the art by a review of the above-mentioned patents and applications. One of ordinary skill in the art would also appreciate the improvements that the novel detection tests comprising compositions, methods, systems and kits disclosed herein provide over the state of the art such as the existing BD Phoenix panels and systems.

BD Phoenix™ CPO Detect (Phoenix™ CPO Detect)

Provided herein is a novel BD Phoenix™ CPO Detect, also known as the Phoenix™ CPO Detect, which comprises detection tests that expand on the BD Phoenix panels and systems by including detection of CPO. The CPO Detect provides rapid, highly sensitive and specific algorithm-based automated detection tests for the detection and identification of bacteria expressing one or more classes of carbapenemases.

The BD Phoenix™ CPO Detect detection tests expand the BD Phoenix panel and system by combining one or more antibiotics, one or more inhibitors of the various classes of carbapenemases, and one or more detection reagents to specifically identify the class of carbapenemase expressed by bacteria.

In order to differentiate whether one or more of Classes A, B and D carbapenemase is expressed by bacteria, one or more antibiotics are used that inhibit the growth in the sample of a gram negative bacteria expressing one or more of Classes A, B and D carbapenemase. In some embodiments, if the gram negative bacteria are resistant to the one or more antibiotic owing to their expression of one or more Ambler class carbapenemases, one or more inhibitors are used to identify the one or more Ambler class carbapenemases. The one or more antibiotics and one or more inhibitors are used in a test, typically comprising sample run in multiple wells with different combinations of antibiotic(s) with/without inhibitor(s) in different wells, for a more accurate and rapid differentiation and identification of the Ambler class of carbapenemase.

In some embodiments, the BD CPO Detect can provide two results: (1) an initial detection-based positive/negative result for carbapenemase detection, (2) a follow-up classification of positive isolates from step (1) according to the molecular class of the carbapenemase. In contrast, the bioMérieux Rapidec® Carba NP test provides only an initial detection-based positive/negative result, this level of analysis is the current standard for marketed phenotypic tests.

As used herein, in the context of the initial detection-based positive/negative result for carbapenemase detection, "sensitivity" of a test or "sensitivity" of detection is defined as the percent of CPOs that were detected in the positive/negative phase of testing.

As used herein, in the context of the initial detection-based positive/negative result for carbapenemase detection, "specificity" of a or test "specificity" of detection is defined as the percent of carbapenemase-negative isolates that were correctly identified as such in the positive/negative phase of testing.

As used herein, in the context of the classification of positive isolates according to the molecular class of the carbapenemase, a classification result is regarded as good if it is either an accurate classification or a positive but untyped result. Detecting a carbapenemase without classifying it is important and highly beneficial for patient management. Accurately classifying the carbapenemase increases the value of the result. If the carbapenemase belongs to Class A, ceftazidime/avibactam is a potential candidate for therapy. Class B carbapenemase detection contraindicates ceftazidime/avibactam therapy as Class B CPOs are intrinsically resistant to this agent. The implications for ceftazidime/avibactam therapy for infections by Class D carbapenemase producers are currently unclear. An accurate negative result is also a good result for guiding patient management and for infection control.

Misclassification of a carbapenemase as Class B or Class D is regarded as unhelpful but relatively benign. This misclassification does not detract from the value of the detection of a carbapenemase, but it might delay consideration of ceftazidime/avibactam therapy until susceptibility results become available. A "no answer" result is also unhelpful in that it confers neither benefit nor harm.

Results regarded as potentially harmful include an incorrect classification of a Class B carbapenemase as a Class A carbapenemase. This could lead to a patient receiving ineffective ceftazidime/avibactam therapy. A false negative result is also regarded as potentially harmful as the consequence of an undetected CPO may be ineffective therapy and/or a failure to implement infection control measures.

Non-limiting examples of bacteria, antibiotics, inhibitors and detection reagents are provided herein. Also provided are non-limiting examples of concentration ranges for the antibiotics and inhibitors. However, one of ordinary skill in the art will readily appreciate that the detection tests can be adapted to be performed with other bacteria, antibiotics, inhibitors and detection reagents, and can be performed with other concentration ranges of the antibiotics and inhibitors.

Antibiotics

Non-limiting examples of antibiotics include temocillin (TEM), doripenem (DOR) or meropenem (MEM). TEM (disodium 6beta-(2-carboxy-2-thien-3-ylacetamido)-6alpha-methoxypenicillanate), is a carboxypenicillin that is stable to hydrolysis of chromosomal and plasmid β-lactamases, including extended-spectrum β-lactamases (ESBLs) and AmpC-type β-lactamases. TEM is currently used in Belgium and the United Kingdom for the treatment of multi drug-resistant, Enterobacteriaceae.

In some embodiments, the concentration range of TEM in detection tests provided herein is, or is about, 6 μg/ml to 1024 μg/ml. In some embodiments, the concentration range of TEM in detection tests provided herein is, or is about, 12 μg/ml to 512 μg/ml (FIG. 1-FIG. 6). Another concentration range is, or is about, 32 μg/ml to 124 μg/ml, with some embodiments having a concentration of about 64 μg/ml. In some embodiments, the concentration range of TEM in detection tests provided herein is, or is about, 32 μg/ml to 100 μg/ml. In some embodiments, the concentration range of TEM in detection tests provided herein is, or is about, 32 μg/ml to 75 μg/ml. In some embodiments, the concentration range of TEM in detection tests provided herein is, or is about, 55 μg/ml to 75 μg/ml.

MEM is an ultra-broad-spectrum injectable antibiotic used to treat a wide variety of infections. It is a β-lactam and belongs to the carbapenem subgroup. It penetrates well into many tissues and body fluids, including cerebrospinal fluid, bile, heart valve, lung, and peritoneal fluid. MEM is bactericidal except against *Listeria monocytogenes*, where it is bacteriostatic. It inhibits bacterial wall synthesis like other β-lactam antibiotics.

Figure 31:
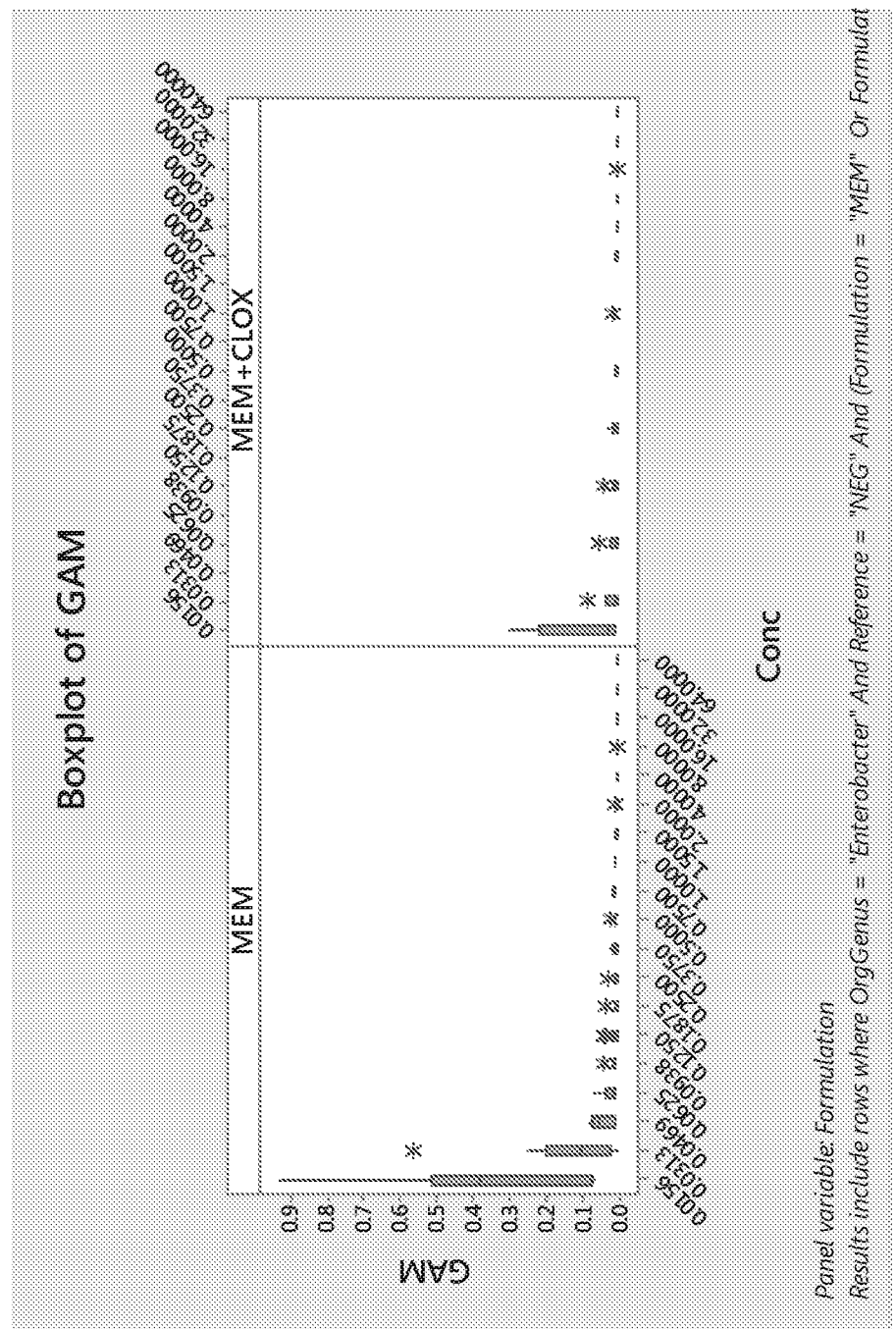
FIG. 31 shows a boxplot of MEM GAM data and MEM/CLOX GAM data for enteric bacteria expressing Class C carbapenemase.

In some embodiments, the concentration range of MEM in detection tests provided herein is, or is about, 0.0039 μg/ml to 128 μg/ml. In some embodiments, the concentration range of MEM in detection tests provided herein is, or is about, 0.0078 μg/ml to 64 μg/ml (FIG. 7-FIG. 12, FIG. 23 and FIG. 24). In some embodiments, the concentration range of MEM in detection tests provided herein is, or is about, 0.0156 μg/ml to 64 μg/ml (FIG. 31). Another concentration range is about 0.016 μg/ml to about 1 μg/ml, with some embodiments having a concentration of about 0.0625 μg/ml.

DOR is an ultra-broad-spectrum injectable antibiotic. It is a beta-lactam and belongs to the carbapenem subgroup. DOR can be used for bacterial infections such as complex abdominal infections, pneumonia within the setting of a hospital, and complicated infections of the urinary tract including kidney infections with septicemia. DOR decreases the process of cell wall growth, which eventually leads to elimination of the infectious cell bacteria altogether.

In some embodiments, the concentration range of DOR in detection tests provided herein is, or is about, 0.0078 μg/ml to 128 μg/ml. In some embodiments, the concentration range of DOR in detection tests provided herein is, or is about, 0.0156 μg/ml to 64 μg/ml (FIG. 13-FIG. 22). Another concentration range is, or is about, 0.0313 μg/ml to 4 μg/ml, with some embodiments having a concentration of about 1 μg/ml.

Non-limiting examples of other antimicrobial agents include CLOX, EDTA, and RPX7009, Avibactam, BLI-489, and DPA.

In some embodiments, the concentration range of CLOX is, or is about, 40 µg/ml to 160 µg/ml, with some embodiments having a concentration of about 100 µg/ml.

In some embodiments, the concentration range of EDTA is, or is about, 100 µg/ml to 400 µg/ml, with some embodiments having a concentration of about 250 µg/ml.

In some embodiments, the concentration range of RPX7009 is, or is about, 3 µg/ml to 15 µg/ml, with some embodiments having a concentration of about 8 µg/ml.

In some embodiments, the concentration range of Avibactam is, or is about, 1 µg/ml to 10 µg/ml, with some embodiments having a concentration of about 4 µg/ml.

In some embodiments, the concentration range of BLI-489 is, or is about, 1 µg/ml to 10 µg/ml, with some embodiments having a concentration of about 5 µg/ml.

In some embodiments, the concentration range of DPA is, or is about, 50 µg/ml to 400 µg/ml, with some embodiments having a concentration of about 178 µg/ml.

Ambler Class Carbapenemase

Carbapenemases are β-lactamase enzymes (β-lactamases) that have a wide range of hydrolytic activity. Carbapenemases are capable of hydrolyzing penicillins, cephalosporins, monobactams, and carbapenems. The rapid dissemination of these enzymes in clinically important bacteria, such as Enterobacteriaceae and non-fermentative bacteria, including *Acinetobacter* and *Pseudomonas* species, poses a major threat to public health.

Carbapenemases belong to two major families. The two major families are distinguished by the hydrolytic mechanism (either zinc or serine) at their active site. Classification that is based on amino acid homology (Ambler classification) resulted in four major classes, namely, Ambler Classes A, B, C, and D.

Ambler Class A carbapenemases contain the amino acid serine at their active site. Bacteria expressing Ambler Class A carbapenemases are sensitive to mechanism based inhibitors. Mechanism based inhibition is an irreversible form of enzyme inhibition that occurs when an enzyme binds a substrate analogue and forms an irreversible complex with it through a covalent bond during the "normal" catalysis reaction. Non-limiting examples of Class A carbapenemases include KPC (e.g., KPC-like, KPC-2 or KPC-3), NMC-A, IMI and SME enzymes.

Ambler Class B carbapenemases contain the metal zinc at their active site. Bacteria expressing Ambler Class B carbapenemases are sensitive to chelating agents that bind and remove zinc (metal ion) from the active site of Class B carbapenemases. Non-limiting examples of Class B carbapenemases (metallo-β-lactamases) include NDM (e.g., NDM-like or NDM-1), GIM, SPM (e.g., SPM-like or SPM-1), IMP (e.g., IMP-like or IMP-1), and VIM (e.g., VIM-like or VIM-1) enzymes.

Similar to Ambler Class A carbapenemases, Ambler Class C β-lactamases contain the amino acid serine at their active site. However, Ambler Class C β-lactamases do not hydrolyze carbapenems. Overexpression of Ambler Class C β-lactamases in bacteria does not make them insensitive to carbapenems, and are therefore, not carbapenemases. Nevertheless, carbapenem resistance can arise when other mutations are present, including loss of porin in the outer membrane or efflux pump activation. Overexpression of Ambler Class C β-lactamases in bacteria makes the bacteria insensitive to broad spectrum cephalosporins.

Although bacteria expressing Ambler Class C β-lactamases (referred to herein for convenience as Class C carbapenemases) can be sensitive to carbapenems, yet they can become insensitive to carbapenems by other mechanisms. Bacteria expressing Class C carbapenemase must be selectively rendered sensitive in phenotypic tests to detect Class A, B and D carbapenemases. Otherwise a false positive interpretation may be obtained.

Similar to Ambler Classes A and C, Ambler Class D carbapenemases also contain the amino acid serine at their active site. However, Class D carbapenemases do not have a known common specific inhibitor at this time. Thus, phenotypic tests for identification of Class D carbapenemase are typically done indirectly, by determining that the resistance is not due to Class A, B or C, leaving Class D as the presumptive identification. For example, phenotypic tests for identification of Class D carbapenemase are performed indirectly by a process of elimination of the other Ambler classes of carbapenemases. Non-limiting examples of Class D carbapenemases include OXA-23, 40, 48, 58, 72, 181, and 232 enzymes.

In some cases, more than one Class of carbapenemase can be produced by an organism. For example, in some embodiments, 2, 3 or 4 classes of carbapenemases are produced by an organism.

Non-limiting examples of non-carbapenemase resistance mechanisms include ESBLs (e.g., CTX-M-1, CTX-M-2CTX-M-9, CTX-M-12, CTX-M14, CTX-M-15, CTX-M-15-like, CTX-M-28, SHV ESBL, SHV-5, SHV-5-like, SHV-12, SHV-12-like, SHV-18, TEM ESBL, OXA-45), AmpCs (including hyperproducers) (e.g., Plasmid-mediated AmpC such as ACT-1, ACT-like, CMY (CMY-like, CMY-2, CMY-2-like) CMY-16, DHA-1, DHA-like, FOX-1, FOX-5, LAT-4, MIR-like, MOX-1, K1), broad spectrum β-lactamases and porin mutants.

Carbapenemase Inhibitors and Differentiators

Non-limiting classes of inhibitors of carbapenemase include: mechanism based inhibitors chelating agents and β-lactam antibiotics.

Non-limiting examples of mechanism based inhibitors include (β-lactamase inhibitors, and include, without limitation, boronic acid based inhibitors, vaborbactam (RPX7009), BLI-489, CLOX, clavulanate, tazobactam, or avibactam.

In addition, bacteria expressing Ambler Class A carbapenemases are also typically sensitive to temocillin at lower concentrations than most bacteria expressing Ambler Class B or Class D carbapenemase.

Bacteria expressing Ambler Class A carbapenemases are sensitive to TEM at lower concentrations, for example, TEM concentrations in the range of about 6 µg/ml to about 12 µg/ml (FIG. 1). On the other hand, bacteria expressing Class D typically exhibit an elevated MIC to TEM, and therefore, are sensitive at much higher concentration of TEM, for example, ≥ about 128 µg/ml (FIG. 1).

Thus, temocillin concentrations that inhibit growth of bacteria that express Class A would not inhibit growth of bacteria that express Class D and temocillin can be used to differentiate between bacteria expressing Class A and Class D carbapenemases.

Non-limiting examples of chelating agents include ethylenediaminetetraacetic acid (EDTA) and dipicolinic acid (DPA), which bond to and sequester metal ions.

Bacteria expressing Ambler Class B carbapenemases are sensitive to EDTA at 250 µg/ml (FIG. 3, FIG. 4, FIG. 15 and FIG. 16), EDTA at 280 µg/ml (FIG. 5 and FIG. 6) and DPA at 180 µg/ml (FIG. 9, FIG. 10, FIG. 21 and FIG. 22).

A non-limiting example of a differentiator for Class C β-lactamases is cloxacillin (CLOX), which is a penicillin derivative that is useful in treating infections caused by *Staphylococci*. Bacteria expressing Class C β-lactamases are sensitive to CLOX at a concentration of about 100 µg/ml, while bacteria expressing Classes A, B or D are typically not, allowing for differentiation of Class C from Classes A, B and D (FIG. 31).

BD Phoenix™ CPO Detect Detection Tests

The BD Phoenix™ CPO Detect detection test can be used as a qualitative in vitro diagnostic test which phenotypically detects the expression of carbapenemases in bacteria. In addition to providing detection of bacteria expressing carbapenemases, it further distinguishes the type of carbapenemase enzyme into Ambler Class A, Class B or Class D. With BD Phoenix™ CPO Detect detection test, clinical laboratories will be able to test all gram-negative bacteria isolated from patient samples for identification and antibiotic susceptibility of the isolate as well as identifying the Ambler Class of carbapenemase expression by the bacteria.

In some embodiments, non-limiting examples of the sample can comprise one or more of blood, urine, stool, sputum, saliva, etc. The sample is collected from a human, one or more companion animals, or one or more commercially important animals. In some embodiments, the human, one or more companion animals, or one or more commercially important animals can have a bacterial infection. The bacterial infection can be due to enteric bacteria or non-fermenting bacteria. In some embodiments, the bacteria can be other than enteric bacteria or non-fermenting bacteria.

Non limiting examples of enteric bacteria include *Klebsiella pneumoniae, Escherichia coli* and *Enterobacter aerogenes*.

Non-limiting examples of non-fermenting bacteria include *Pseudomonas aeruginosa* and *Acinetobacter baumanii* complex.

One of ordinary skill in the art will appreciate that BD Phoenix™ CPO Detect can be adapted for bacteria other than enteric and non-fermenting bacteria.

This procedure provides a simplified method to accurately identify carbapenemase production along with differentiation of the Ambler classification, which is necessary for appropriate antibiotic treatment and surveillance, allowing for appropriate patient isolation from other non-infected patients. The proposed test can be incorporated with a routine susceptibility test (AST) and therefore does not require additional testing or costs. This test also offers rapid identification of the carbapenemase while the AST is in progress. This will save time and cost to the hospital and patient as a separate test for CPOs does not have to be ordered by the physician.

The detection tests comprise a plurality of wells. In some embodiments, the input in each well is a combination of a sample comprising one or more bacteria, one or more antibiotics, optionally one or more inhibitors, and one or more detection reagents. Appropriate controls for the detection tests can comprise a plurality of wells, wherein each well comprises a sample comprising one or more bacteria, and/or one or more antibiotics, and/or one or more inhibitors, and/or one or more detection reagents. In some embodiments, samples are run in duplicate, triplicate, or more for each type of well (e.g. for a specific antibiotic(s)/inhibitor(s) combination).

Non-limiting embodiments of detection tests for enteric and non-fermenting bacteria, with various concentration ranges of one or more antibiotics, and various concentration ranges for one or more inhibitors are shown in FIG. 1-FIG. 24 and FIG. 31. These figures illustrate the concentration of the antibiotic being tested (in µg/ml) along the x-axis (not every concentration is tested in every figure), and the amount of growth of bacteria in the sample in the y-axis. The boxes illustrate the median, interquartile range, non-outlier minimum and maximum; with asterisks representing single outliers. Each figure has a panel for Class A, Class B, and Class D producing bacteria, as well as a panel for non-carbapenemase producing bacteria (NEG). In some embodiments, the detection tests described herein are not performed by imaging a change in cell morphology.

By way of example, FIG. 1 illustrates a test of various enteric bacteria grown in the presence of several concentrations of TEM. As shown in FIG. 1, Class A and NEG bacteria are more sensitive to TEM than Class B or D. At a concentration of 24 µg/ml nearly all Class A enteric bacterial strains tested are inhibited by TEM, while Class D are unaffected until concentrations reach 192 µg/ml. Nearly all NEG enteric bacteria are sensitive to lowest concentration of TEM. The Class B enteric bacteria tested begin to show sensitivity at 48 µg/ml as evidenced in the decrease in the average growth line, at 384 µg/ml, growth of most Class B enterics is inhibited. FIG. 1-FIG. 24 and FIG. 31 demonstrate the results of numerous combinations of antibiotic(s) with and without inhibitor(s) which can be used to differentiate between Classes A, B, D and NEG enteric and non-fermenting bacteria.

In some embodiments, the detection tests can comprise a plurality of wells comprising enteric bacteria and TEM over a range of concentrations of about 12 µg/ml to about 512 µg/ml (FIG. 1).

Figure 2:
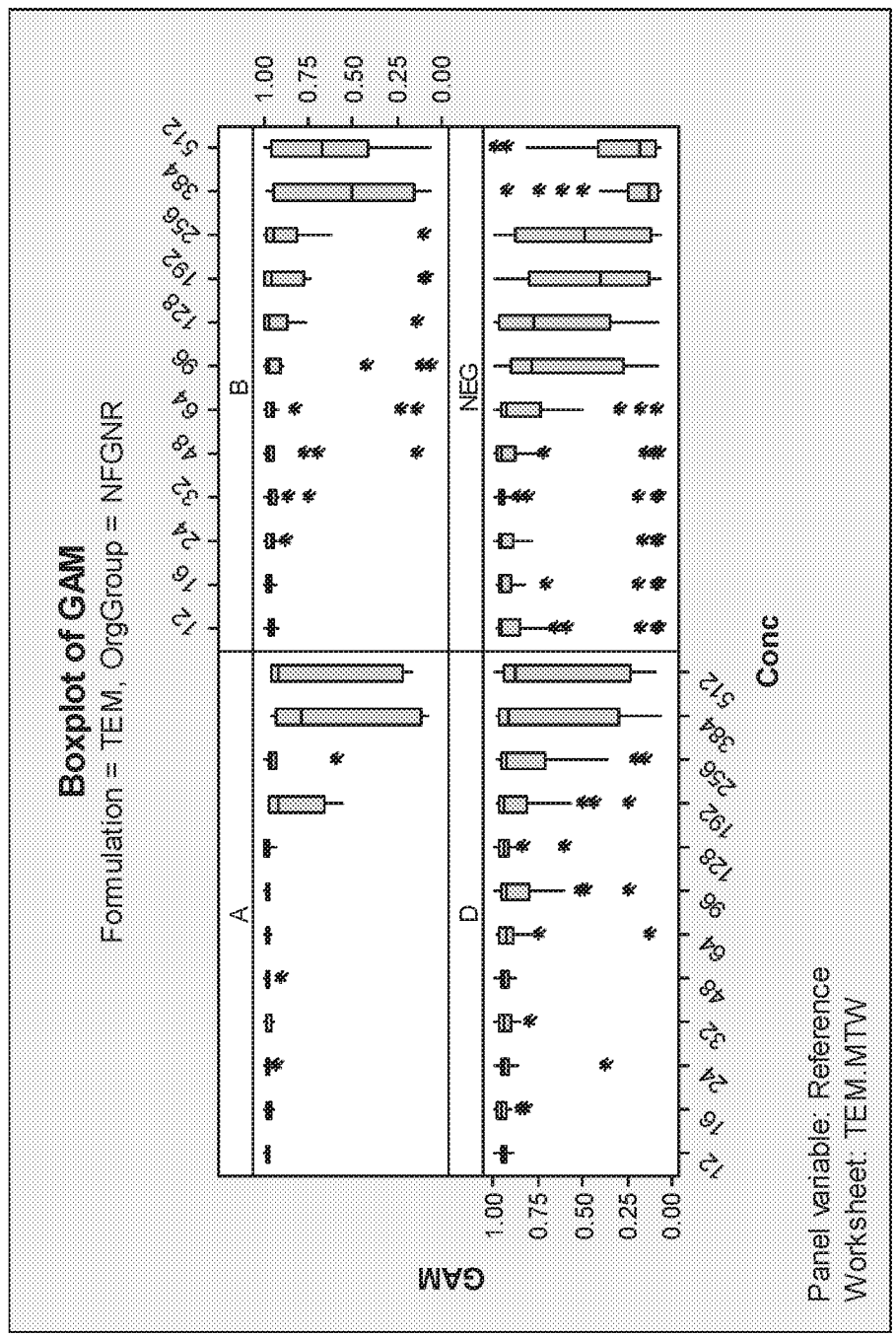
FIG. 2 shows a boxplot of TEM GAM data for non-fermenting gram negative rod bacteria expressing either Class A, Class B or Class D carbapenemase.

In some embodiments, the detection tests can comprise a plurality of wells comprising non-fermenting bacteria and TEM over a range of concentrations of about 12 µg/ml to about 512 µg/ml (FIG. 2).

Figure 3:
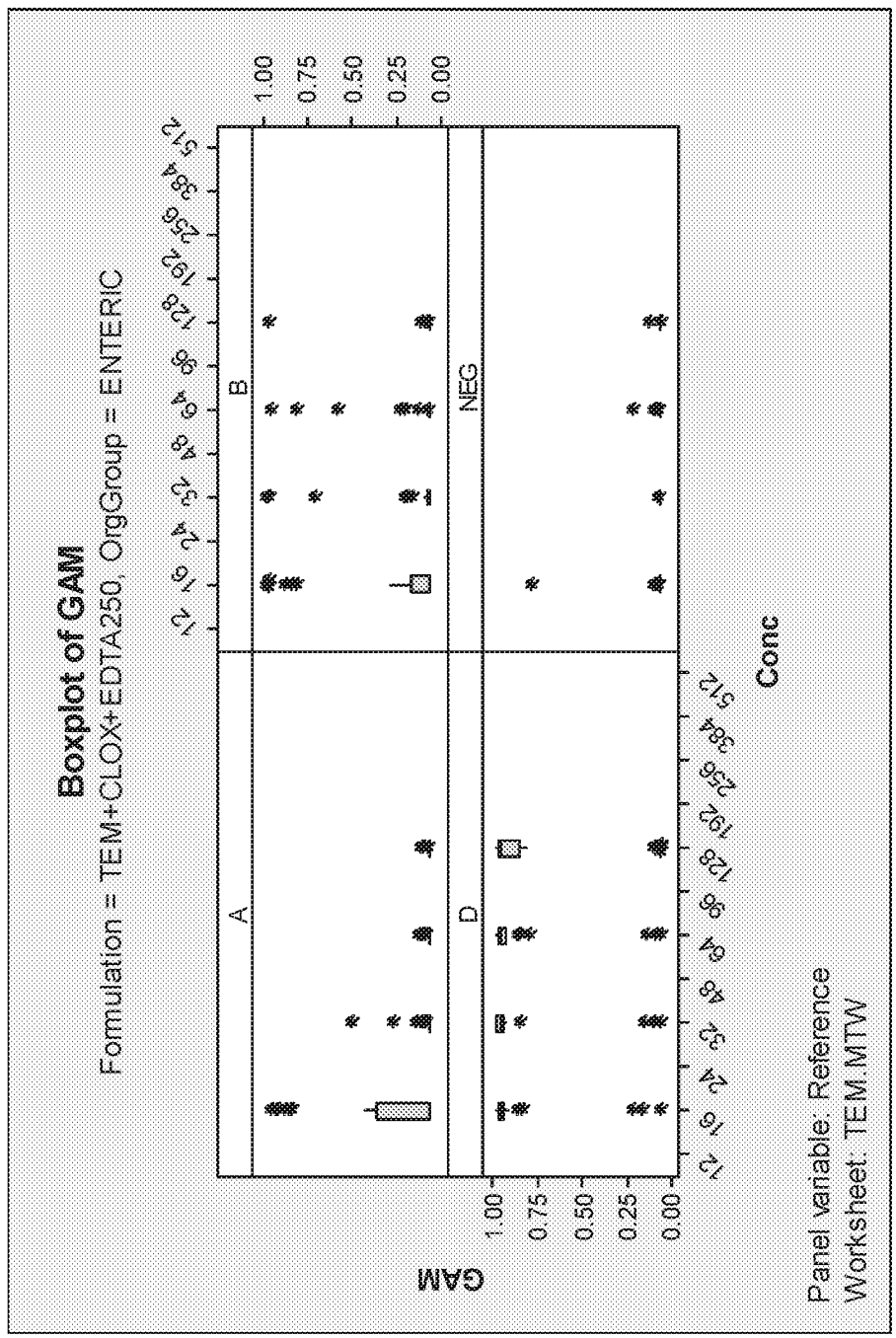
FIG. 3 shows a boxplot of TEM/CLOX/EDTA GAM data for enteric bacteria expressing either Class A, Class B or Class D carbapenemase.

In some embodiments, the detection tests can comprise a plurality of wells comprising enteric bacteria, CLOX at 0.1 mg/ml, EDTA at 250 µg/ml, and TEM over a range of concentrations of about 12 µg/ml to about 512 µg/ml (FIG. 3).

Figure 4:
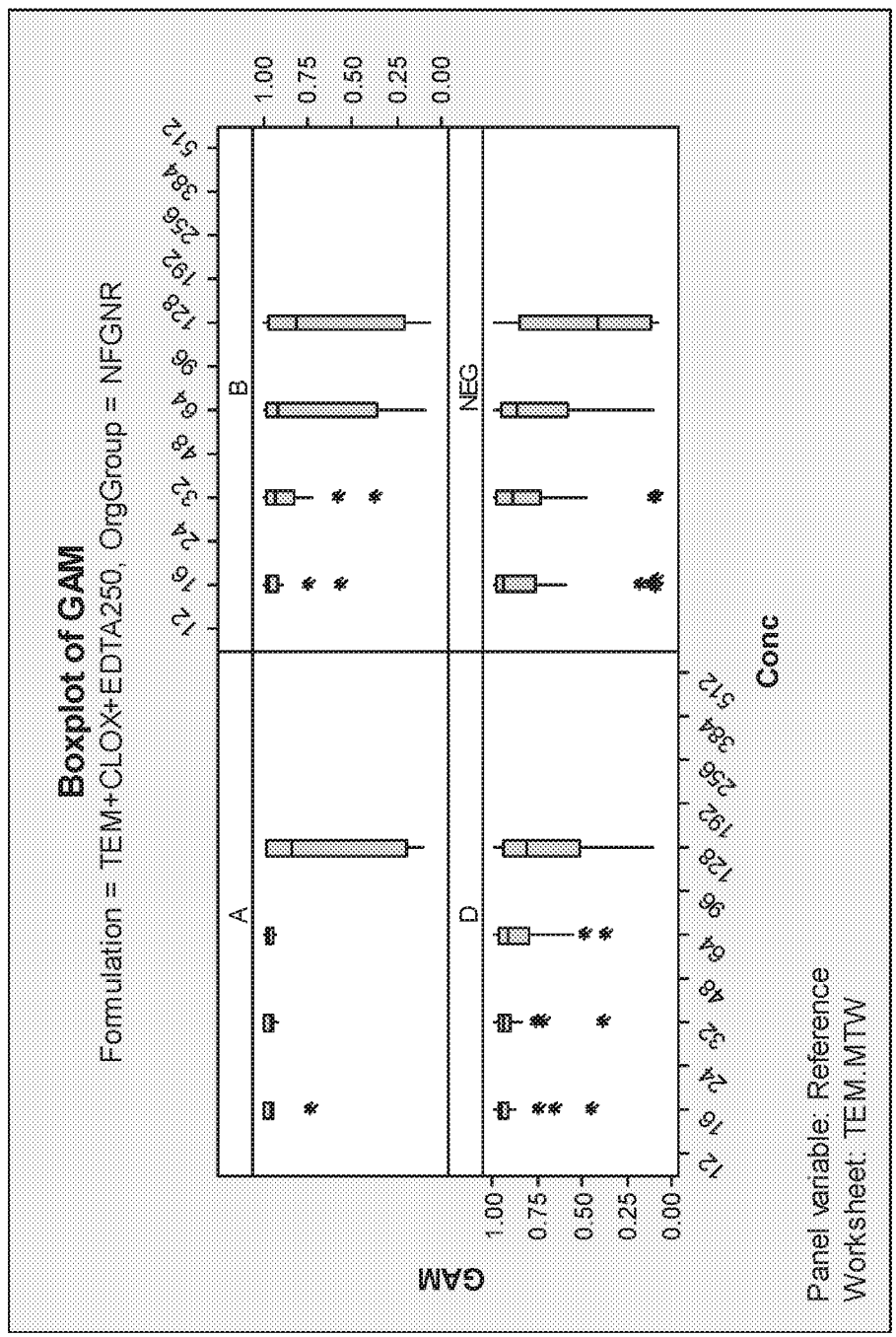
FIG. 4 shows a boxplot of TEM/CLOX/EDTA GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, EDTA at 250 µg/ml, and TEM over a range of concentrations of about 12 µg/ml to about 512 µg/ml (FIG. 4).

Figure 5:
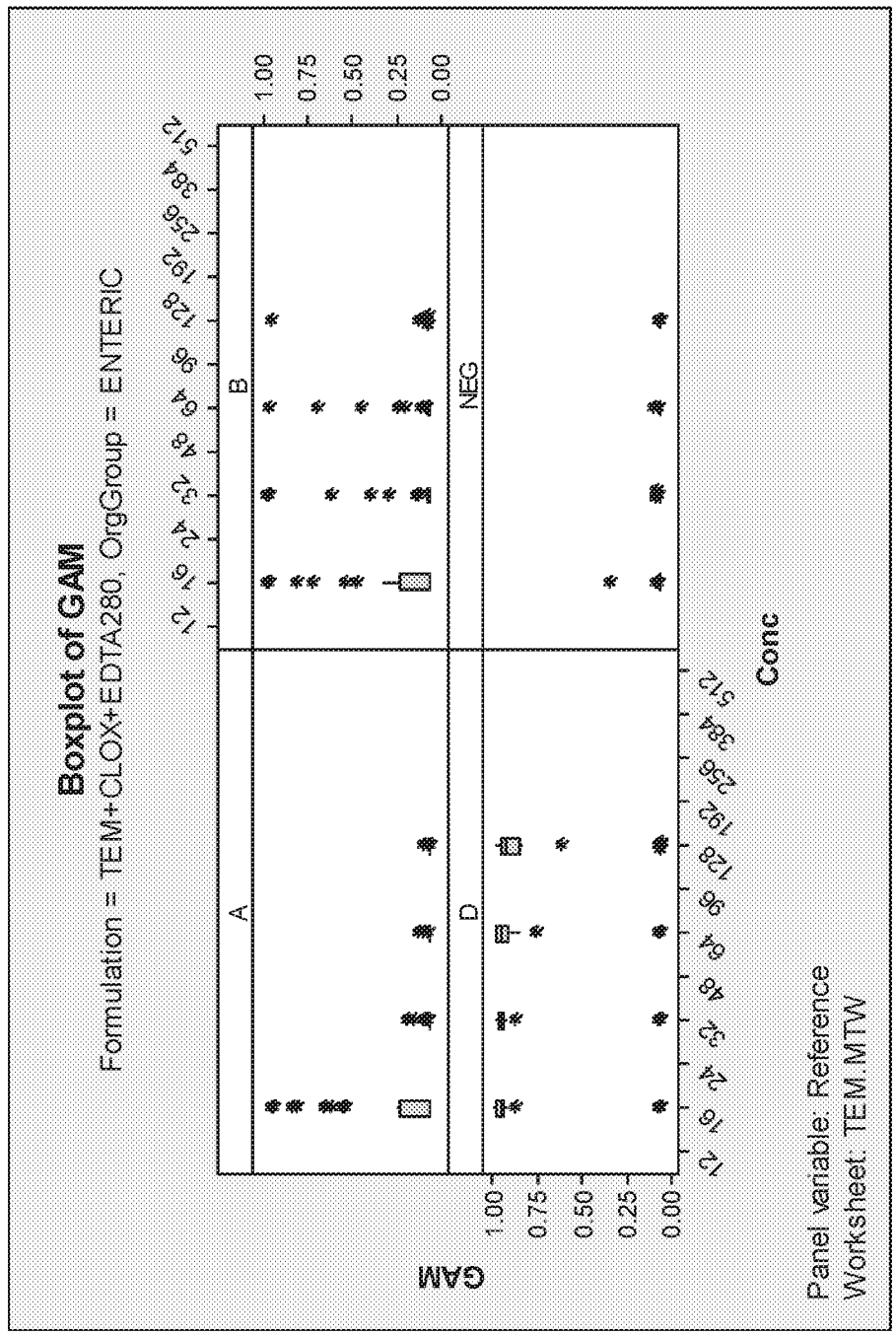
FIG. 5 shows a boxplot of TEM/CLOX/EDTA GAM data for enteric bacteria expressing either Class A, Class B or Class D carbapenemase.

In some embodiments, the detection tests can comprise a plurality of wells comprising enteric bacteria, CLOX at 0.1 mg/ml, EDTA at 280 µg/ml, and TEM over a range of concentrations of about 12 µg/ml to about 512 µg/ml (FIG. 5).

Figure 6:
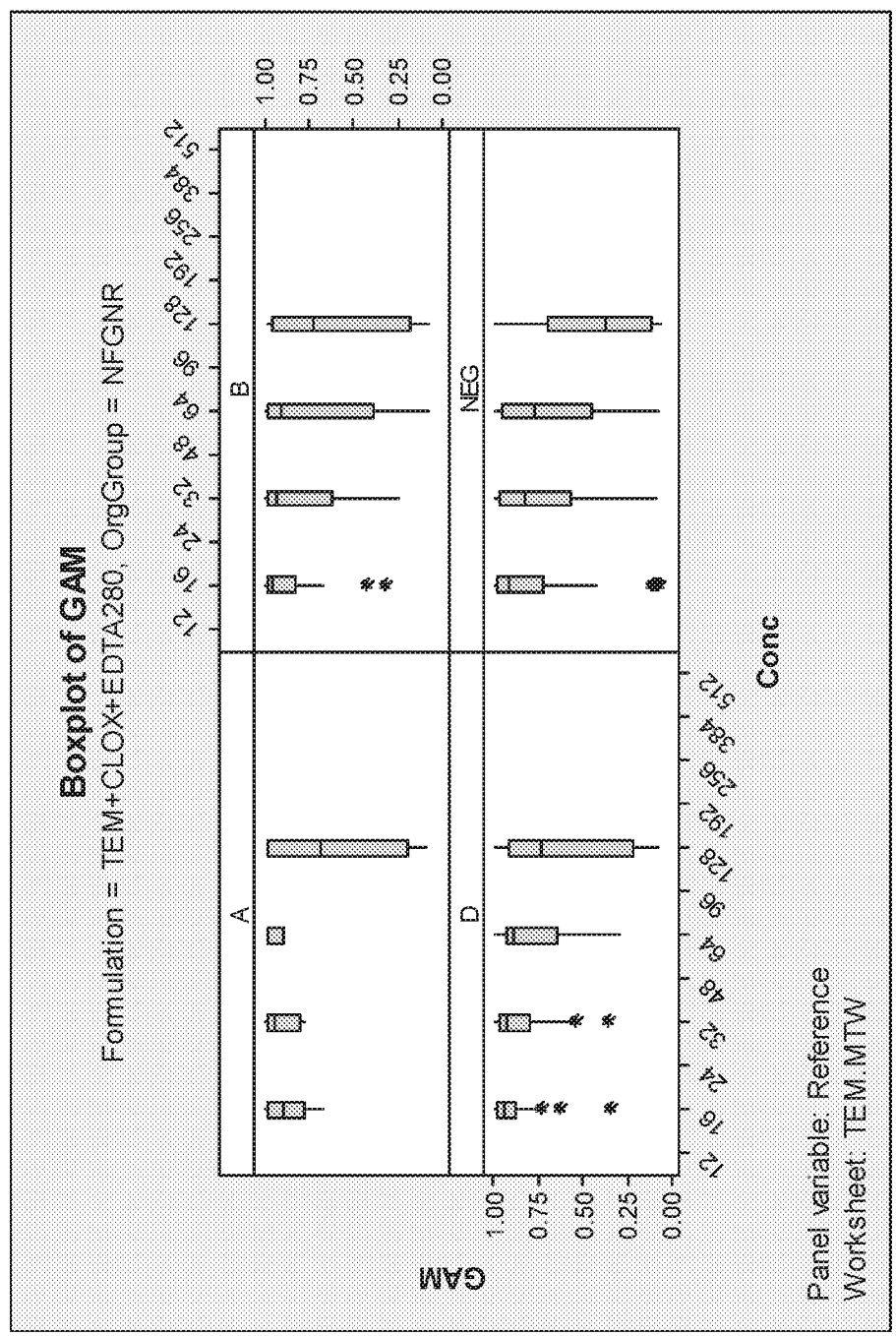
FIG. 6 shows a boxplot of TEM/CLOX/EDTA GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, EDTA at 280 µg/ml, and TEM over a range of concentrations of about 12 µg/ml to about 512 µg/ml (FIG. 6).

Figure 7:
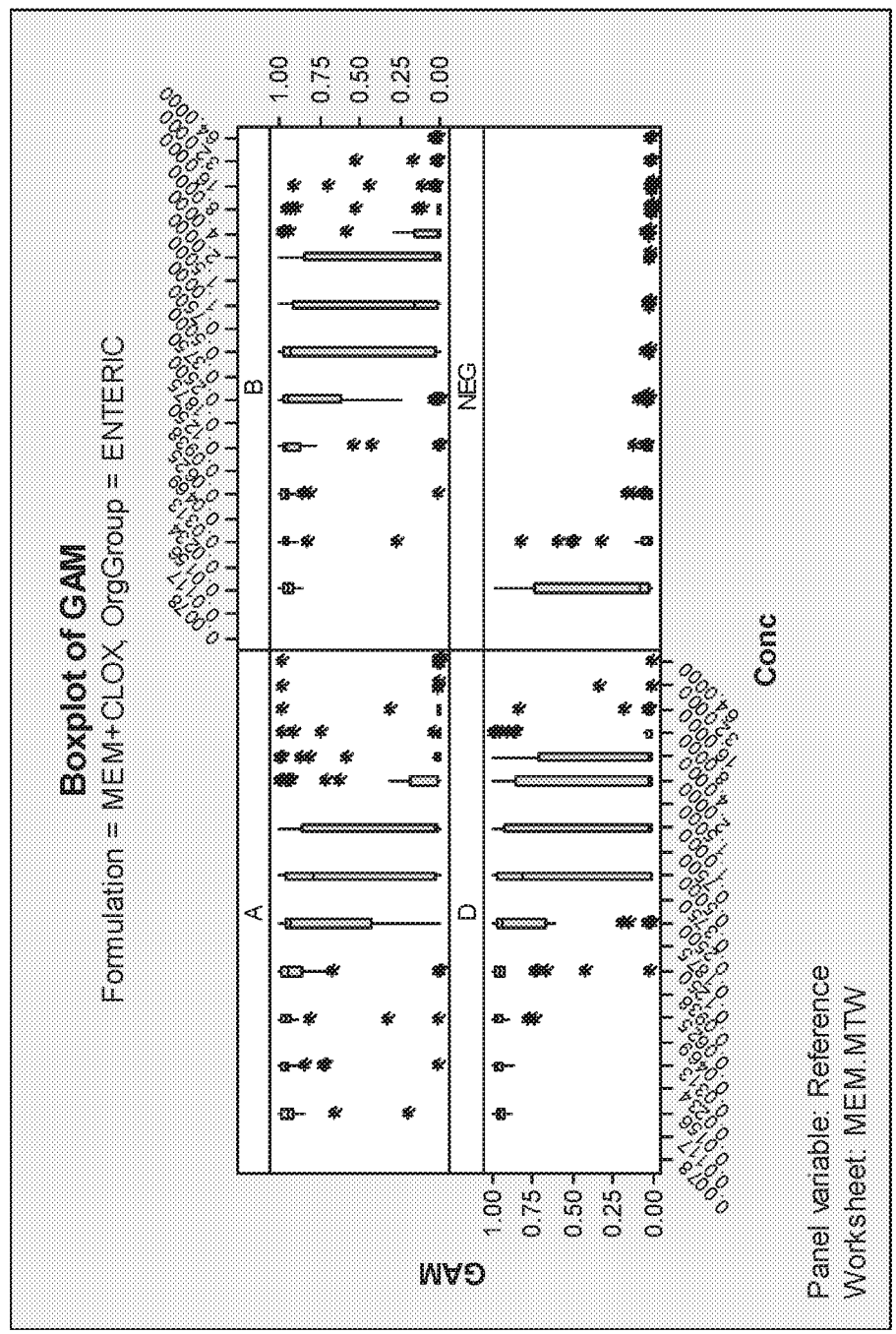
FIG. 7 shows a boxplot of MEM/CLOX GAM data for enteric bacteria expressing either Class A, Class B or Class D carbapenemase.

In some embodiments, the detection tests can comprise a plurality of wells comprising enteric bacteria, CLOX at 0.1 mg/ml, and MEM over a range of concentrations of about 0.0078 µg/ml to about 64 µg/ml (FIG. 7).

Figure 8:
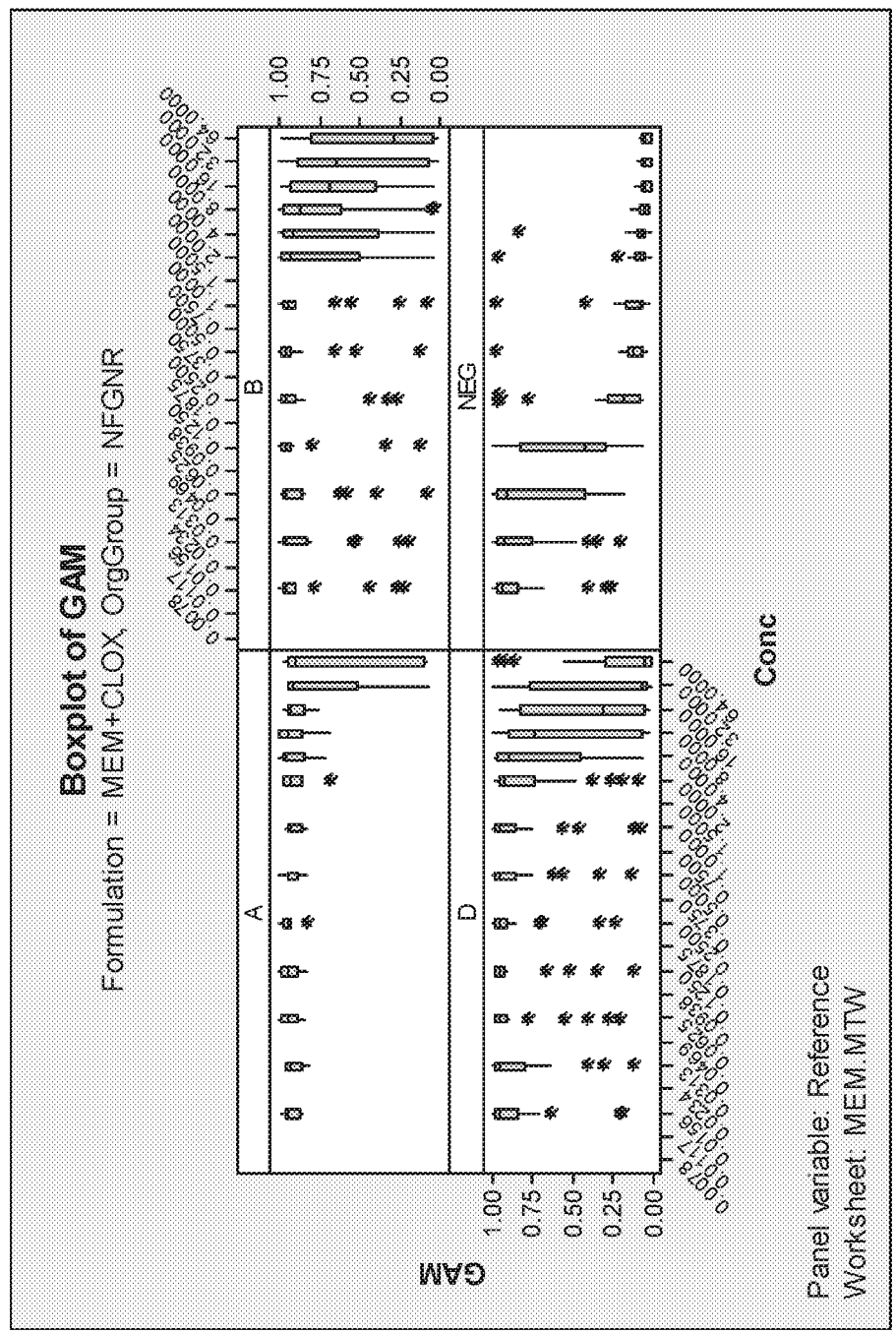
FIG. 8 shows a boxplot of MEM/CLOX GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, and MEM over a range of concentrations of about 0.0078 µg/ml to about 64 µg/ml (FIG. 8).

Figure 9:
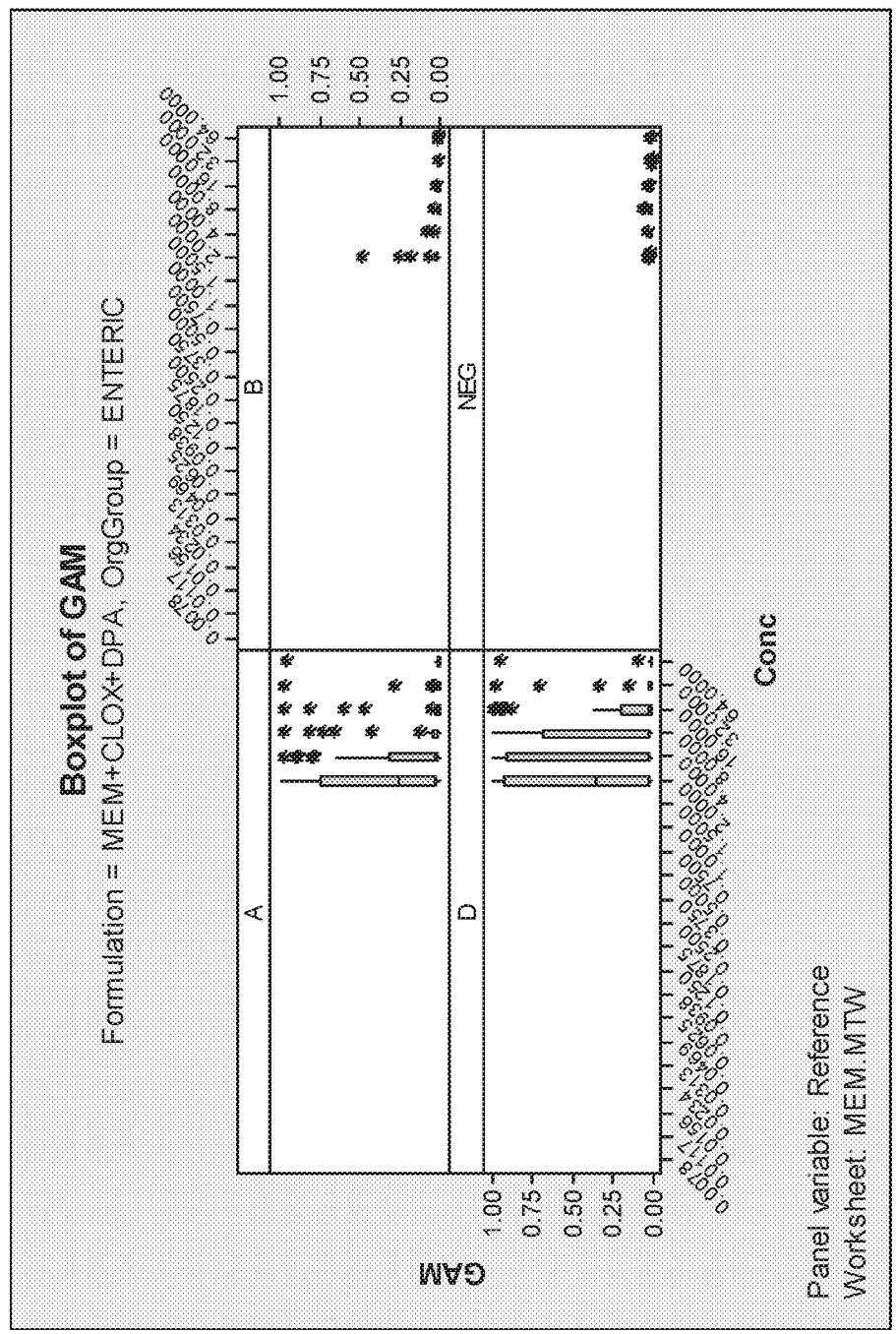
FIG. 9 shows a boxplot of MEM/CLOX/DPA GAM data for enteric bacteria expressing either Class A, Class B or Class D carbapenemase.

In some embodiments, the detection tests can comprise a plurality of wells comprising enteric bacteria, CLOX at 0.1 mg/ml, DPA at 0.18 mg/ml, and MEM over a range of concentrations of about 0.0078 µg/ml to about 64 µg/ml (FIG. 9).

Figure 10:
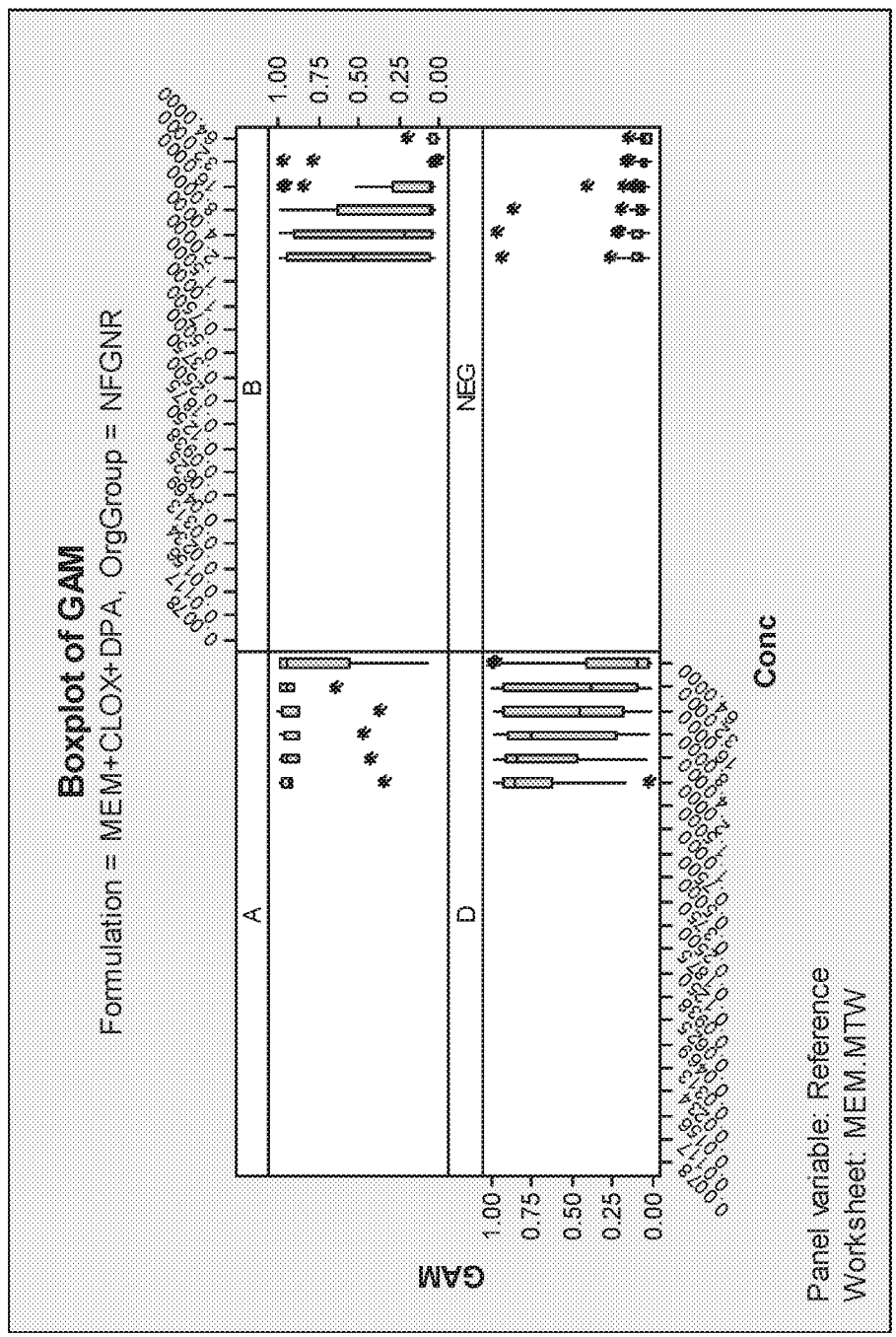
FIG. 10 shows a boxplot of MEM/CLOX/DPA GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, DPA at 0.18 mg/ml, and MEM over a range of concentrations of about 0.0078 µg/ml to about 64 µg/ml (FIG. 10).

Figure 11:
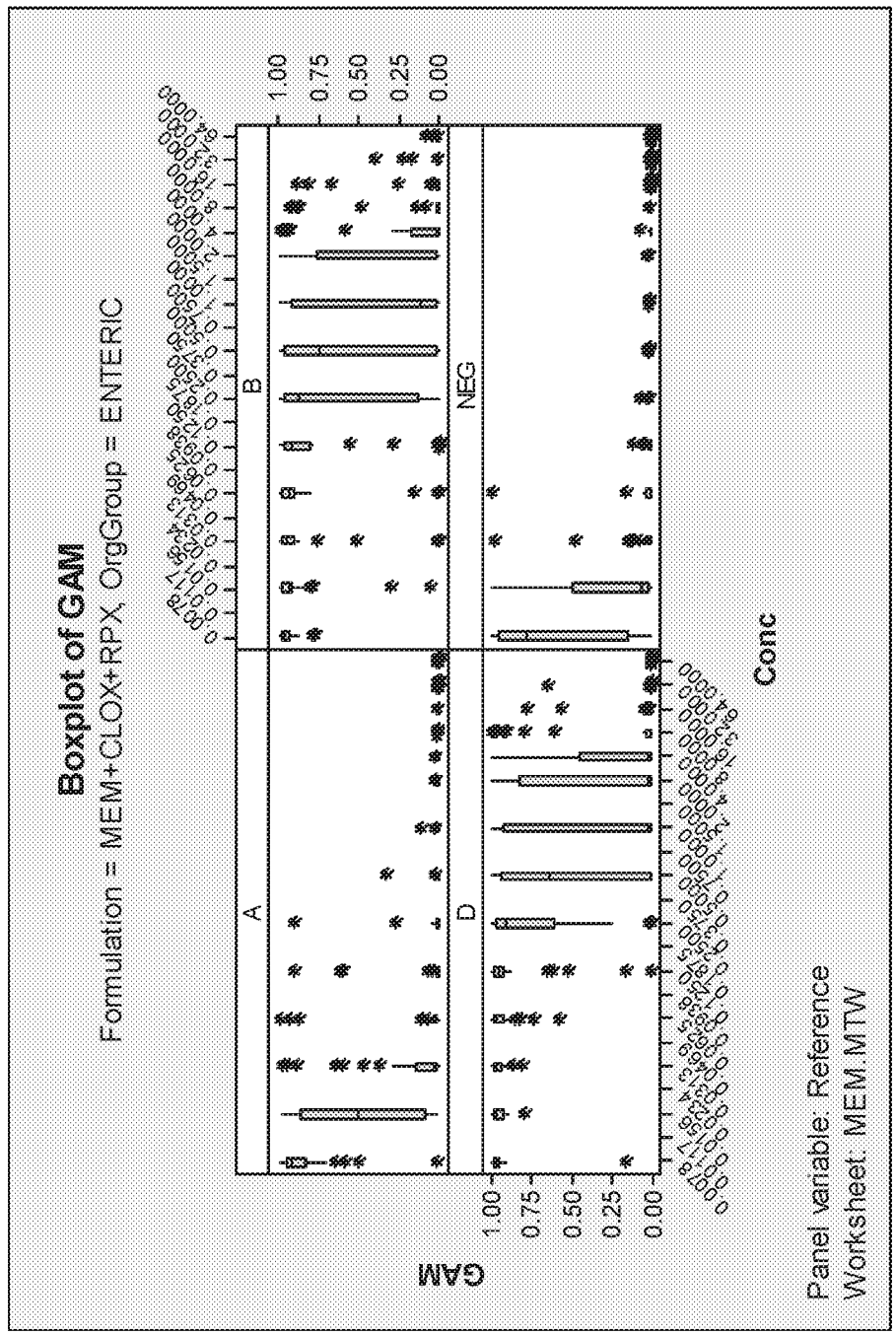
FIG. 11 shows a boxplot of MEM/CLOX/RPX GAM data for enteric bacteria expressing either Class A, Class B or Class D carbapenemase.

In some embodiments, the detection tests can comprise a plurality of wells comprising enteric bacteria, CLOX at 0.1 mg/ml, RPX at 8 µg/ml, and MEM over a range of concentrations of about 0.0078 µg/ml to about 64 µg/ml (FIG. 11).

Figure 12:
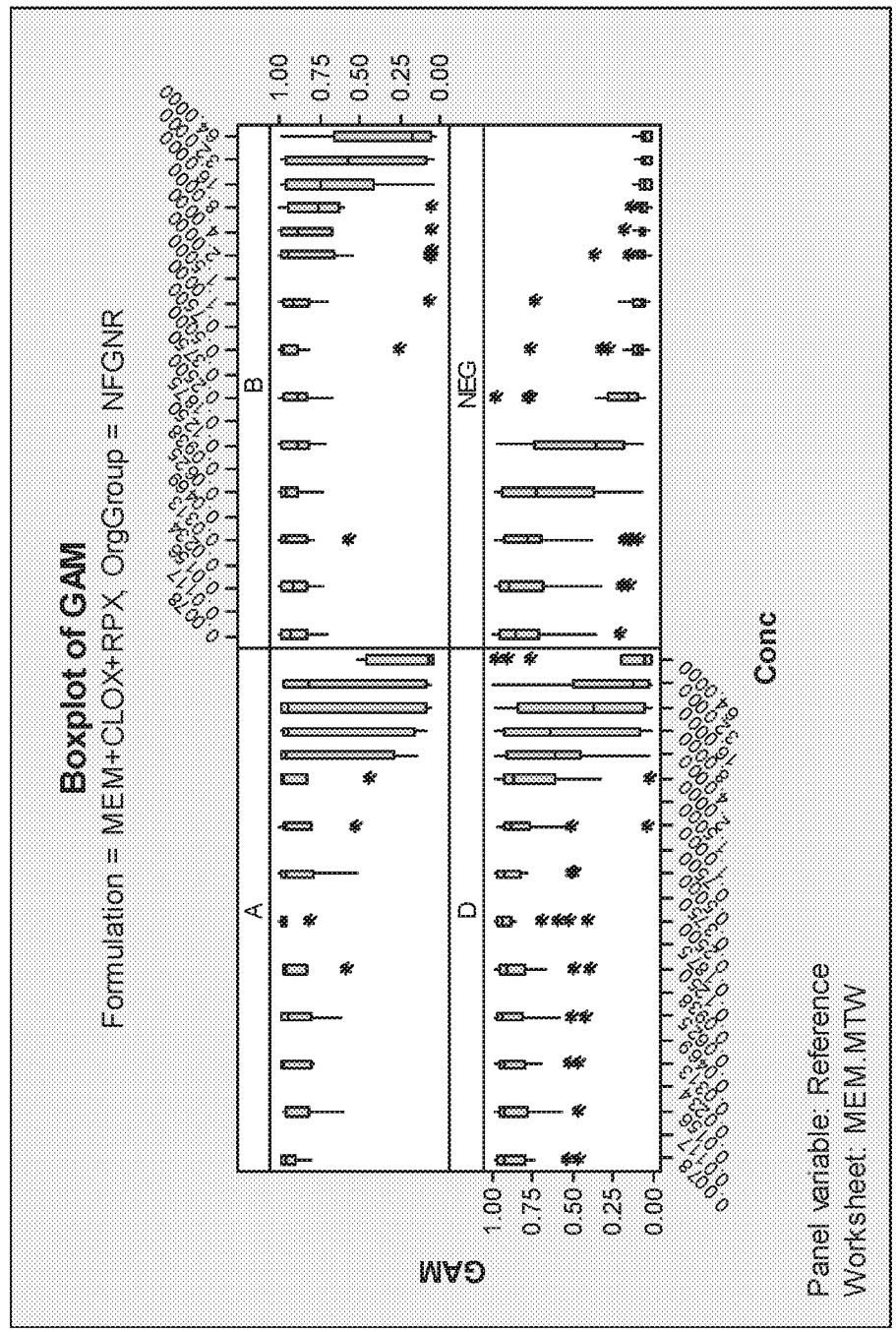
FIG. 12 shows a boxplot of MEM/CLOX/RPX GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, RPX at 8 µg/ml, and MEM over a range of concentrations of about 0.0078 µg/ml to about 64 µg/ml (FIG. 12).

Figure 13:
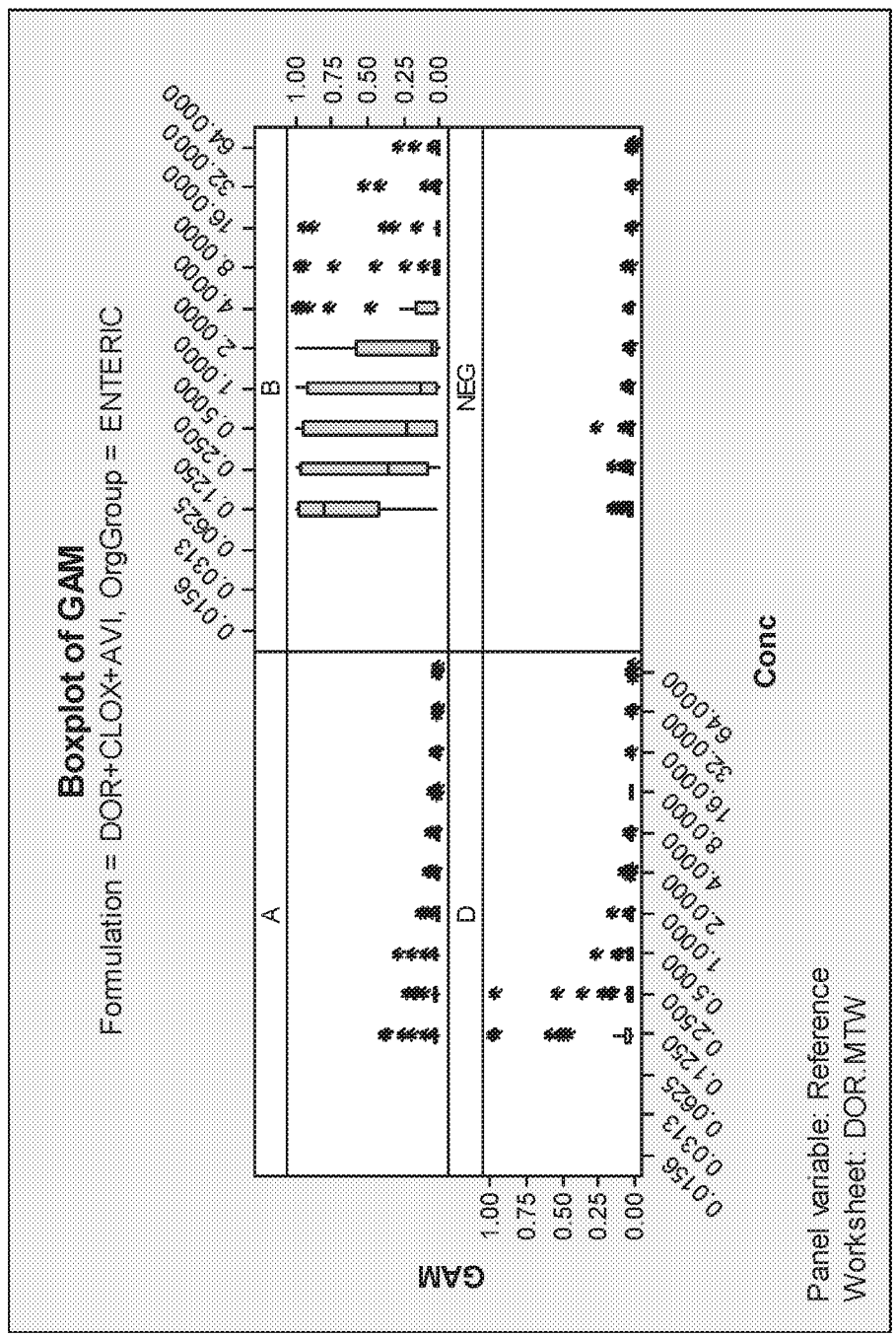
FIG. 13 shows a boxplot of DOR/CLOX/AVI GAM data for enteric bacteria expressing either Class A, Class B or Class D carbapenemase.

In some embodiments, the detection tests can comprise a plurality of wells comprising enteric bacteria, CLOX at 0.1 mg/ml, AVI at 4 µg/ml, and DOR over a range of concentrations of about 0.0156 µg/ml to about 64 µg/ml (FIG. 13).

Figure 14:
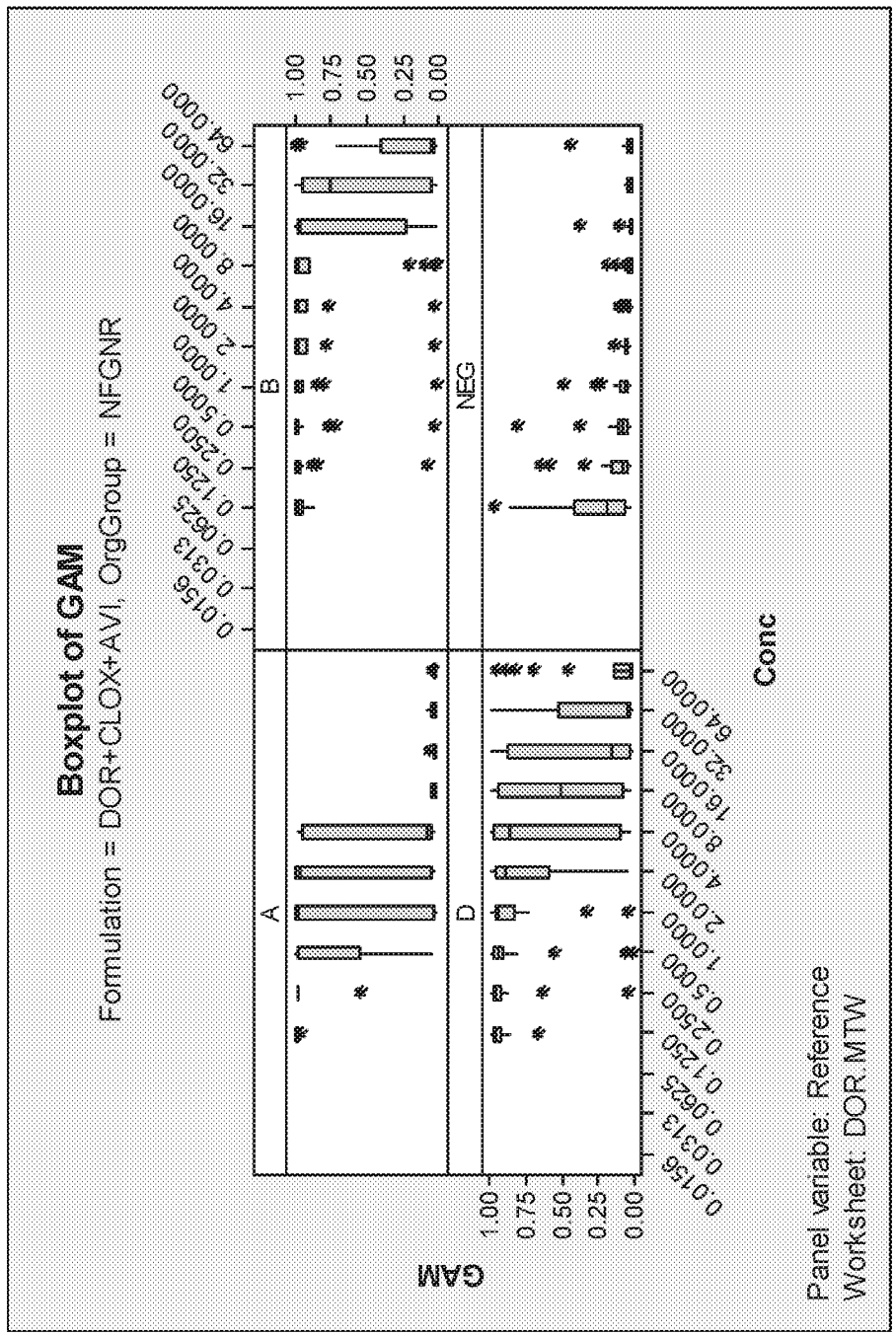
FIG. 14 shows a boxplot of DOR/CLOX/AVI GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, AVI at 4 µg/ml, and DOR over a range of concentrations of about 0.0156 µg/ml to about 64 µg/ml (FIG. 14).

Figure 15:
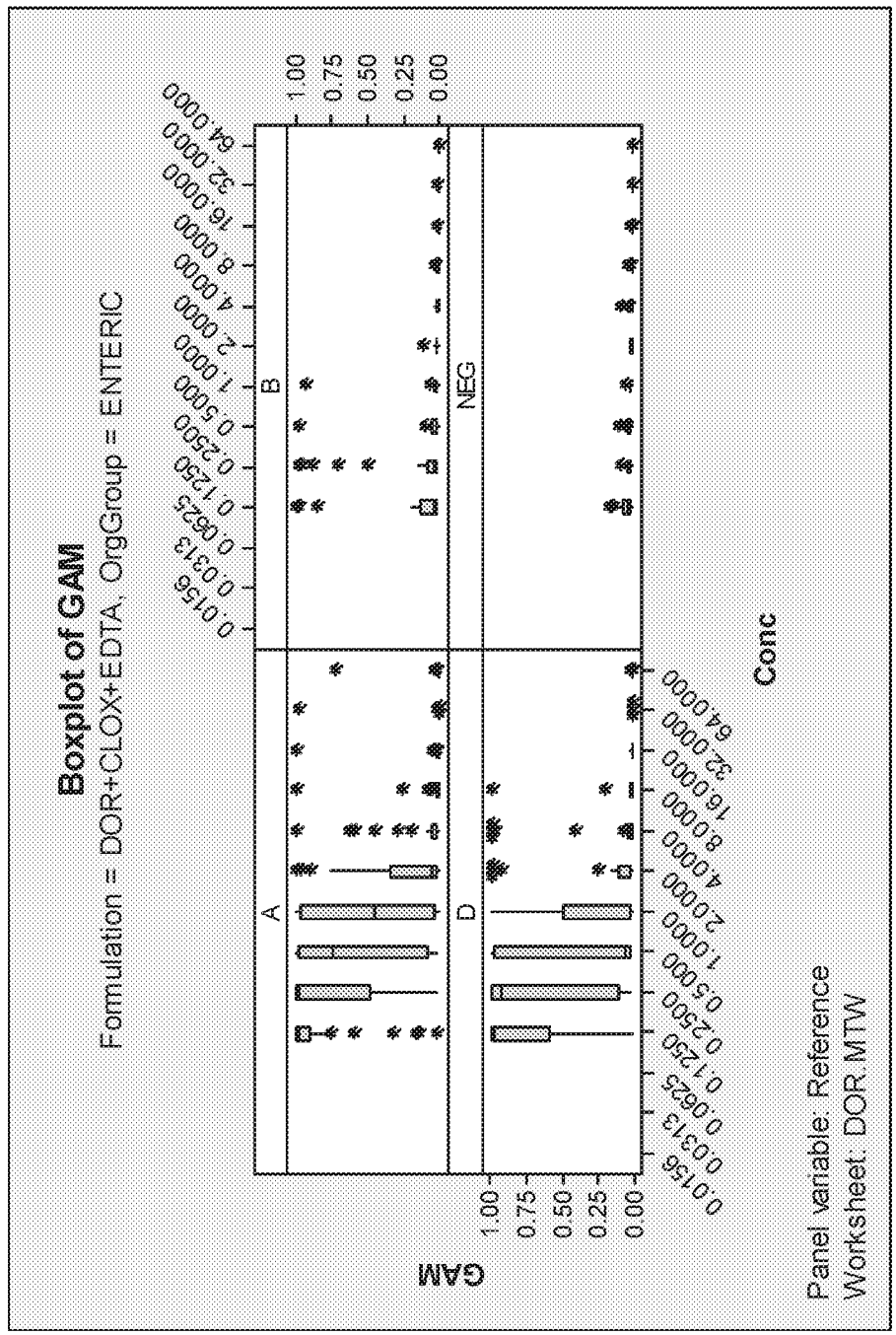
FIG. 15 shows a boxplot of DOR/CLOX/EDTA GAM data for enteric bacteria expressing either Class A, Class B or Class D carbapenemase.

In some embodiments, the detection tests can comprise a plurality of wells comprising enteric bacteria, CLOX at 0.1 mg/ml, EDTA at 0.25 mg/ml, and DOR over a range of concentrations of about 0.0156 µg/ml to about 64 µg/ml (FIG. 15).

Figure 16:
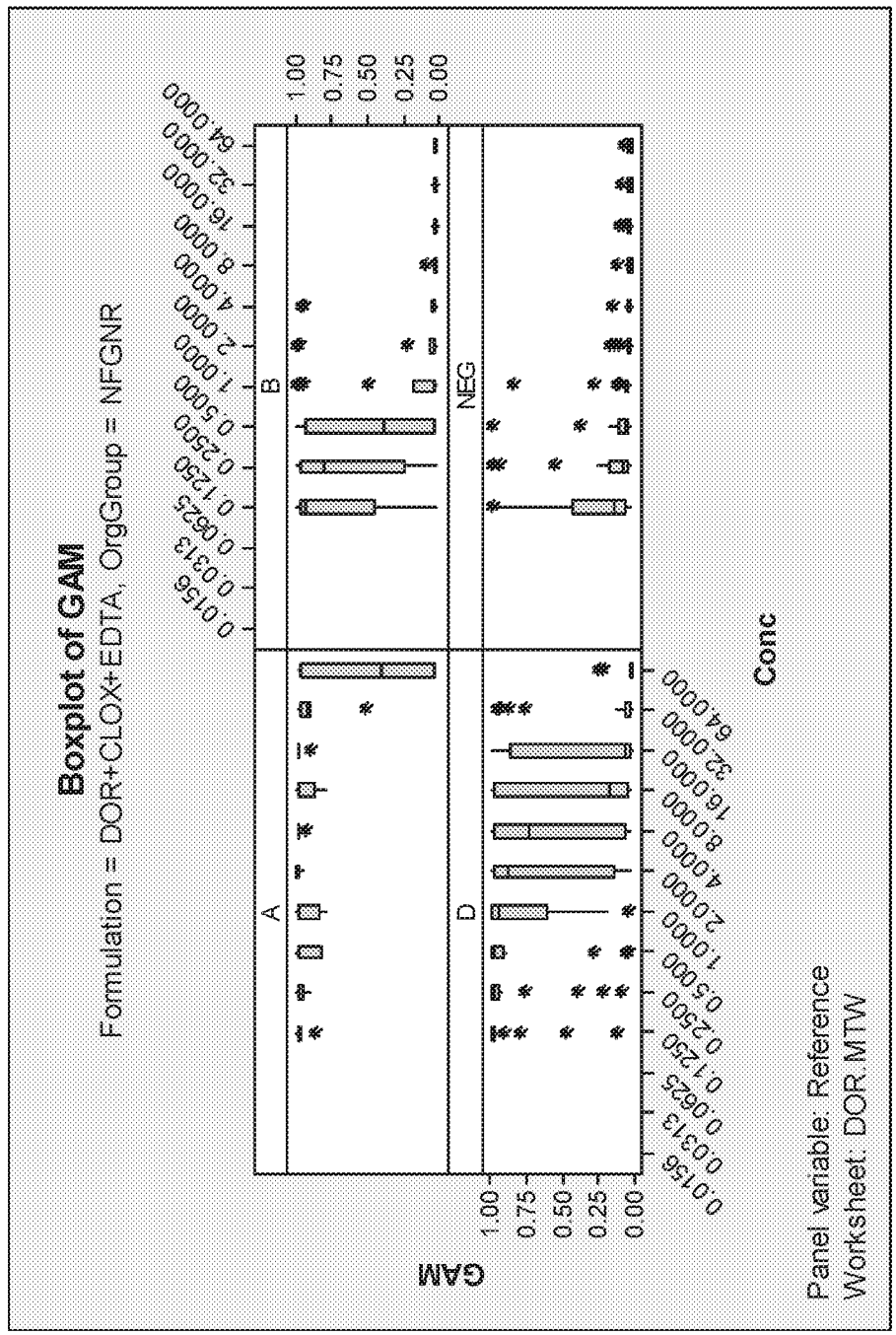
FIG. 16 shows a boxplot of DOR/CLOX/EDTA GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, EDTA at 0.25 mg/ml, and DOR over a range of concentrations of about 0.0156 µg/ml to about 64 µg/ml (FIG. 16).

Figure 17:
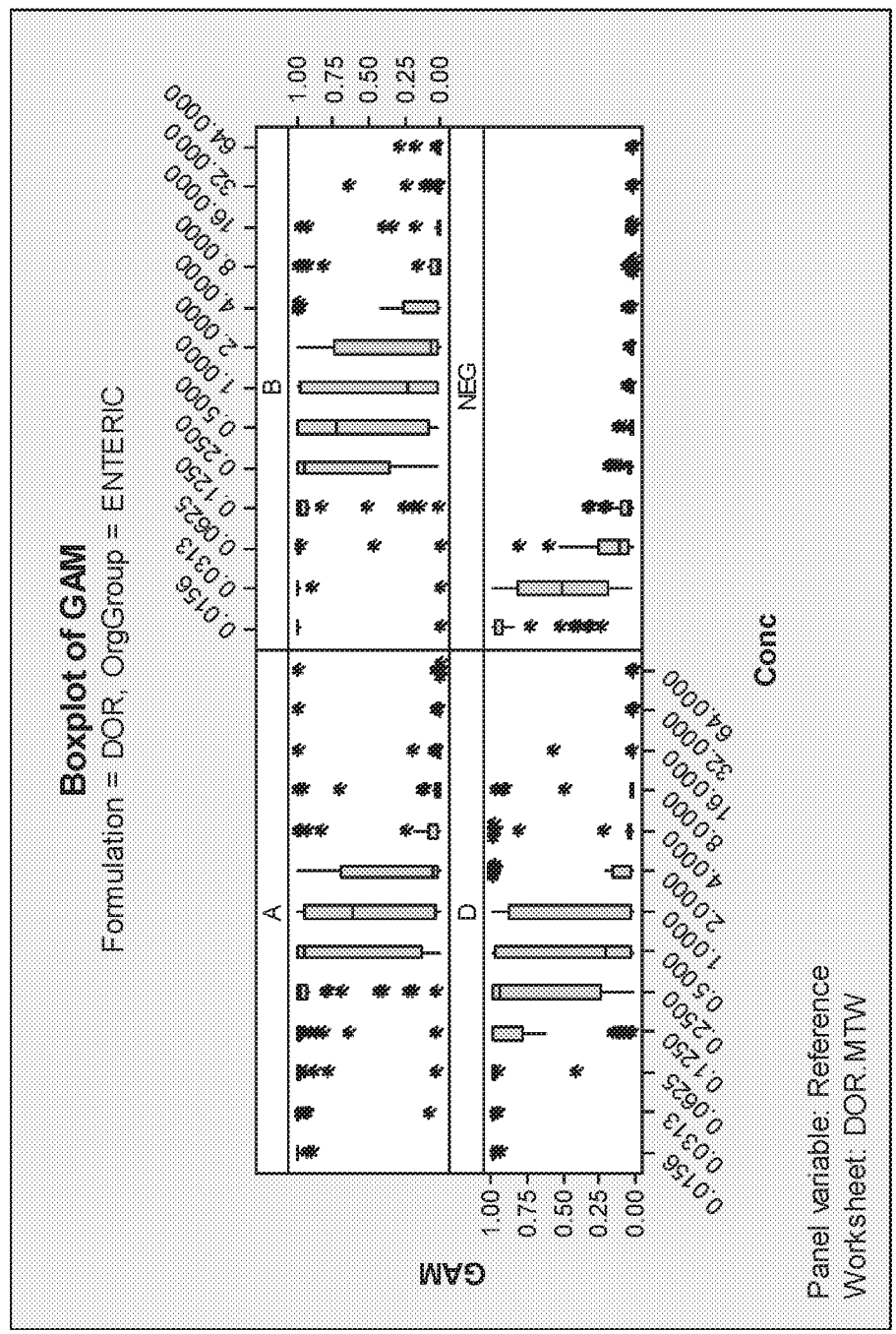
FIG. 17 shows a boxplot of DOR GAM data for enteric bacteria expressing either Class A, Class B or Class D carbapenemase.

In some embodiments, the detection tests can comprise a plurality of wells comprising enteric bacteria, and DOR over a range of concentrations of about 0.0156 µg/ml to about 64 µg/ml (FIG. 17).

Figure 18:
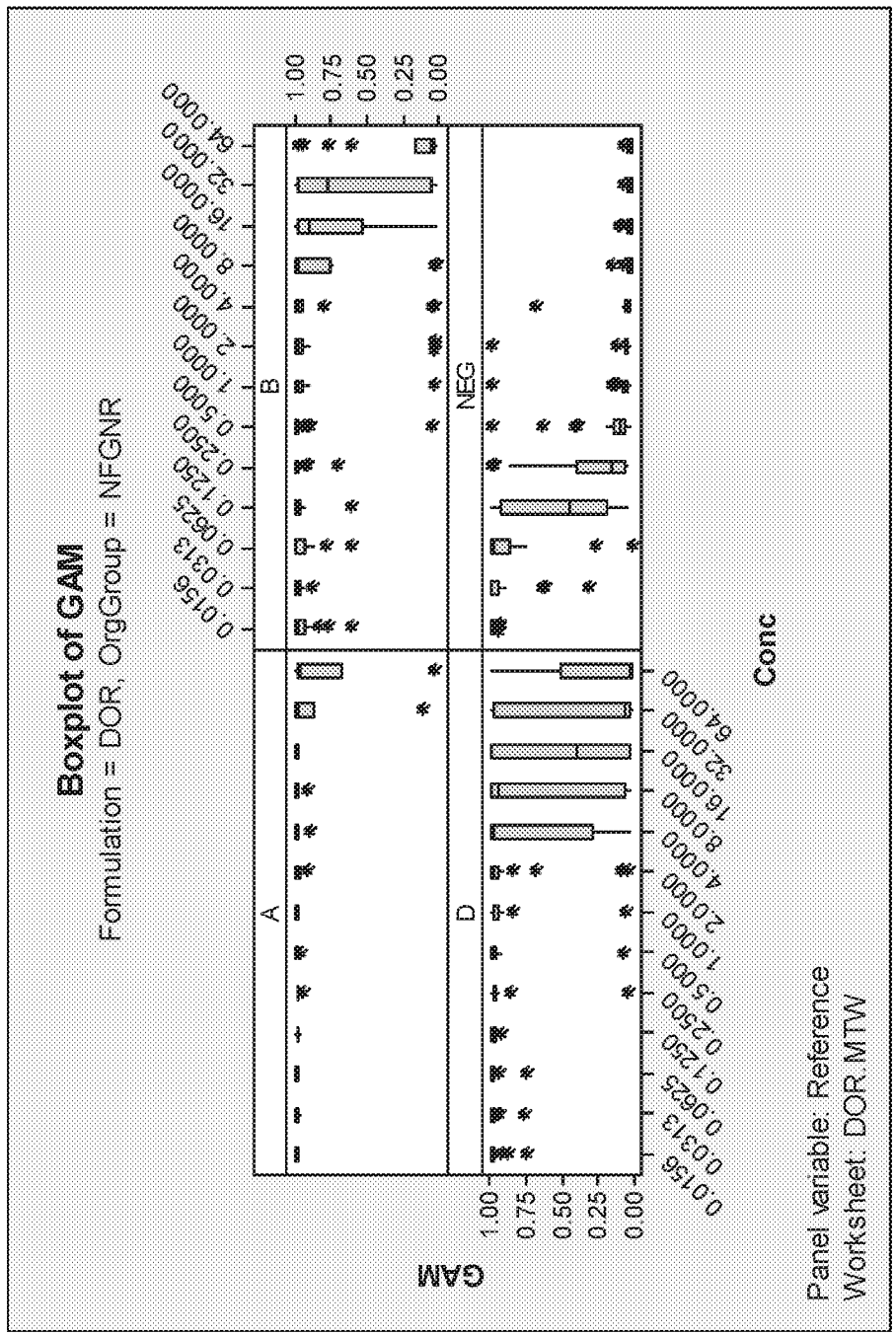
FIG. 18 shows a boxplot of DOR GAM data for non-fermenting gram negative rod bacteria expressing either Class A, Class B or Class D carbapenemase.

In some embodiments, the detection tests can comprise a plurality of wells comprising non-fermenting bacteria, and DOR over a range of concentrations of about 0.0156 µg/ml to about 64 µg/ml (FIG. 18).

Figure 19:
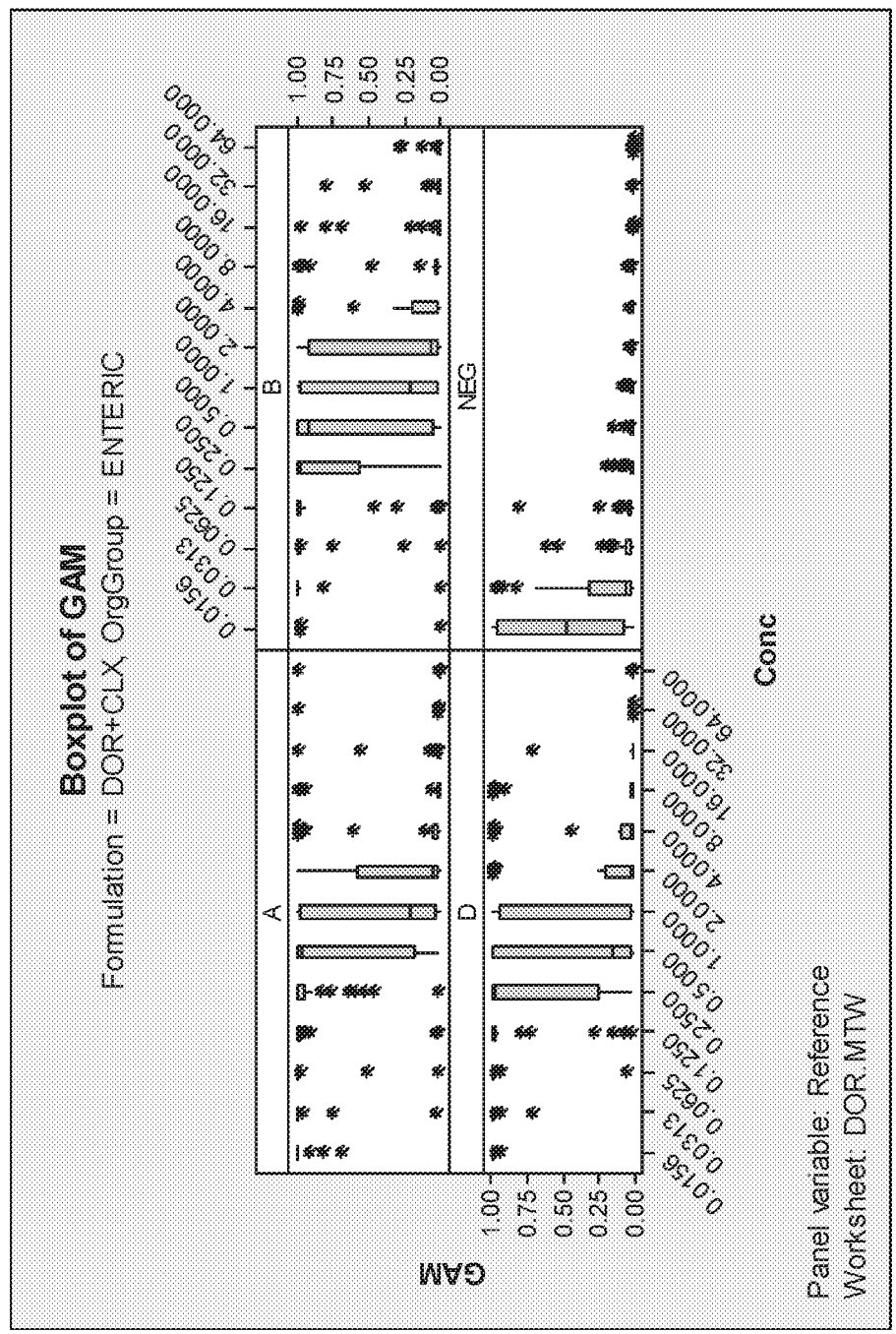
FIG. 19 shows boxplot of DOR/CLOX GAM data for enteric bacteria expressing either Class A, Class B or Class D carbapenemase.

In some embodiments, the detection tests can comprise a plurality of wells comprising enteric bacteria, CLOX at 0.1 mg/ml, and DOR over a range of concentrations of about 0.0156 µg/ml to about 64 µg/ml (FIG. 19).

Figure 20:
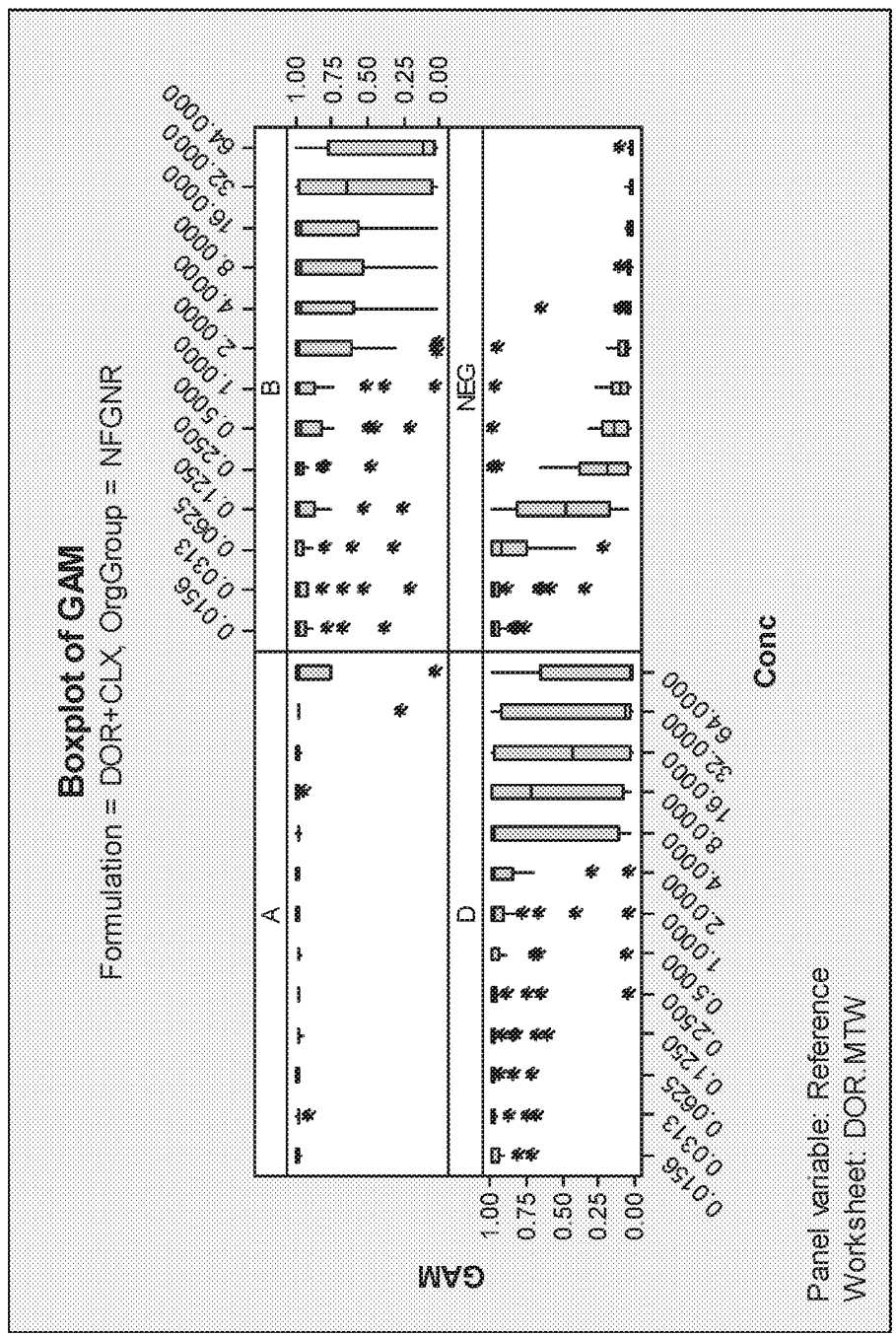
FIG. 20 shows a boxplot of DOR/CLOX GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, and DOR over a range of concentrations of about 0.0156 µg/ml to about 64 µg/ml (FIG. 20).

Figure 21:
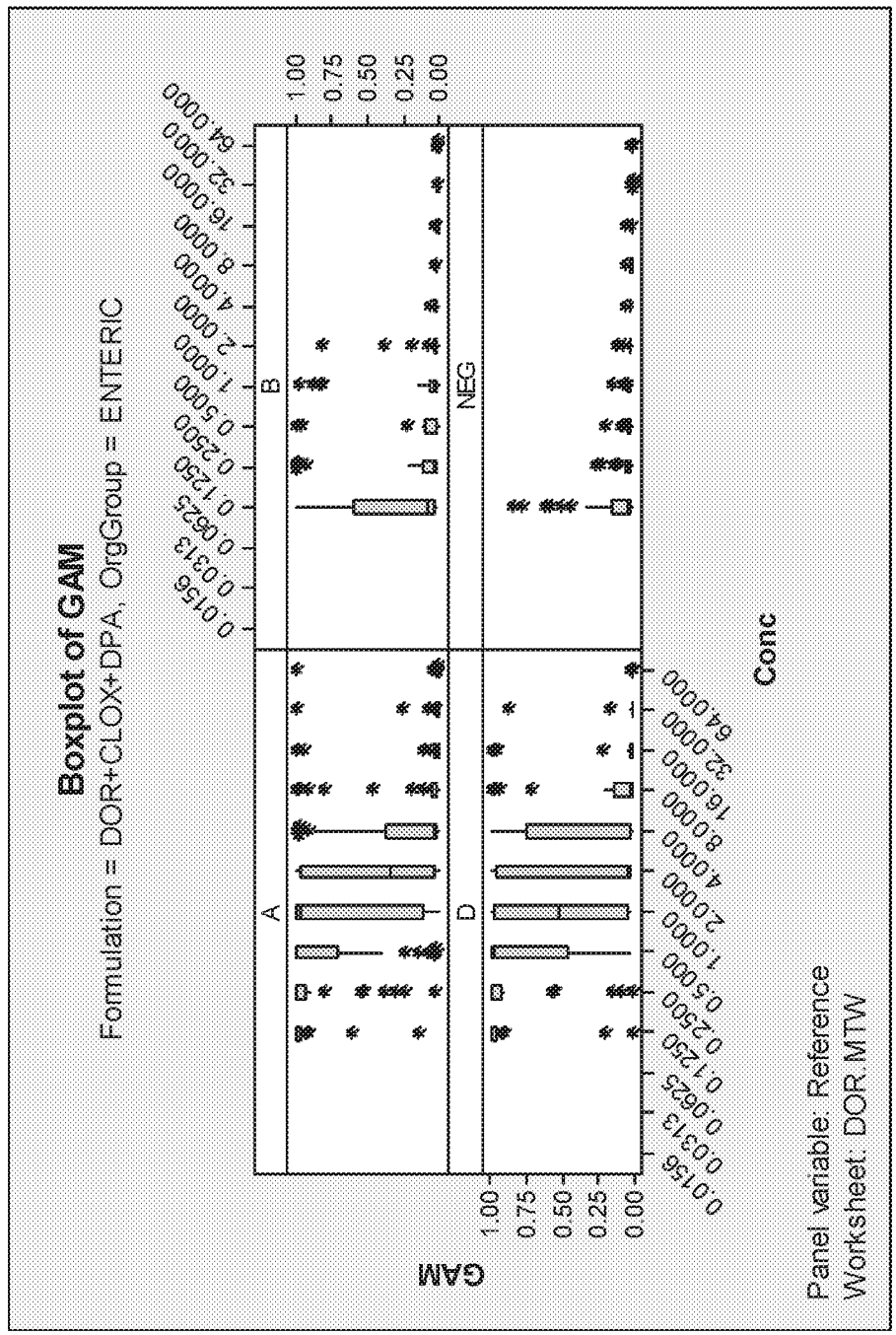
FIG. 21 shows a boxplot of DOR/CLOX/DPA GAM data for enteric bacteria expressing either Class A, Class B or Class D carbapenemase.

In some embodiments, the detection tests can comprise a plurality of wells comprising enteric bacteria, CLOX at 0.1 mg/ml, DPA at 0.18 mg/ml, and DOR over a range of concentrations of about 0.0156 µg/ml to about 64 µg/ml (FIG. 21).

Figure 22:
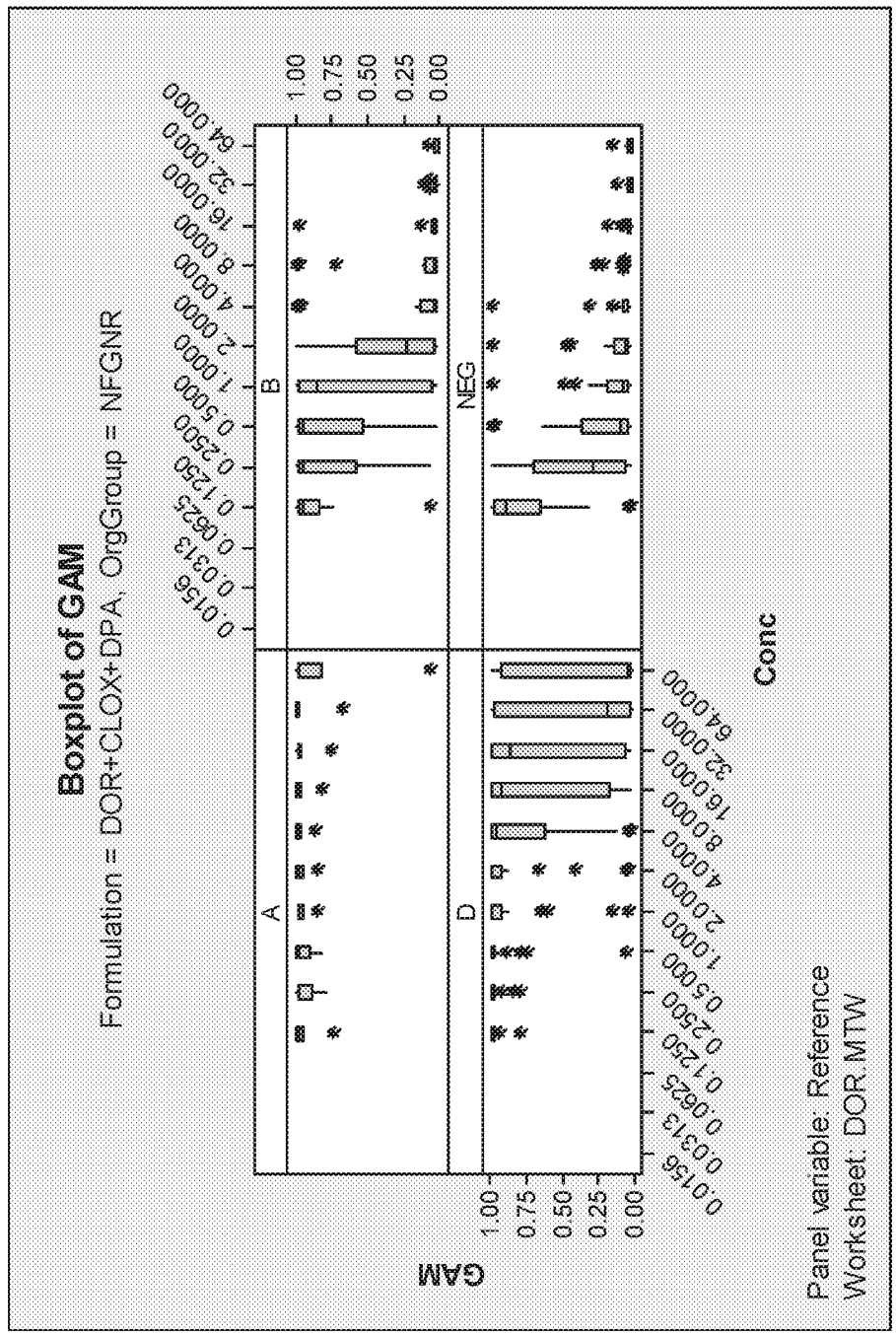
FIG. 22 shows a boxplot of DOR/CLOX/DPA GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, DPA at 0.18 mg/ml, and DOR over a range of concentrations of about 0.0156 µg/ml to about 64 µg/ml (FIG. 22).

Figure 23:
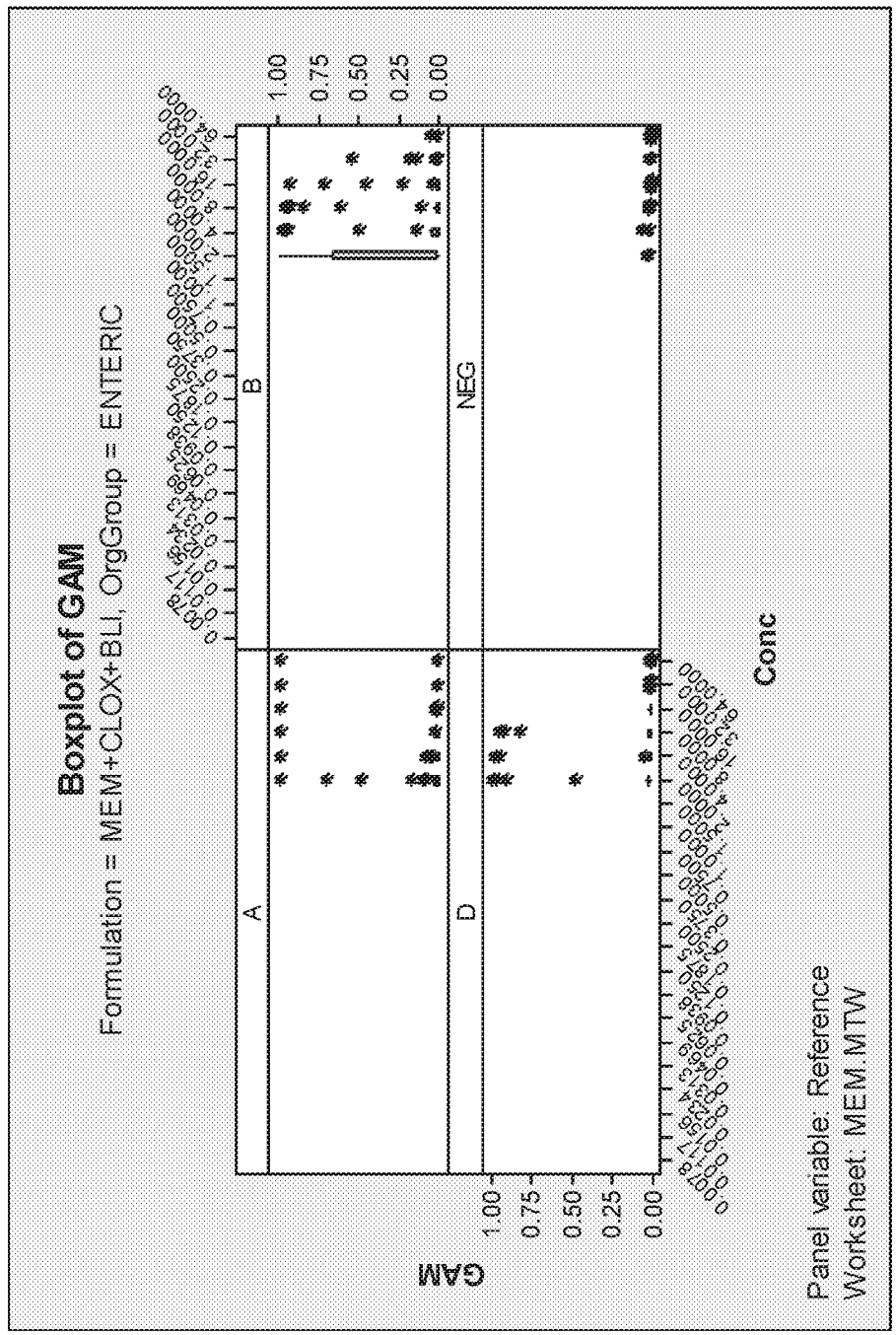
FIG. 23 shows a boxplot of MEM/CLOX/BLI GAM data for enteric bacteria expressing either Class A, Class B or Class D carbapenemase.

In some embodiments, the detection tests can comprise a plurality of wells comprising enteric bacteria, CLOX at 0.1 mg/ml, BLI at 5 µg/ml, and MEM over a range of concentrations of about 0.0078 µg/ml to about 64 µg/ml (FIG. 23).

Figure 24:
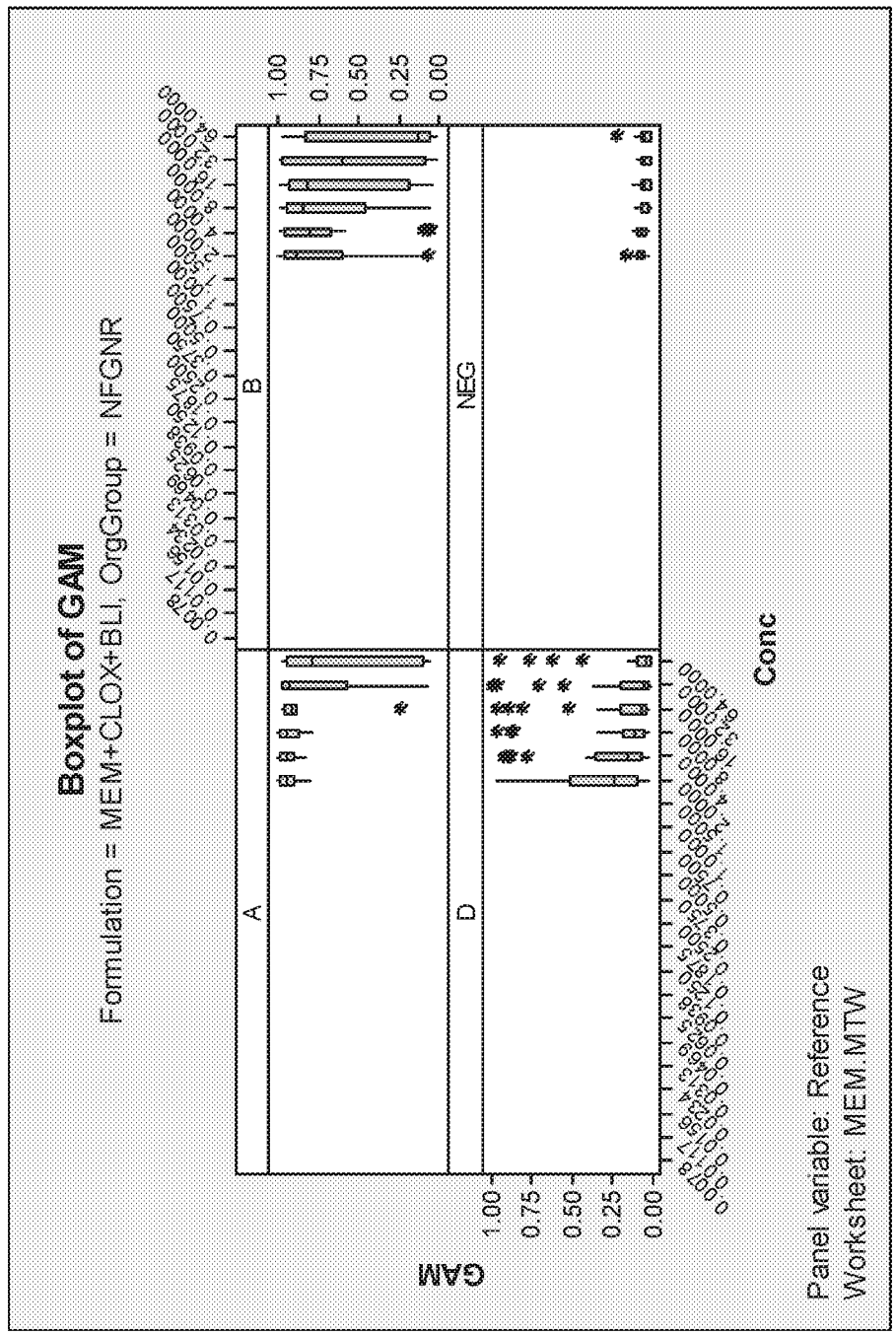
FIG. 24 shows a boxplot of MEM/CLOX/BLI GAM data for non-fermenting gram negative rod bacteria expressing either Class A, Class B or Class D carbapenemase.

In some embodiments, the detection tests can comprise a plurality of wells comprising non-fermenting bacteria, CLOX at 0.1 mg/ml, BLI at 5 µg/ml, and MEM over a range of concentrations of about 0.0078 µg/ml to about 64 µg/ml (FIG. 24).

In some embodiments, the detection tests can comprise a plurality of wells comprising enteric bacteria, CLOX at 0.1 mg/ml, and MEM over a range of concentrations of about 0.0156 µg/ml to about 64 µg/ml (FIG. 31).

In the detection tests, based on whether the bacteria grow or do not grow in the presence of a specific concentration of antibiotic, a determination of whether or not the bacteria are sensitive to the one or more antibiotics provided herein is achieved. If the bacteria are insensitive to the one or more antibiotics, an identification of one or more classes of carbapenemases expressed by bacteria that confer insensitivity to the antibiotics is achieved by using one or more carbapenemase inhibitors or differentiators provided herein.

Non-limiting examples (Example 1-Example 4) of detection tests to identify the expression by enteric or non-fermenting bacteria of one or more Ambler classes of carbapenemases are provided. The determination of whether the sample comprises enteric or non-fermenting bacteria can be made by methods known in the art, for example, spot Oxidase Test, MALDI-TOF and biochemical tests, including the Phoenix ID system. The concentrations of the antibiotics and inhibitors disclosed in the following examples are exemplary and non-limiting. Other concentrations or ranges of concentrations which are acceptable are disclosed in the instant disclosure, including the figures.

In some embodiments, BD Phoenix™ CPO Detect comprises a well (or optionally several identical wells) comprising an input sample comprising one or more bacteria, one or more detection reagents, and one or more antibiotics with/without one or more carbapenemase inhibitors. In some embodiments, a well comprises one of the combinations disclosed in the Table 0.1 below comprising of one or more antibiotics without/without one or more carbapenemase inhibitors.

TABLE 0.1

Combinations of one or more antibiotics without or without one or more carbapenemase inhibitors

| Combination | Components |
|---|---|
| 1 | DOR |
| 2 | DOR/CLOX |
| 3 | DOR/CLOX/AVI |
| 4 | DOR/CLOX/DPA |
| 5 | DOR/CLOX/EDTA |
| 6 | MEM/CLOX |
| 7 | MEM/CLOX/BLI |
| 8 | MEM/CLOX/DPA |
| 9 | MEM/CLOX/RPX |
| 10 | TEM/EDTA |

In any of the Combinations 1-10 provided in Table 0.1, concentration of CLOX is, or is about, 2.5 µg/ml to 40000 µg/ml, or the concentration of CLOX is, or is about, 20 µg/ml to 500 µg/ml. In some embodiments, the concentration of CLOX is, or is about, 20 µg/ml to 150 µg/ml, the concentration of CLOX is, or is about, 150 µg/ml to 250 µg/ml, the concentration of CLOX is, or is about, 250 µg/ml to 350 µg/ml, or the concentration of CLOX is, or is about, 350 µg/ml to 500 µg/ml, with some embodiments having a concentration that is, or is about, 100 µg/ml. In some embodiments, the concentration of CLOX is, or is about, 20, 30, 40, 50, 60, 70, 80, 90, 100, 150, 200, 250, 300, 350, 400, 450, 500, 1000, 5000, 10,000, or 40,000 µg/ml, or within a range defined by any two of the aforementioned values.

In any of the Combinations 1-10 provided in Table 0.1, the concentration of AVI is, or is about, 0.5 µg/ml to 20 µg/ml. In some embodiments, the concentration of AVI is, or is about, 0.5 µg/ml to 5 µg/ml, the concentration of AVI is, or is about, 5 µg/ml to 10 µg/ml, the concentration of AVI is, or is about, 10 µg/ml to 15 µg/ml, or the concentration of AVI is, or is about, 15 µg/ml to 10 µg/ml, with some embodiments having a concentration that is, or is about, 4 µg/ml. In some embodiments, the concentration of AVI is, or is about, 0.5, 1, 1.5, 2, 2.5, 3, 3.5, 4, 4.5, 5, 7.5, 10, 12.5, 15, 17.5, or 20 µg/ml, or within a range defined by any two of the aforementioned values.

In any of the Combinations 1-10 provided in Table 0.1, the concentration of BLI-489 is, or is about, 1 µg/ml to 25 µg/ml. In some embodiments, the concentration of BLI-489 is, or is about, 1 µg/ml to 5 µg/ml, the concentration of BLI-489 is, or is about, 5 µg/ml to 10 µg/ml, the concentration of BLI-489 is, or is about, 10 µg/ml to 17.5 µg/ml, or the concentration of BLI-489 is, or is about, 17.5 µg/ml to 25 µg/ml, with some embodiments having a concentration that is, or is about, 5 µg/ml. In some embodiments, the concentration of BLI-489 is, or is about, 1, 2.5, 3, 3.5, 4, 4.5, 5, 7.5, 10, 12.5, 15, 17.5, 20, 22.5, or 25 µg/ml, or within a range defined by any two of the aforementioned values.

In any of the Combinations 1-10 provided in Table 0.1, the concentration of DPA is, or is about, 35 µg/ml to 900 µg/ml. In some embodiments, the concentration of DPA is, or is about, 35 µg/ml to 150 µg/ml, the concentration of DPA is, or is about, 150 µg/ml to 300 µg/ml, the concentration of DPA is, or is about, 300 µg/ml to 650 µg/ml, or the concentration of DPA is, or is about, 650 µg/ml to 900 µg/ml, with some embodiments having a concentration that is, or is about, 178 µg/ml. In some embodiments, the concentration of DPA is, or is about, 35, 70, 140, 178, 200, 280, 350, 450, 560, 640, 730, 820, or 900 µg/ml, or within a range defined by any two of the aforementioned values.

In any of the Combinations 1-10 provided in Table 0.1, the concentration of EDTA is, or is about, 50 µg/ml to 1250 µg/ml. In some embodiments, the concentration of EDTA is, or is about, 50 µg/ml to 250 µg/ml, the concentration of EDTA is, or is about, 250 µg/ml to 500 µg/ml, the concentration of EDTA is, or is about, 500 µg/ml to 750 µg/ml, or the concentration of EDTA is, or is about, 750 µg/ml to 1250 µg/ml, with some embodiments having a concentration that is, or is about, 250 µg/ml. In some embodiments, the concentration of EDTA is, or is about, 50, 75, 150, 200, 250, 300, 350, 500, 600, 750, 1000, or 1250 µg/ml, or within a range defined by any two of the aforementioned values.

In any of the Combinations 1-10 provided in Table 0.1, the concentration of RPX7009 is, or is about, 1.5 µg/ml to 40 µg/ml. In some embodiments, the concentration of RPX7009 is, or is about, 1.5 µg/ml to 3 µg/ml, the concentration of RPX7009 is, or is about, 3 µg/ml to 15 µg/ml, the concentration of RPX7009 is, or is about, 15 µg/ml to 25 µg/ml, or the concentration of RPX7009 is, or is about, about 25 µg/ml to 40 µg/ml, with some embodiments having a concentration that is, or is about, 8 µg/ml. In some embodiments, the concentration range of RPX7009 is, or is about, 3, 3.5, 4, 4.5, 5, 5.5, 6, 6.5, 7, 7.5, 8, 8.5, 9, 9.5, 10, 10.5, 11, 11.5, 12, 12.5, 13, 13.5 14, 14.5 or 15 µg/ml, or within a range defined by any two of the aforementioned values.

In Combination 1, the concentration of DOR is, or is about, 0.0625 µg/ml to 0.25 µg/ml. In some embodiments, the concentration of DOR is, or is about, 0.0125 µg/ml to 1.25 µg/ml, the concentration of DOR is, or is about, 0.0625 µg/ml to 0.0825 µg/ml, the concentration of DOR is, or is about, 0.0825 µg/ml to 0.125 µg/ml, the concentration of DOR is, or is about, 0.125 µg/ml to 0.175 µg/ml, or the concentration of DOR is, or is about, 0.175 µg/ml to 0.25 µg/ml. In some embodiments, the concentration of DOR is, or is about, 0.0125, 0.0625, 0.07, 0.075, 0.08, 0.085, 0.09, 0.095, 0.1, 0.125, 0.15, 0.175, 0.2, 0.225, 0.25, 0.5, 0.75, 1.0, or 1.25 µg/ml, or within a range defined by any two of the aforementioned values.

In Combination 2, the concentration of DOR is, or is about, 0.5 µg/ml to 4 µg/ml. In some embodiments, the concentration of DOR is, or is about, 0.1 µg/ml to 40 µg/ml, the concentration of DOR is, or is about, 0.1 µg/ml to 10 µg/ml, the concentration of DOR is, or is about, 0.2 µg/ml to 20 µg/ml, the concentration of DOR is, or is about, 0.5 µg/ml to 4 µg/ml, the concentration of DOR is, or is about, 0.5 µg/ml to 1 µg/ml, the concentration of DOR is, or is about, 1 µg/ml to 2 µg/ml, the concentration of DOR is, or is about, 2 µg/ml to 3 µg/ml, or the concentration of DOR is, or is about, 3 µg/ml to 4 µg/ml. In some embodiments, the concentration of DOR is, or is about, 0.1, 0.15, 0.2, 0.25, 0.5, 1, 1.25, 1.5, 1.75, 2, 2.25, 2.5, 2.75, 3, 3.25, 3.5, 3.75, 4, 5, 6, 7, 8, 9, 10, 15, 20, 30, or 40 µg/ml, or within a range defined by any two of the aforementioned values.

In Combination 3, the concentration of DOR is, or is about, 0.03125 µg/ml to 16 µg/ml, or 0.02 µg/ml to 600 µg/ml. In some embodiments, the concentration of DOR is, or is about, 0.03126 µg/ml to 1 µg/ml, the concentration of DOR is, or is about, 1 µg/ml to 4 µg/ml, the concentration of DOR is, or is about, 4 µg/ml to 8 µg/ml, or the concentration of DOR is, or is about, 8 µg/ml to 16 µg/ml. In some embodiments, the concentration of DOR is, or is about, 0.03125, 0.0625, 0.1, 0.5, 0.75, 1, 2, 4, 5, 6, 8, 10, 12, 14, 16, 24, 32, 40, 48, 56, 60, 80 or 100 µg/ml, or within a range defined by any two of the aforementioned values. In some embodiments, the concentration of DOR is, or is about 0.006 µg/ml to 0.6 µg/ml. In some embodiments, the concentration of DOR is, or is about, 0.03125 µg/ml to 0.0625 µg/ml, the concentration of DOR is, or is about, 0.015 µg/ml to 0.24 µg/ml, the concentration of DOR is, or is about, 0.0625 µg/ml to 0.0775 µg/ml, the concentration of DOR is, or is about, 0.0775 µg/ml to 0.1 µg/ml, or the concentration of DOR is, or is about, 0.1 µg/ml to 0.125 µg/ml. In some embodiments, the concentration of DOR is, or is about, 0.03, 0.03125, 0.04, 0.05, 0.06, 0.07, 0.08, 0.09, 0.1, 0.11, 0.12, 0.125, 0.15, 0.2, 0.4, 0.5, or 0.6 µg/ml, or within a range defined by any two of the aforementioned values.

In Combination 4, the concentration of DOR is, or is about, 0.5 µg/ml to 2 µg/ml. In some embodiments, the concentration of DOR is, or is about, 0.1 µg/ml to 10 µg/ml, the concentration of DOR is, or is about, 0.25 µg/ml to 4 µg/ml the concentration of DOR is, or is about, 0.5 µg/ml to 0.75 µg/ml, the concentration of DOR is, or is about, 0.75 µg/ml to 1 µg/ml, the concentration of DOR is, or is about, 1 µg/ml to 1.5 µg/ml, or the concentration of DOR is, or is about, 1.5 µg/ml to 2 µg/ml. In some embodiments, the concentration of DOR is, or is about, 0.5, 0.55, 0.6, 0.65, 0.7, 0.75, 1, 1.25, 1.5, 1.75, or 2 µg/ml, or within a range defined by any two of the aforementioned values.

In Combination 5, the concentration of DOR is, or is about, 0.03125 µg/ml to 0.125 µg/ml. In some embodiments, the concentration of DOR is, or is about, 0.03125 µg/ml to 0.0625 µg/ml, the concentration of DOR is, or is about, 0.0625 µg/ml to 0.0775 µg/ml, the concentration of DOR is, or is about, 0.0775 µg/ml to 0.1 µg/ml, or the concentration of DOR is, or is about, 0.1 µg/ml to 0.125 µg/ml. In some embodiments, the concentration of DOR is, or is about 0.006 µg/ml to 0.6 µg/ml. In some embodiments, the concentration of DOR is, or is about, 0.015 µg/ml to 0.24 µg/ml. In some embodiments, the concentration of DOR is, or is about, 0.006, 0.01, 0.015, 0.03, 0.03125, 0.04, 0.05, 0.06, 0.0625, 0.07, 0.08, 0.09, 0.1, 0.115, 0.12, 0.125, 0.15 0.2. 0.4, 0.5, or 0.6 µg/ml, or within a range defined by any two of the aforementioned values.

In Combination 6, the concentration of MEM is, or is about, 0.03125 µg/ml to 1 µg/ml. In some embodiments, the concentration of MEM is, or is about, 0.0125 µg/ml to 5 µg/ml, the concentration of MEM is, or is about, 0.03125 µg/ml to 0.0625 µg/ml, the concentration of MEM is, or is about, 0.0625 µg/ml to 0.125 µg/ml, the concentration of MEM is, or is about, 0.125 µg/ml to 0.5 µg/ml, the concentration of MEM is, or is about, 0.125 µg/ml to 2 µg/ml, or the concentration of MEM is, or is about, 0.5 µg/ml to 1 µg/ml. In some embodiments, the concentration of MEM is, or is about, 0.0125, 0.03, 0.03125, 0.0625, 0.075, 0.1, 0.125, 0.25, 0.5, 0.6, 0.625, 0.7, 0.725, 0.8, 0.875, 0.9, 1, 1.5, 2, 2.5, or 5 µg/ml, or within a range defined by any two of the aforementioned values. In some embodiments, the concentration of MEM is, or is about 0.006 µg/ml to 0.6 µg/ml. In some embodiments, the concentration of MEM is, or is about, 0.03125 µg/ml to 0.0625 µg/ml, the concentration of MEM is, or is about, 0.015 µg/ml to 0.24 µg/ml, the concentration of MEM is, or is about, 0.0625 µg/ml to 0.0775 µg/ml, the concentration of MEM is, or is about, 0.0775 µg/ml to 0.1 µg/ml, or the concentration of MEM is, or is about, 0.1 µg/ml to 0.125 µg/ml. In some embodiments, the concentration of MEM is, or is about, 0.03, 0.03125, 0.04, 0.05, 0.06, 0.07, 0.08, 0.09, 0.1, 0.11, 0.12, 0.125, 0.15, 0.2, 0.4, 0.5, or 0.6 µg/ml, or within a range defined by any two of the aforementioned values.

In Combination 7, the concentration of MEM is, or is about, 2 µg/ml to 8 µg/ml. In some embodiments, the concentration of MEM is, or is about, 0.4 µg/ml to 40 µg/ml, the concentration of MEM is, or is about, 1 µg/ml to 16 µg/ml, the concentration of MEM is, or is about, 2 µg/ml to 4 µg/ml, the concentration of MEM is, or is about, 4 µg/ml to 6 µg/ml, the concentration of MEM is, or is about, 6 µg/ml to 7.5 µg/ml, or the concentration of MEM is, or is about, 7.5 µg/ml to 8 µg/ml. In some embodiments, the concentration of MEM is, or is about, 0.4, 1, 2, 2.5, 3, 3.5, 4, 4.5, 5, 5.5, 6, 6.5, 7, 7.5, 8, 12, 16, 20, 25, 30, 35, or 40 µg/ml, or within a range defined by any two of the aforementioned values.

In Combination 8, the concentration of MEM is, or is about, 0.03125 µg/ml to 0.125 µg/ml. In some embodiments, the concentration of MEM is, or is about, 0.03125 µg/ml to 0.0625 µg/ml, the concentration of MEM is, or is about, 0.0625 µg/ml to 0.0775 µg/ml, the concentration of MEM is, or is about, 0.0775 µg/ml to 0.1 µg/ml, or the concentration of MEM is, or is about, 0.1 µg/ml to 0.125 µg/ml. In some embodiments, the concentration of MEM is, or is about 0.006 µg/ml to 0.6 µg/ml. In some embodiments, the concentration of MEM is, or is about, 0.015 µg/ml to 0.24 µg/ml. In some embodiments, the concentration of MEM is, or is about, 0.006, 0.01, 0.015, 0.03, 0.03125, 0.04, 0.05, 0.06, 0.07, 0.08, 0.09, 0.1, 0.11, 0.12, 0.125, 0.15, 0.2, 0.4, 0.5, or 0.6 µg/ml, or within a range defined by any two of the aforementioned values.

In Combination 9, the concentration of MEM is, or is about, 0.015625 µg/ml to 0.125 µg/ml. In some embodiments, the concentration of MEM is, or is about, 0.03125 µg/ml to 0.0625 µg/ml, the concentration of MEM is, or is about, 0.0625 µg/ml to 0.0775 µg/ml, the concentration of MEM is, or is about, 0.0775 µg/ml to 0.1 µg/ml, or the concentration of MEM is, or is about, 0.1 µg/ml to 0.125 µg/ml. In some embodiments, the concentration of MEM is, or is about 0.006 µg/ml to 0.6 µg/ml, the concentration of MEM is, or is about, 0.015 µg/ml to 0.24 µg/ml, the concentration of MEM is, or is about 0.003 µg/ml to 0.3 µg/ml, or the concentration of MEM is, or is about, 0.0075 µg/ml to 0.12 µg/ml. In some embodiments, the concentration of MEM is, or is about, 0.003, 0.0075, 0.01, 0.015, 0.01, 0.015625, 0.02, 0.03, 0.04, 0.05, 0.06, 0.07, 0.08, 0.09, 0.1, 0.12, 0.125, 0.15, 0.2, 0.3, 0.4, 0.5, or 0.6 µg/ml, or within a range defined by any two of the aforementioned values.

In Combination 10, the concentration of TEM is, or is about, 32 µg/ml to 128 µg/ml. In some embodiments, the concentration of TEM is, or is about, 24 µg/ml to 128 µg/ml, the concentration of TEM is, or is about, 32 µg/ml to 75 µg/ml the concentration of TEM is, or is about, 32 µg/ml to 50 µg/ml, the concentration of TEM is, or is about, 50 µg/ml to 75 µg/ml, the concentration of TEM is, or is about, 75 µg/ml to 100 µg/ml, or the concentration of TEM is, or is about, 100 µg/ml to 128 µg/ml. In some embodiments, the concentration of TEM is, or is about, 32, 40, 50, 60, 64, 70, 75, 80, 90, 100, 110, 120, or 128 µg/ml, or within a range defined by any two of the aforementioned values.

The algorithms provided herein are exemplary and non-limiting and one of ordinary skill in the art can design an algorithm based on any combination of Boxes provided in the algorithms described herein in order to obtain the information desired in regard to CPO detection and/or Ambler classification of carbapenemase.

For example, in some embodiments, as provided in Example 10.1 to Example 10.4 wherein each "Box" in the algorithm represents a test site(s) (e.g., well, or optionally the average of several identical wells) of the detection tests provided herein comprising an input sample comprising one or more bacteria, one or more detection reagents, and one or more antibiotics with/without one or more carbapenemase inhibitors, CPO detection and/or classification wells of algorithms for enteric bacteria can be permuted and/or combined with CPO detection and/or classification wells of algorithms for non-fermenting bacteria to achieve detection of CPO enteric bacteria, CPO non-fermenting bacteria or both, and/or Ambler classification of enteric bacteria, non-fermenting bacteria or both.

In some embodiments, a well comprises one of the combinations comprising of one or more antibiotics without/ without one or more carbapenemase inhibitors disclosed in the Table 0.1. In some embodiments, the test comprises at least 2 wells, wherein one well is for the detection of CPO enteric bacteria and one well is for the detection of CPO non-fermenting bacteria (e.g., FIG. 36).

Figure 37:
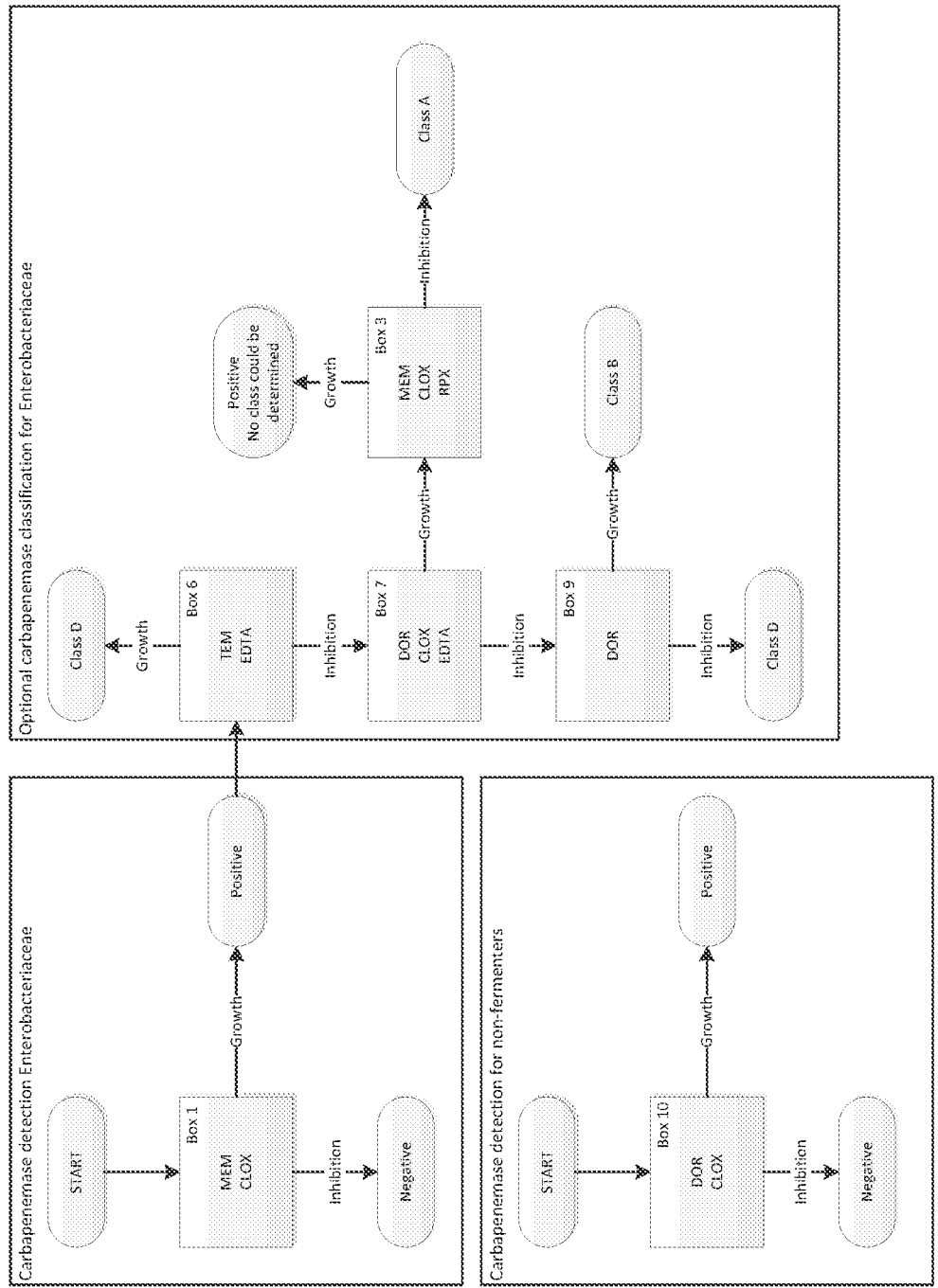
FIG. 37 shows a flowchart of an embodiment of an algorithm for Enterobacteriaceae and nonfermenters and classification of Enterobacteriaceae.

In some embodiments, the test comprises at least 6 wells, wherein one well is for the detection of CPO enteric bacteria, one well is for the detection of CPO non-fermenting bacteria, and 4 wells are for Ambler classification of the carbapenamase produced by enteric bacteria (e.g., FIG. 37). Thus, in some embodiments, at least 4 wells allow for Ambler classification of the carbapenamase produced by enteric bacteria (e.g., FIG. 37). In some embodiments, the number of wells used for Ambler classification of the carbapenamase produced by enteric bacteria is 2 to 5. In some embodiments, the number of wells used for Ambler classification of the carbapenamase produced by enteric bacteria is 2, 3, 4, 5 or more.

Figure 38:
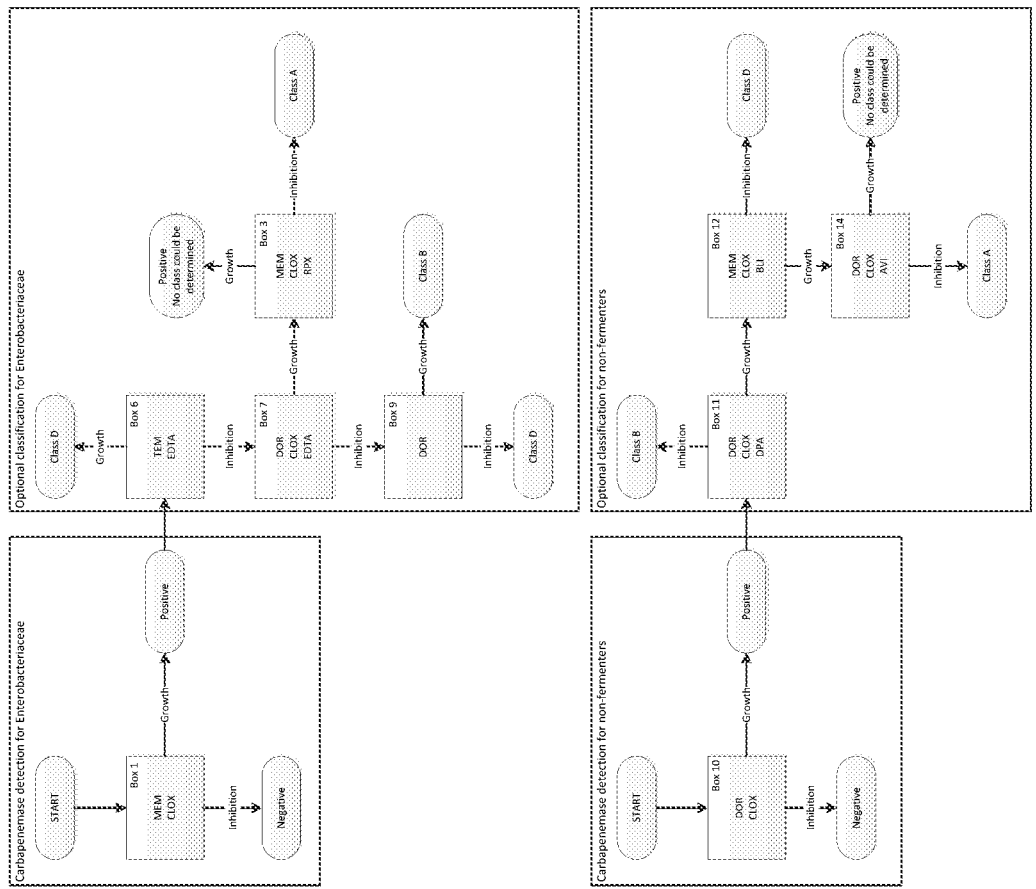
FIG. 38 shows a flowchart of an embodiment of an algorithm for Enterobacteriaceae and nonfermenters and classification of Enterobacteriaceae and nonfermenters.

In some embodiments, the test comprises at least 9 wells, wherein one well is for the detection of CPO enteric bacteria, one well is for the detection of CPO non-fermenting bacteria, 4 wells are for Ambler classification of the carbapenamase produced by enteric bacteria, and 3 wells are for Ambler classification of the carbapenamase produced by non-fermenting bacteria (e.g., FIG. 38). Thus, in some embodiments, at least 4 wells allow for Ambler classification of the carbapenamase produced by enteric bacteria, at least 3 wells allow for Ambler classification of the carbapenamase produced by non-fermenting bacteria, and at least 7 wells allow for Ambler classification of the carbapenamase produced by enteric and non-fermenting bacteria (e.g., FIG. 38). In some embodiments, the number of wells used for Ambler classification of the carbapenamase produced by enteric bacteria is 2 to 5 and the number of wells used for Ambler classification of the carbapenamase produced by non-fermenting bacteria is 2 to 4. In some embodiments, the number of wells used for Ambler classification of the carbapenamase produced by enteric bacteria is 2, 3, 4, 5 or more, and the number of wells used for Ambler classification of the carbapenamase produced by non-fermenting bacteria is 2, 3, 4, 5 or more. In some embodiments, the number of wells used for Ambler classification of the carbapenamase produced by enteric and non-fermenting bacteria is 4 to 9. In some embodiments, the number of wells used for Ambler classification of the carbapenamase produced by enteric and non-fermenting bacteria is 4, 5, 6, 7, 8, 9 or more.

Figure 39:
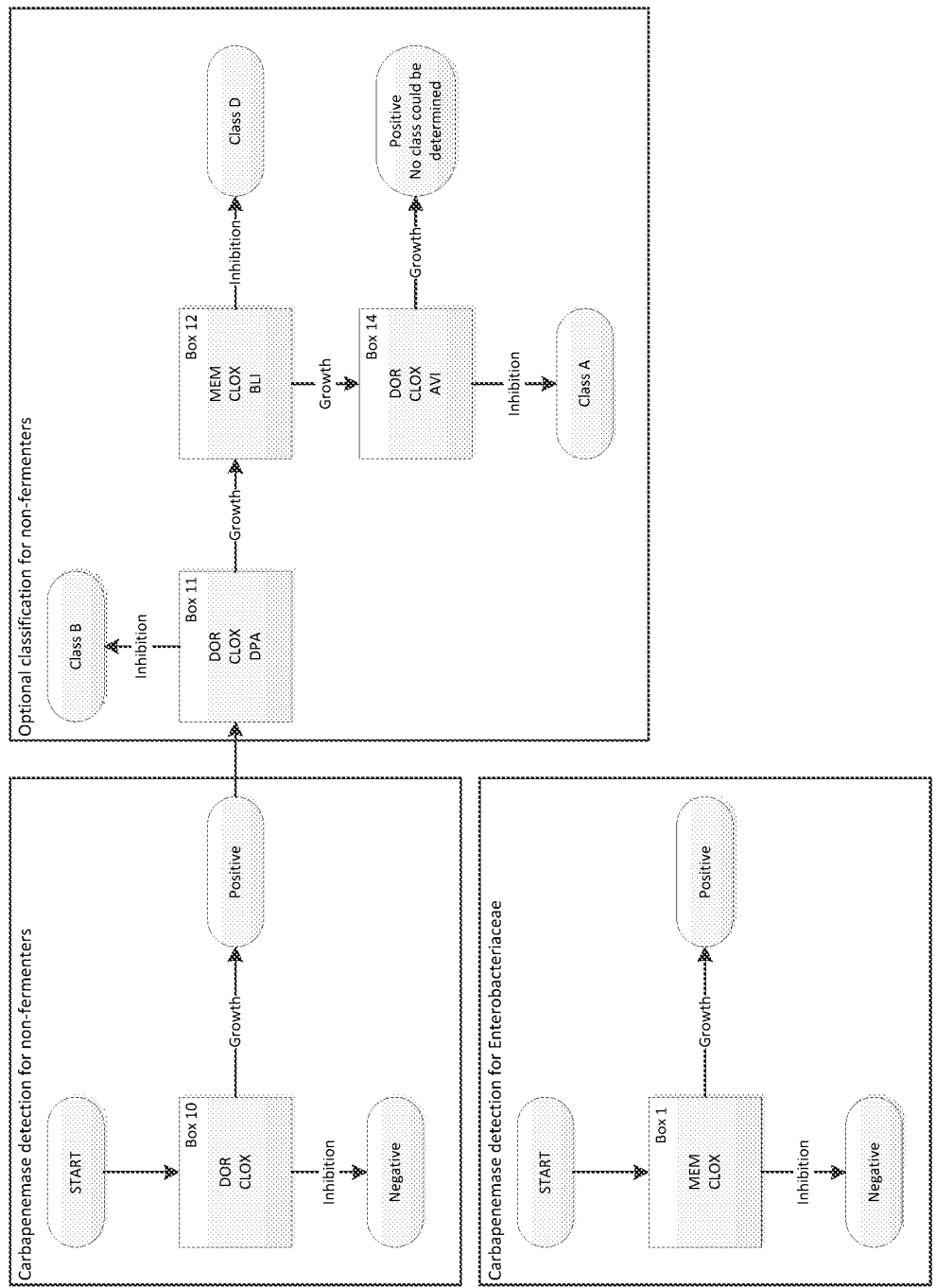
FIG. 39 shows a flowchart of an embodiment of an algorithm for Enterobacteriaceae and nonfermenters and classification of nonfermenters.

In some embodiments, the test comprises at least 5 wells, wherein one well is for the detection of CPO enteric bacteria, one well is for the detection of CPO non-fermenting bacteria, and 3 wells are for Ambler classification of the carbapenamase produced by non-fermenting bacteria (e.g., FIG. 39). Thus, in some embodiments, at least 3 wells allow for Ambler classification of the carbapenamase produced by non-fermenting bacteria (e.g., FIG. 39). In some embodiments, the number of wells used for Ambler classification of the carbapenamase produced by non-fermenting bacteria is 2 to 4. In some embodiments, the number of wells used for Ambler classification of the carbapenamase produced by non-fermenting bacteria is 2, 3, 4 or more.

In some embodiments, the number of wells for Ambler classification of the carbapenamase regardless of whether the carbapenamase is produced by enteric or non-fermenting bacteria is 9, wherein 4 well are for non-fermenting bacteria and 5 wells are for enteric bacteria (e.g., FIG. 38).

Example 1

Identification of Class A Carbapenemase Expression

Enteric Bacteria

Detection tests indicate the expression by enteric bacteria of Class A carbapenemase if the bacteria grow in the presence of MEM at 0.06 µg/ml, and CLOX at 0.1 mg/ml, do not grow in the presence of MEM at 0.06 mg/ml, CLOX at 0.1 mg/ml, DPA at 0.18 mg/ml, and do not grow in the presence of MEM at 0.03 mg/ml, CLOX at 0.1 mg/ml, RPX at 8 µg/ml.

Detection tests indicate the expression by enteric bacteria of Class A carbapenemase if the bacteria grow in the presence of MEM at 0.06 µg/ml, and CLOX at 0.1 mg/ml, grow in the presence of MEM at 0.06 mg/ml, CLOX at 0.1 mg/ml, DPA at 0.18 mg/ml, and do not grow in the presence of MEM at 0.06 mg/ml, CLOX at 0.1 mg/ml, RPX at 8 µg/ml.

Detection tests indicate the expression by enteric bacteria of Class A carbapenemase if the bacteria grow in the presence of MEM at 0.06 µg/ml, and CLOX at 0.1 mg/ml, do not grow in the presence of TEM at 64 µg/ml, EDTA at 0.25 mg/ml, grow in the presence of DOR at 0.06 µg/ml, CLOX at 0.1 mg/ml, EDTA at 0.25 mg/ml, and do not grow in the presence of MEM at 0.06 µg/ml, CLOX at 0.1 mg/ml, RPX at 8 µg/ml.

Non-Fermenting Bacteria

Detection tests indicate the expression by non-fermenting bacteria of Class A carbapenemase if the bacteria grow in the presence of DOR at 1 µg/ml, and CLOX at 0.1 mg/ml, grow in the presence of DOR at 1 µg/ml, CLOX at 0.1 mg/ml, DPA at 0.18 mg/ml, grow in the presence of MEM at 4 µg/ml, CLOX at 0.1 mg/ml, BLI at 5 µg/ml, and do not grow in the presence of DOR at 8 µg/ml, CLOX at 0.1 mg/ml, AVI at 4 µg/ml.

Example 2

Identification of Class B Carbapenemase Expression

Enteric Bacteria

Detection tests indicate the expression by enteric bacteria of Class B carbapenemase if the bacteria grow in the presence of MEM at 0.06 µg/ml, and CLOX at 0.1 mg/ml, do not grow in the presence of MEM at 0.06 µg/ml, CLOX at 0.1 mg/ml, DPA at 0.18 mg/ml, and grow in the presence of MEM at 0.03 µg/ml, CLOX at 0.1 mg/ml, RPX at 8 µg/ml.

Detection tests indicate the expression by enteric bacteria of Class B carbapenemase if the bacteria grow in the presence of MEM at 0.06 µg/ml, and CLOX at 0.1 mg/ml, do not grow in the presence of TEM at 64 µg/ml, EDTA at 0.25 mg/ml, do not grow in the presence of DOR at 0.06 µg/ml, CLOX at 0.1 mg/ml, EDTA at 0.25 mg/ml, and grow in the presence of DOR at 0.125 µg/ml.

Non-Fermenting Bacteria

Detection tests indicate the expression by non-fermenting bacteria of Class B carbapenemase if the bacteria grow in the presence of DOR at 1 µg/ml, and CLOX at 0.1 mg/ml, do not grow in the presence of DOR at 1 µg/ml, CLOX at 0.1 mg/ml, DPA at 0.18 mg/ml, and growth in DOR at 2 µg/ml, CLOX at 0.1 mg/ml, indicates the expression of Class B.

Detection tests indicate the expression by non-fermenting bacteria of Class B carbapenemase if the bacteria grow in the presence of DOR at 1 µg/ml, and CLOX at 0.1 mg/ml, do not grow in DOR at 1 µg/ml, CLOX at 0.1 mg/ml, DPA at 0.18 mg/ml, and grow in DOR at 2 µg/ml, CLOX at 0.1 mg/ml indicates the expression of Class B.

Example 3

Identification of Class D Carbapenemase Expression

Enteric Bacteria

Detection tests indicate the expression by enteric bacteria of Class D carbapenemase if the bacteria grow in the presence of MEM at 0.06 µg/ml, CLOX at 0.1 mg/ml, grow in the presence of MEM at 0.06 µg/ml, CLOX at 0.1 mg/ml, DPA at 0.18 mg/ml, and grow in the presence of MEM at 0.06 µg/ml, CLOX at 0.1 mg/ml, RPX at 8 µg/ml, and do not grow in the presence of DOR at 0.06 µg/ml, CLOX at 0.1 mg/ml, AVI at 4 µg/ml.

Detection tests indicate the expression by enteric bacteria of Class D carbapenemase if the bacteria grow in the presence of MEM at 0.06 µg/ml, CLOX at 0.1 mg/ml, and grow in the presence of TEM at 64 µg/ml, EDTA at 0.25 mg/ml.

Detection tests indicate the expression by enteric bacteria of Class D carbapenemase if the bacteria grow in the presence of MEM at 0.06 µg/ml, CLOX at 0.1 mg/ml, do not grow in the presence of TEM at 64 µg/ml, EDTA at 0.25 mg/ml, do not grow in the presence of DOR at 0.06 µg/ml, CLOX at 0.1 mg/ml, EDTA at 0.25 mg/ml, and do not grow in the presence of DOR at 0.125 µg/ml.

Non-Fermenting Bacteria

Detection tests indicate the expression by non-fermenting bacteria of Class D carbapenemase if the bacteria grow in the presence of DOR at 1 µg/ml, CLOX at 0.1 mg/ml, grow in the presence of DOR at 1 µg/ml, CLOX at 0.1 mg/ml, DPA at 0.18 mg/ml, and do not grow in the presence of MEM at 4 µg/ml, CLOX at 0.1 mg/ml, BLI at 5 µg/ml.

Detection tests indicate the expression by non-fermenting bacteria of Class D carbapenemase if the bacteria grow in the presence of DOR at 1 µg/ml, CLOX at 0.1 mg/ml, grow in the presence of DOR at 1 µg/ml, CLOX at 0.1 mg/ml, DPA at 0.18 mg/ml, and do not grow in the presence of MEM at 4 µg/ml, CLOX at 0.1 mg/ml, BLI at 5 µg/ml.

Example 4

Identification of Class A, B or D Carbapenemase Expression

Enteric Bacteria

Detection tests indicate the expression by enteric bacteria of Class A, B and/or D carbapenemase if the bacteria grow in the presence of MEM at 0.06 µg/ml, CLOX at 0.1 mg/ml, do not grow in the presence of TEM at 64 µg/ml, EDTA at 0.25 mg/ml, grow in the presence of DOR at 0.06 µg/ml, CLOX at 0.1 mg/ml, EDTA at 0.25 mg/ml, grow in the presence of MEM at 0.06 µg/ml, CLOX at 0.1 mg/ml, RPX at 8 µg/ml, and grow in the presence of MEM at 0.5 µg/ml, CLOX at 0.1 mg/ml.

Non-Fermenting Bacteria

Detection tests indicate the expression by non-fermenting bacteria of Class A, B and/or D carbapenemase if the bacteria grow in the presence of DOR at 1 µg/ml, CLOX at 0.1 mg/ml, grow in the presence of DOR at 1 µg/ml, CLOX at 0.1 mg/ml, DPA at 0.18 mg/ml, and grow in the presence of MEM at 4 µg/ml, CLOX at 0.1 mg/ml, BLI at 5 µg/ml.

Detection tests indicate the expression by non-fermenting bacteria of Class A, B and/or D carbapenemase if the bacteria grow in the presence of DOR at 1 µg/ml, CLOX at 0.1 mg/ml, grow in the presence of DOR at 1 µg/ml, CLOX at 0.1 mg/ml, DPA at 0.18 mg/ml, grow in the presence of MEM at 4 µg/ml, CLOX at 0.1 mg/ml, BLI at 5 µg/ml, and grow in the presence of DOR at 8 µg/ml, CLOX at 0.1 mg/ml, AVI at 4 µg/ml.

Incubation Duration

The detection tests are performed for a defined incubation time period. In some embodiments, the incubation time period is the time it takes for the detection reaction to reach completion. In some embodiments, the incubation time period is predetermined and defined by the user. The incubation time for the detection tests can range from about 3 hours to about 16 hours. Thus, a growth or no growth outcome of the detection tests is obtained within a time frame defined by the incubation time.

Traditional assays (e.g., plate-based assays) require at least 16 hours to about 24 hours or longer for the identification of antibiotic resistant bacteria. In contrast, the present disclosure provides more rapid detection tests. For example, the time frame for the detection test in each well is, or is about, 15 min to 3 hours. In some embodiments, the duration of the detections tests can range from about 5 hours to about 10 hours. In some embodiments, the duration of the detections tests for enteric bacteria ranges from about 6 hours to about 8 hours. In some embodiments, the duration of the detections tests for enteric bacteria ranges from about 5 hours to about 7 hours. In some embodiments, the duration of the detections tests for non-fermenting bacteria ranges from about 8 hours to about 11 hours. In some embodiments, the duration of the detections tests for non-fermenting bacteria ranges from about 7 hours to about 14 hours.

One or more detectors are provided that measure the results of the detection tests by measuring presence or absence of bacterial growth in the presence of various combinations of one or more antibiotics and one or more inhibitors. The detectors measure the results of the detection tests at regular intervals until the defined incubation time period following which detection is performed. The detectors detect growth or no growth in a rapid and automated fashion. For example, the time frame for the detector to measure the results of the detection tests in the plurality of wells can about 5 minutes to about 10 minutes.

In some embodiments, the detectors can analyze the results of detection tests in the plurality of wells serially. In some embodiments, the detectors can analyze the results of detection tests in the plurality of wells simultaneously. It is more efficient to analyze the results of the detection tests in the plurality of wells simultaneously.

The detection tests in each of the plurality of wells are redox reactions based and the one or more detection reagents in the wells allow for redox reaction based detection of absence or presence of growth. In some embodiments, the detection tests in each of the plurality of wells to detect growth are based on turbidity in each of the plurality of wells. In some embodiments, the detection tests in each of the plurality of wells to detect growth are based on a combination of redox reactions and turbidity in each of the plurality of wells.

Redox reactions are well-known in the art and comprise chemical reactions in which the oxidation states of atoms are altered. Redox reactions involve the transfer of electrons between two or more chemical species. The chemical species from which one or more electrons are transferred is oxidized, whereas the chemical species to which the one or more electrons are transferred is reduced. Detection of growth based on turbidity is well-known in the art. A non-limiting example of detection of growth based on turbidity comprises measuring absorbance of light at a wavelength of 600 nm.

Non-limiting examples of redox reactions include combination, decomposition, displacement, combustion, and disproportionation type redox reaction. In some embodiments, the redox reaction can be based on a change in pH, color, etc.

The detectors analyze the results of detection tests in the plurality of wells by detecting the outcome of the redox reactions in the wells. The detectors analyze the results of the redox reactions in a rapid and automated manner.

In some embodiments, an outcome of the detection tests is growth of the one or more bacteria in the plurality of wells. In some embodiments, an outcome of the detection tests is no growth of the one or more bacteria in the sample in the plurality of wells.

Previously disclosed assays can only be used for enteric bacteria. In contrast, in some embodiments, the detections tests can be used for enteric bacteria. In some embodiments, the detections tests can be used for non-fermenting bacteria.

In some embodiments, the detections tests can be used for both enteric and non-fermenting bacteria.

In some embodiments, the detections tests are amendable to automation, allowing rapid differentiation and identification of the different classes of carbapenemases. In some embodiments, the detection tests are combined with algorithms that automate the phenotypic detection of carbapenemase production and Ambler classification of carbapenemase within a few hours.

One or more algorithms process the data from the one or more detectors to query the results in the wells. The algorithm takes approximately 1 minute to 10 minutes to process the data. Based on the presence or absence of bacterial growth in the well, the algorithm provides an output of growth or no growth in the wells. In some embodiments, the time frame for the entire algorithm is about 6 hours to about 12 hours. In some embodiments, the time frame for the entire algorithm is about 5 hours to about 7 hours.

Although the disclosure refers to tests occurring in "wells" throughout, one of skill in the art will recognize that numerous test sites are suitable for the tests disclosed herein, and therefore "wells" is not limiting. For example, microtiter plates, cuvettes, test tubes, or any other suitable structure known in the art can be used.

Figure 30:
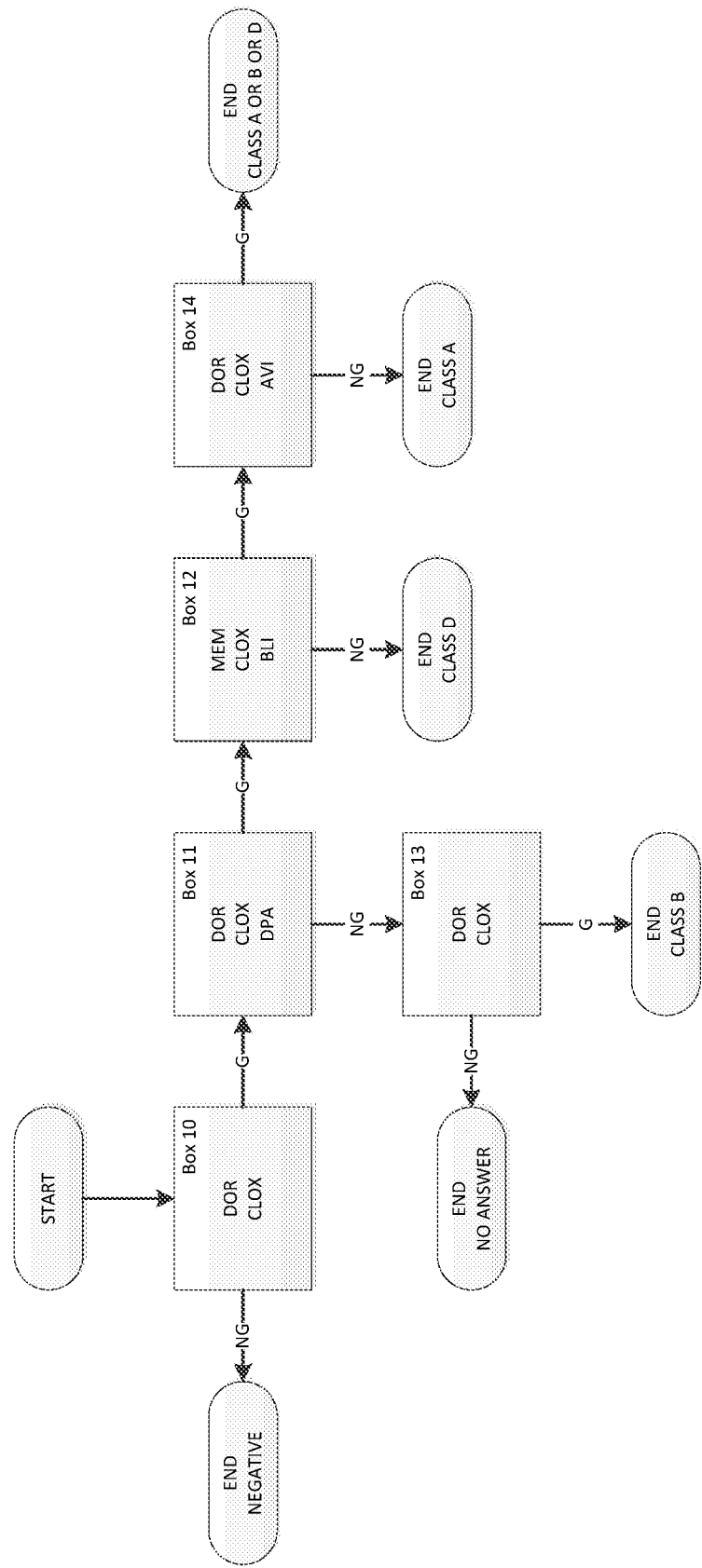
FIG. 30 shows a flowchart of an embodiment of an algorithm for non-fermenting gram negative rod bacteria.

Non-limiting examples of algorithms are provided in the Example 6 (FIG. 25)-Example 10 (FIG. 30). Each "Box" in the algorithm represents an assay well of the detection tests provided herein.

BD Phoenix™ CPO Detect Algorithms

In some embodiments, one or more algorithms are provided that allow for the rapid and automated identification of carbapenemase expressing bacteria along with identification of the Ambler class of the carbapenemase. Inclusion of the algorithm in an automated platform produced a high level of accuracy and improved time to result.

In some embodiments, a computer or computer system is provided that use one or more of the algorithms provided herein to analyze and interpret the results of the detections tests obtained using CPO Detect. For example, the computer queries the results of the detection tests obtained in a plurality of wells and provides an output based on the results (e.g., growth or no growth) from the queried detection tests as defined by the algorithm. The detection test result provided to the system is either positive for growth (G) or no growth (NG) in the one or more wells of the detection tests within a defined time frame. Based on the results provided for a queried well, (growth or no growth), the system proceeds to the next query as defined by the algorithm. The system queries the plurality of test results until the system reaches an output point in the algorithm, at which point the system generates an output result.

Figure 25:
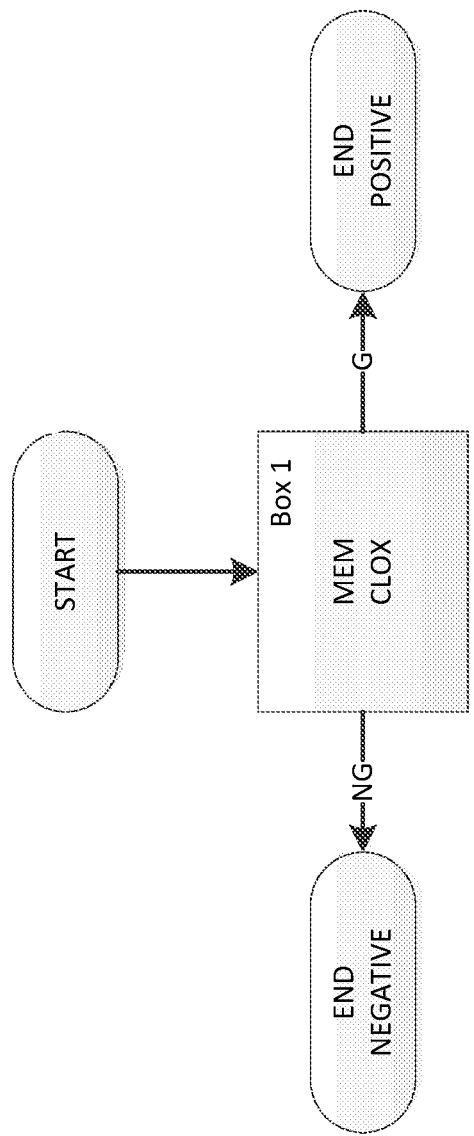
FIG. 25 shows a flowchart of an embodiment of an algorithm for enteric gram negative bacteria.

Non-limiting examples (Example 5-Example 10) of algorithms are provided below. Each "Box" in the algorithm represents a well (or optionally the average of several identical wells) of the detection tests provided herein comprising an input sample comprising one or more bacteria, one or more detection reagents, and one or more antibiotics with/without one or more carbapenemase inhibitors. For example, Box 1 in FIG. 25 represents the well(s) of the detection test comprising a combination of an input sample comprising one or more enteric bacteria, one or more detection reagents, MEM at 0.06 µg/ml, and CLOX at 0.1 mg/ml. As discussed, the determination of whether the sample comprises enteric or non-fermenting bacteria can be made by methods known in the art, for example, spot Oxidase Test, MALDI-TOF and biochemical tests, including Phoenix ID system. The determination can be made before the sample is run through the test, or after the sample is run. In the example algorithms presented herein, the determination of whether the sample contains enteric or non-fermenting bacteria is made either prior to or after the steps of the algorithm shown. In some embodiments, the algorithms presented herein can be run without making a prior determination of whether the sample contains enteric or non-fermenting bacteria. If the test is not appropriate for the CPO detection and/or classification of the type of bacteria (e.g., non-fermenting or enteric) determined to be present after the test has been run, the test results can simply be ignored.

Example 5

The flowchart of the algorithm illustrated in FIG. 25 is used to determine whether or not the sample contains an enteric bacteria producing a Class A, B or D carbapenemase. Box 1 represents a well(s) that comprises a combination of an input sample comprising one or more enteric bacteria, MEM at 0.06 µg/ml, CLOX at 0.1 mg/ml, and one or more detection reagents. As shown in FIG. 25 for enteric bacteria, the system can query the result of the detection test in Box 1. If the result of the test in Box 1 is growth (G), the system reports a positive output result, indicating the presence of an enteric bacteria producing a Class A, B or D carbapenemase in the sample. If the result of the test in Box 1 is no growth (NG), the output result reported is negative—the sample does not contain an enteric bacteria producing a Class A, B or D carbapenemase. As discussed herein, the reporting of results are contingent on determining that the bacteria being tested are enteric, either before or after the tests are run, ensuring that the proper algorithm is being used for the type of bacteria present.

Example 6

Identification of Carbapenemase Class for Enteric Bacteria

Figure 26:
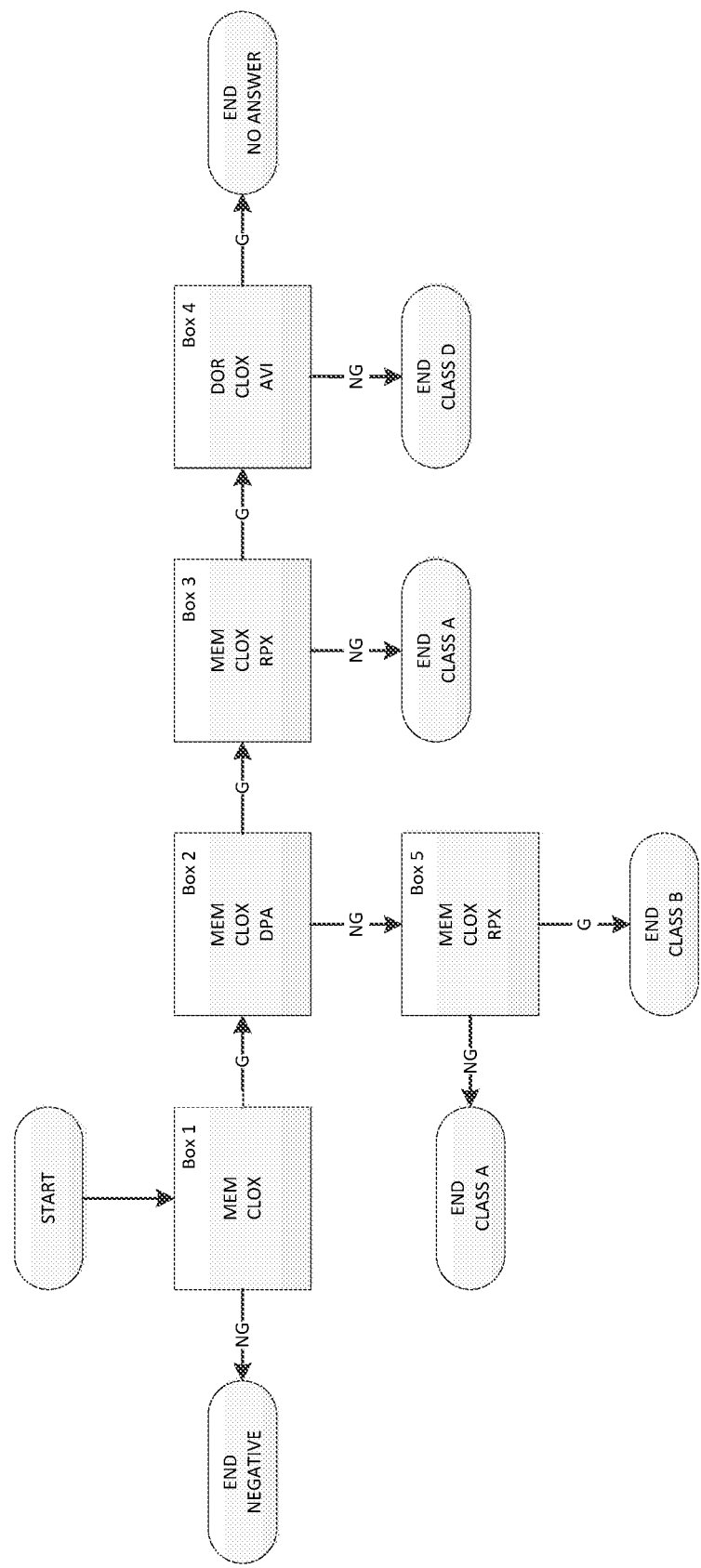
FIG. 26 shows a flowchart of an embodiment of an algorithm for enteric gram negative bacteria.

FIG. 26 illustrates a flowchart of an embodiment of an algorithm to determine whether enteric bacteria in the sample produce a carbapenemase, and if so which class. As shown in FIG. 26 for enteric bacteria, if the system queries the result of the test of Box 1 and growth is reported, it will proceed to query the result of the test of Box 2. Box 2 represents a well(s) that comprises a combination of an input sample comprising one or more enteric bacteria, MEM at 0.06 µg/ml, CLOX at 0.1 mg/ml, DPA at 0.18 mg/ml, and one or more detection reagents. If the system queries the result of the test of Box 2 and no growth is reported, it will proceed to query the result of the test of Box 5. Box 5 represents a well(s) that comprises a combination of an input sample comprising one or more enteric bacteria, MEM at 0.03 µg/ml, CLOX at 0.1 mg/ml, RPX at 8 µg/ml, and one or more detection reagents. If the system queries Box 5 and no growth is reported, it will end querying and output a result that the sample contains enteric bacteria expressing Class A carbapenemase. If the system queries Box 2 and no growth is reported, it will query the result of the test of Box 5. If the system queries Box 5 growth is reported, it will end querying and output a result that the sample contains bacteria expressing Class B carbapenemase. If the system queries Box 2 and growth is reported, it will query for the result of the test of Box 3. Box 3 represents a well that comprises a combination of an input sample comprising one or more enteric bacteria, MEM at 0.06 µg/ml, CLOX at 0.1 mg/ml, RPX at 8 µg/ml, and one or more detection reagents.

If the system queries Box 3 and no growth is reported, it will end querying and output a result that the sample contains an enteric bacteria expressing Class A carbapenemase. If the system queries Box 3 and growth is reported, it will proceed to query the results of Box 4. Box 4 represents a well(s) that comprises a combination of an input sample comprising one or more enteric bacteria, DOR at 0.06 µg/ml, CLOX at 0.1 mg/ml, AVI at 4 µg/ml, and one or more detection reagents. If the system queries Box 4 and no growth is reported, it will end querying and output a result that the sample contains enteric bacteria expressing Class D carbapenemase. If the system queries Box 4 and growth is reported, it will end querying and output a result that it could not determine which class of carbapenemase the enteric bacteria expresses.

As discussed herein, the reporting of results are contingent on determining that the bacteria being tested are enteric, either before or after the tests are run, ensuring that the proper algorithm is being used for the type of bacteria present.

Example 7

Identification of Carbapenemase Class for Enteric Bacteria

Figure 27:
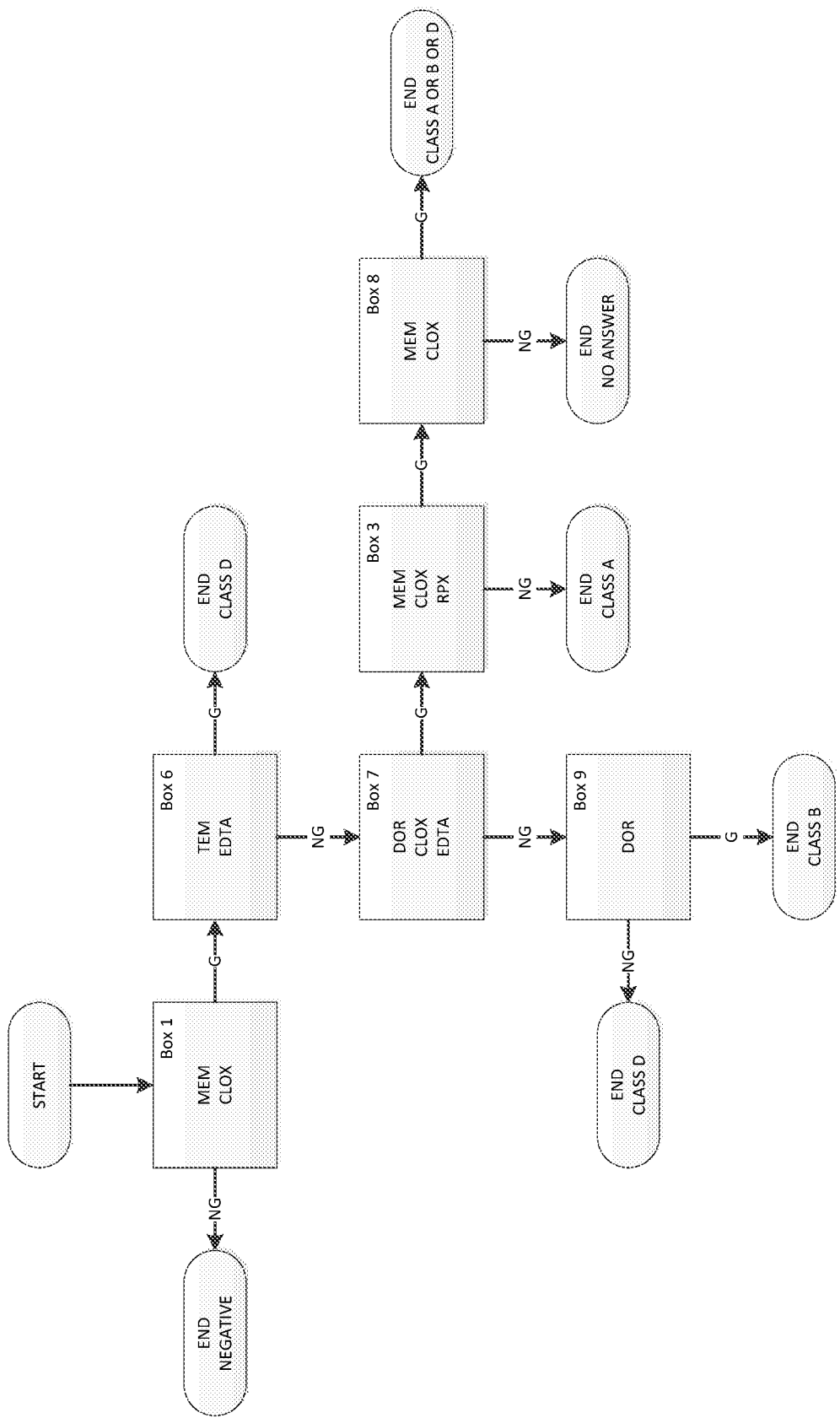
FIG. 27 shows a flowchart of an embodiment of an algorithm for enteric gram negative bacteria.

FIG. 27 illustrates a flowchart of an embodiment of an algorithm to determine whether enteric bacteria in the sample produce a carbapenemase, and if so which class. As shown in FIG. 27 for enteric bacteria, if the system queries the result of the test of Box 1 and growth is reported, it will proceed to query the result of the test of Box 6. Box 6 represents a well(s) that comprises a combination of an input sample comprising one or more enteric bacteria, TEM at 64 µg/ml, EDTA at 0.25 mg/ml, and one or more detection reagents. If the system queries the result of the test of Box 6 and no growth is reported, it will proceed to query the result of the test of Box 7. Box 7 represents a well(s) that comprises a combination of an input sample comprising one or more enteric bacteria, DOR at 0.06 µg/ml, CLOX at 0.1 mg/ml, EDTA at 0.25 mg/ml, and one or more detection reagents. If the system queries the result of the test of Box 7 and growth is reported, it will proceed to query the result of the test of Box 3. If the algorithm queries the result of the test of Box 3 and no growth is reported, it will end querying and output a result that the sample contains enteric bacteria expressing Class A carbapenemase. If the system queries the result of the test of Box 6 and no growth is reported, it will proceed to query the result of the test of Box 7. If the algorithm queries the result of the test of Box 7 and no growth is reported, it will proceed to query the result of the test of Box 9. Box 9 represents a well(s) that comprises a combination of an input sample comprising one or more enteric bacteria, DOR at 0.125 µg/ml, and one or more detection reagents. If the system queries the result of the test of Box 9 and growth is reported, it will end querying and output a result that the sample contains enteric bacteria expressing Class B carbapenemase. If the system queries the result of the test of Box 6 and growth is reported, it will end querying and output a result that the sample contains enteric bacteria expressing Class D carbapenemase. If the system queries the result of the test of Box 9 and no growth is reported, it will end querying and output a result that the sample contains enteric bacteria expressing Class D carbapenemase. If the system queries the result of the test of Box 3 and growth is reported, it will proceed to query the result of the test of Box 8. Box 8 represents a well(s) that comprises a combination of an input sample comprising one or more enteric bacteria, MEM at 0.5 µg/ml, CLOX at 0.1 mg/ml, and one or more detection reagents. If the system queries the result of the test of Box 8 and growth is reported, it will end querying and output a result that the sample contains enteric bacteria expressing one or more of Class A, B or D carbapenemase. If the system queries the result of the test of Box 8 and no growth is reported, it will end querying and output a result that it could not determine which class of carbapenemase the enteric bacteria expresses.

As discussed herein, the reporting of results are contingent on determining that the bacteria being tested are enteric, either before or after the tests are run, ensuring that the proper algorithm is being used for the type of bacteria present.

Example 8

Figure 28:
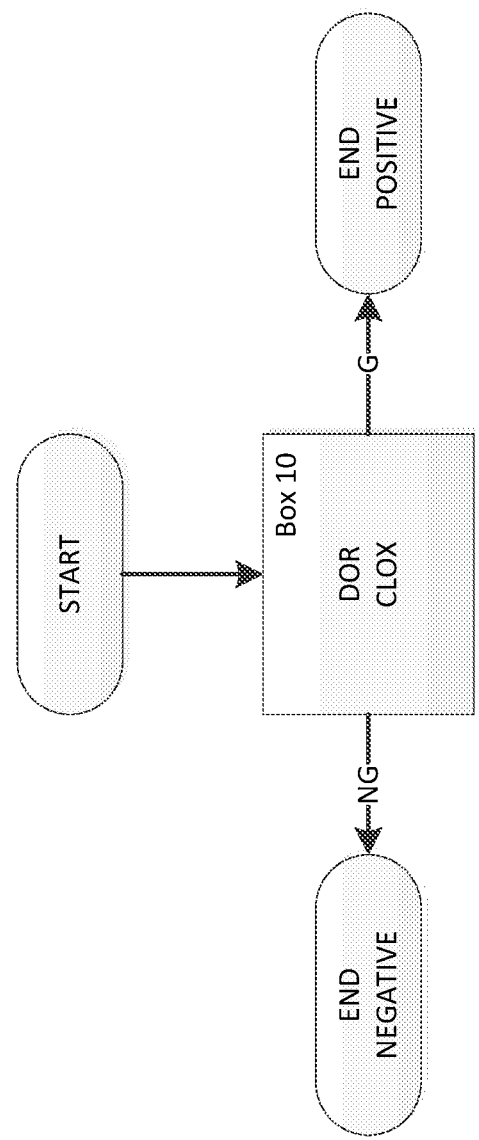
FIG. 28 shows a flowchart of an embodiment of an algorithm for non-fermenting gram negative rod bacteria.

FIG. 28 illustrates a flowchart of an embodiment of an algorithm to determine whether or not the sample contains an non-fermenting bacteria producing a Class A, B or D carbapenemase. Box 10 represents a well(s) that comprises a combination of an input sample comprising one or more enteric bacteria, DOR at 1 µg/ml, CLOX at 0.1 mg/ml, and one or more detection reagents. As shown in FIG. 28 for non-fermenting bacteria, the system can query the result of the detection test in Box 10. If the result of the test in Box 10 is growth (G), the system reports a positive output result, indicating the presence of an enteric bacteria producing a Class A, B or D carbapenemase in the sample. If the result of the test in Box 10 is no growth (NG), the output result reported is negative—the sample does not contain a non-fermenting bacteria producing a Class A, B or D carbapenemase. As discussed herein, the reporting of results are contingent on determining that the bacteria being tested are non-fermenting, either before or after the tests are run, ensuring that the proper algorithm is being used for the type of bacteria present.

Example 9

Identification of Carbapenemase Class for Non-Fermenting Bacteria

Figure 29:
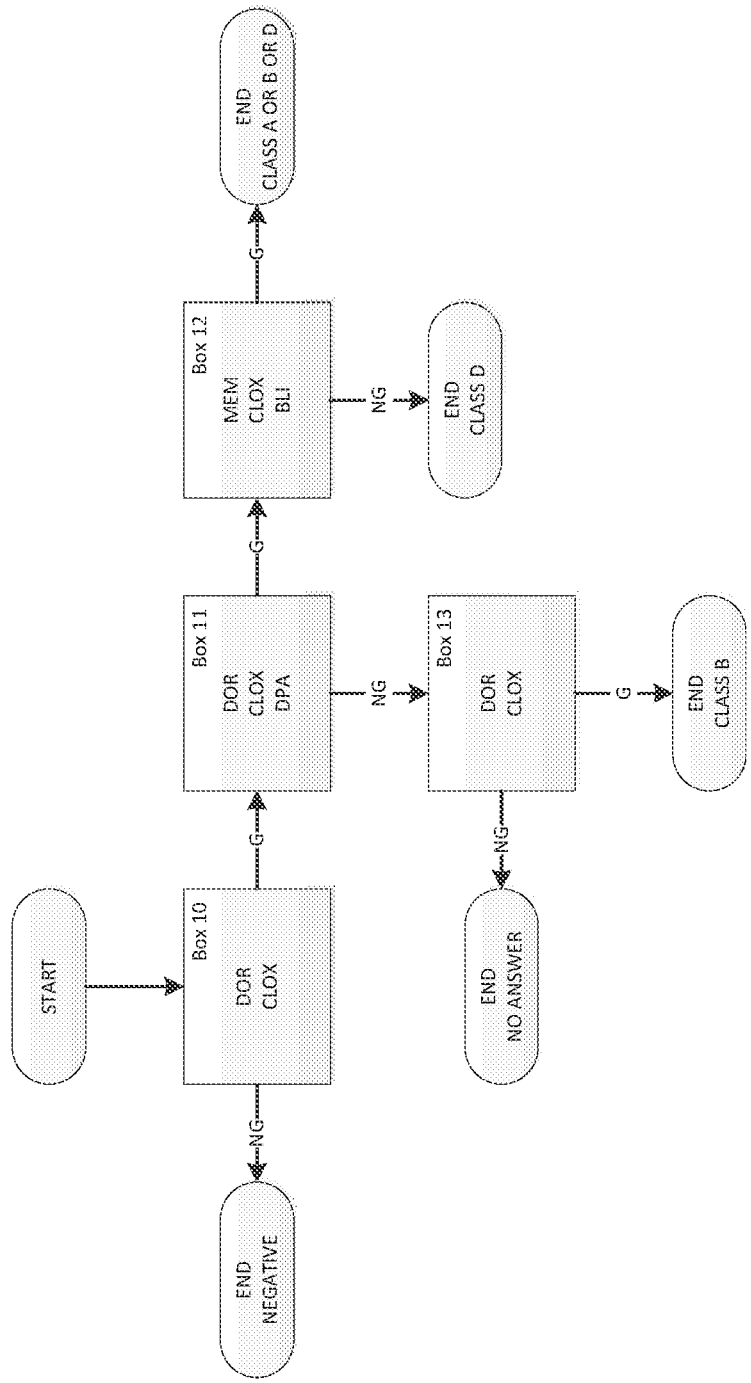
FIG. 29 shows a flowchart of an embodiment of an algorithm for non-fermenting gram negative rod bacteria.

FIG. 29 illustrates a flowchart of an embodiment of an algorithm to determine whether non-fermenting bacteria in the sample produce a carbapenemase, and if so which class. As shown in FIG. 29 for non-fermenting bacteria, if the system queries the result of the test of Box 10 and growth is reported, it will proceed to query the result of the test of Box 11. Box 11 represents a well(s) that comprises a combination of an input sample comprising one or more non-fermenting bacteria, DOR at 1 µg/ml, CLOX at 0.1 mg/ml, DPA at 0.18 mg/ml, and one or more detection reagents. If the system queries the result of the test of Box 11 and no growth is reported, it will query the result of the test of Box 13. Box 13 represents a well(s) that comprises a combination of an input sample comprising one or more non-fermenting bacteria, DOR at 2 µg/ml, CLOX at 0.1 mg/ml, and one or more detection reagents. If the system queries the result of the test of Box 13 and growth is reported, it will end querying and output a result that the sample contains non-fermenting bacteria expressing Class B carbapenemase. If the system queries the result of the test of Box 11 and growth is reported, it will proceed to query the result of the test of Box 12. Box 12 represents a well(s) that comprises a combination of an input sample comprising one or more non-fermenting bacteria, MEM at 4 µg/ml, CLOX at 0.1 mg/ml, BLI at 5

µg/ml, and one or more detection reagents. If the system queries the result of the test of Box 12 and no growth is reported, it will end querying and output a result that the sample contains non-fermenting bacteria expressing Class D carbapenemase. If the system queries the result of the test of Box 12 and growth is reported, it will end querying and output a result that the sample contains non-fermenting bacteria expressing one or more of Class A, B or D carbapenemase. If the system queries the result of the test of Box 13 and no growth is reported, it will end querying and output a result that it could not determine which class of carbapenemase the non-fermenting bacteria expresses.

As discussed herein, the reporting of results are contingent on determining that the bacteria being tested are non-fermenting, either before or after the tests are run, ensuring that the proper algorithm is being used for the type of bacteria present.

Example 10

Identification of Carbapenemase Class for Non-Fermenting Bacteria

FIG. 30 illustrates a flowchart of an embodiment of an algorithm to determine whether non-fermenting bacteria in the sample produce a carbapenemase, and if so which class. As shown in FIG. 30 for non-fermenting bacteria, if the system queries Box 10 and detects growth, it will query Box 11. If the system queries Box 11 and detects growth, it will query Box 12. If the system queries the result of the test of Box 12 and detects growth, it will query the result of the test of Box 14. Box 14 represents a well(s) that comprises a combination of an input sample comprising one or more non-fermenting bacteria, DOR at 8 µg/ml, CLOX at 0.1 mg/ml, AVI at 4 µg/ml, and one or more detection reagents. If the system queries the result of the test of Box 14 and no growth is reported, it will end querying and output a result that the sample contains non-fermenting bacteria expressing Class A carbapenemase. If the system queries the result of the test of Box 11 and no growth is reported, it will proceed to query the result of the test of Box 13. If the system queries the result of the test of Box 13 and growth is reported, it will end querying and output a result that the sample contains non-fermenting bacteria expressing Class B carbapenemase. If the system queries the result of the test of Box 11 and growth is reported, it will proceed to query the result of the test of Box 12. If the system queries the result of the test of Box 12 and no growth is reported, it will end querying and output a result that the sample contains non-fermenting bacteria expressing Class D carbapenemase. If the system queries the result of the test of Box 12 and growth is reported, it will proceed to query the result of the test of Box 14. If the system queries the result of the test of Box 14 and growth is reported, it will end querying and output a result that the sample contains non-fermenting bacteria expressing one or more of Class A, B or D carbapenemase. If the system queries the result of the test of Box 13 and no growth is reported, it will end querying and output a result that it could not determine which class of carbapenemase the non-fermenting bacteria expresses.

As discussed herein, the reporting of results are contingent on determining that the bacteria being tested are non-fermenting, either before or after the tests are run, ensuring that the proper algorithm is being used for the type of bacteria present.

Example 10.1

Carbapenemase Detection for Enterobacteriaceae and Non-Fermenters

Figure 36:
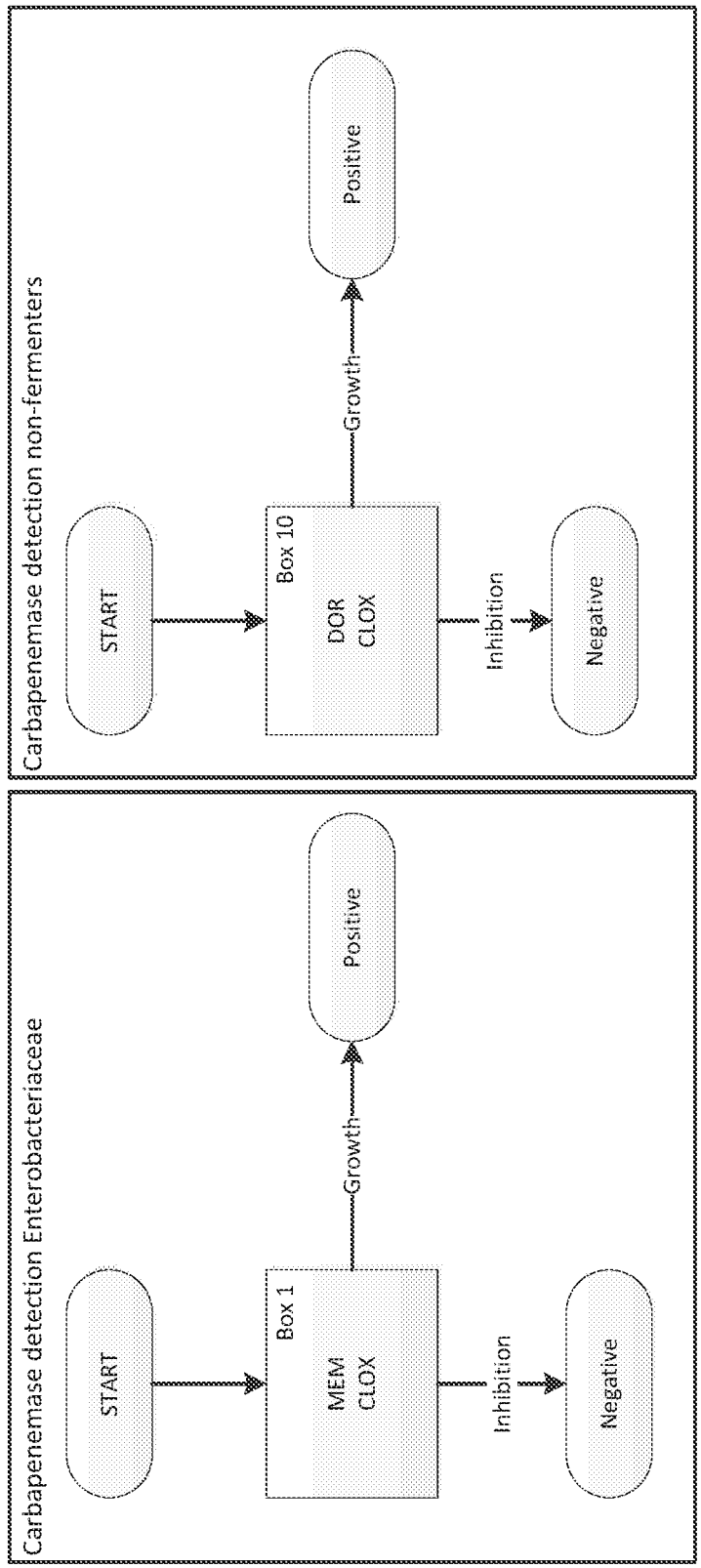
FIG. 36 shows a flowchart of an embodiment of an algorithm for Enterobacteriaceae and nonfermenters.

FIG. 36 shows a flowchart of an embodiment of an algorithm for CPO detection of Enterobacteriaceae and nonfermenters. As shown in FIG. 36 for enteric bacteria, the system can query the result of the detection test in Box 1. If the result of the test in Box 1 is growth, the system reports a positive output result, indicating the presence of enteric bacteria producing a Class A, B or D carbapenemase in the sample. If the result of the test in Box 1 is no growth (inhibition), the output result reported is negative—the sample does not contain enteric bacteria producing a Class A, B or D carbapenemase. As shown in FIG. 36 for non-fermenting bacteria, the system can query the result of the detection test in Box 10. If the result of the test in Box 10 is growth, the system reports a positive output result, indicating the presence of non-fermenting bacteria producing a Class A, B or D carbapenemase in the sample. If the result of the test in Box 10 is no growth (inhibition), the output result reported is negative—the sample does not contain non-fermenting bacteria producing a Class A, B or D carbapenemase.

As discussed herein, the reporting of results are contingent on determining that the bacteria being tested are enteric and/or non-fermenting, either before or after the tests are run, ensuring that the proper algorithm is being used for the type of bacteria present.

Example 10.2

Carbapenemase Detection for Enterobacteriaceae and Non-Fermenters and Ambler Classification for Enterobacteriaceae FIG. 37 shows a flowchart of an embodiment of an algorithm for CPO detection of Enterobacteriaceae and nonfermenters and classification of Enterobacteriaceae. The algorithm in FIG. 37 builds on the algorithm in FIG. 36. As shown in FIG. 37 for enteric bacteria, the system can query the result of the detection test in Box 1. If the result of the test in Box 1 is growth, the system reports a positive output result, indicating the presence of enteric bacteria producing a Class A, B or D carbapenemase in the sample. If the result of the test in Box 1 is no growth (inhibition), the output result reported is negative—the sample does not contain enteric bacteria producing a Class A, B or D carbapenemase. As shown in FIG. 37 for non-fermenting bacteria, the system can query the result of the detection test in Box 10. If the result of the test in Box 10 is growth, the system reports a positive output result, indicating the presence of non-fermenting bacteria producing a Class A, B or D carbapenemase in the sample. If the result of the test in Box 10 is no growth (inhibition), the output result reported is negative—the sample does not contain non-fermenting bacteria producing a Class A, B or D carbapenemase.

The algorithm in FIG. 37 further allows determination of the class of carbapenemase produced by enteric bacteria. As shown in FIG. 37 for enteric bacteria, if the system queries the result of the test of Box 1 and growth is reported, it will proceed to query the result of the test of Box 6. If the system queries Box 6 and growth is reported, it will end querying and output a result that the sample contains enteric bacteria expressing Class D carbapenemase. If the system queries the result of the test of Box 6 and no growth (inhibition) is reported, it will proceed to query the result of the test of Box 7. If the system queries Box 7 and no growth (inhibition) is reported, it will proceed to query the result of the test of Box 9. If the system queries Box 9 and no growth (inhibition) is reported, it will end querying and output a result that the sample contains enteric bacteria expressing Class D carbapenemase. If the system queries Box 7 and growth is reported, it will query the result of the test of Box 3. If the system queries Box 3 and no growth (inhibition) is reported, it will end querying and output a result that the sample contains enteric bacteria expressing Class A carbapenemase. If the system queries Box 9 and growth is reported, it will end querying and output a result that the sample contains enteric bacteria expressing Class B carbapenemase. If the system queries Box 3 and growth is reported, it will end querying and output a result that it could not determine which class of carbapenemase the enteric bacteria expresses.

As discussed herein, the reporting of results are contingent on determining that the bacteria being tested are enteric and/or non-fermenting, either before or after the tests are run, ensuring that the proper algorithm is being used for the type of bacteria present.

Example 10.3

Carbapenemase Detection and Ambler Classification for Enterobacteriaceae and Non-Fermenters FIG. 38 shows a flowchart of an embodiment of an algorithm for CPO detection of Enterobacteriaceae and nonfermenters and classification of Enterobacteriaceae and nonfermenters. The algorithm in FIG. 38 builds on the algorithm in FIG. 37.

In addition to the procedures and results described for FIG. 37, the algorithm in FIG. 38 further allows determination of the class of carbapenemase produced by non-fermenting bacteria. As shown in FIG. 38 for enteric bacteria, if the system queries the result of the test of Box 10 and growth is reported, it will proceed to query the result of the test of Box 11. If the system queries Box 11 and no growth (inhibition) is reported, it will end querying and output a result that the sample contains non-fermenting bacteria expressing Class B carbapenemase. If the system queries the result of the test of Box 11 and growth is reported, it will proceed to query the result of the test of Box 12. If the system queries Box 12 and no growth (inhibition) is reported, it will end querying and output a result that the sample contains non-fermenting bacteria expressing Class D carbapenemase. If the system queries Box 12 and growth is reported, it will proceed to query the result of the test of Box 14. If the system queries Box 14 and no growth (inhibition) is reported, it will end querying and output a result that the sample contains non-fermenting bacteria expressing Class A carbapenemase. If the system queries Box 14 and growth is reported, it will end querying and output a result that it could not determine which class of carbapenemase the non-fermenting bacteria expresses.

As discussed herein, the reporting of results are contingent on determining that the bacteria being tested are enteric and/or non-fermenting, either before or after the tests are run, ensuring that the proper algorithm is being used for the type of bacteria present.

Example 10.4

Carbapenemase Detection for Enterobacteriaceae and Non-Fermenters and Ambler Classification for Non-Fermenters FIG. 39 shows a flowchart of an embodiment of an algorithm for CPO detection of Enterobacteriaceae and nonfermenters and classification of nonfermenters. The algorithm in FIG. 39 is the same as FIG. 38, except that the portion of the algorithm for classification of enteric bacteria is not included.

Example 11

Comparison of the BD Phoenix™ CPO Detect Test and bioMérieux Rapidec® Carba NP Test Data in this Example are related to a study that was designed to assess the performance of BD Phoenix™ CPO Detect to meet the current clinical need. As disclosed herein, the BD Phoenix™ CPO Detect test is designed for integration into susceptibility panels to provide both CPO detection and carbapenemase classification, to reduce operator time, and to expedite reporting of carbapenemases. The comparison test was the bioMérieux Rapidec® Carba NP test, a currently marketed standalone test which detects but does not classify carbapenemases. Thus, The BD Phoenix™ CPO Detect IUO Panel and the bioMérieux Rapidec® Carba NP test were compared for accuracy and impact on workflow.

Example 11.1

Methodology

The study was performed in the laboratory of BD Life Sciences, Sparks, Md. with BD research staff providing laboratory and computing support. GKID Inc. prepared the inocula for both tests and interpreted all bioMérieux Rapidec® Carba NP tests. BD staff were not involved in any aspect of the bioMérieux Rapidec® Carba NP testing. Both tests were blinded and performed according to the manufacturers' recommendations. Inocula were prepared from overnight growth on BD blood agar plates adjacent to imipenem disks which were used to enhance the retention of carbapenemase-encoding plasmids in unstable isolates.

The bioMérieux Rapidec® Carba NP test was sometimes difficult to interpret. The manufacturer's definition of a positive test is one that yields a "significant variation in color" between test and test control wells. This definition was problematic because it did not provide a boundary between significant and insignificant color variations. For example, significant variation in color was not observed with *E. cloacae* 0164 (IMI Class A carbapenemase), which should yield positive test, *E. coli* 0104 (KPC Class A carbapenemase), which should yield positive test, *E. coli* 0058 (ESBL), which should yield negative test, and *K. pneumoniae* G1673 (CMY-2 plasmid-mediated AmpC), which should yield negative test. For this reason, borderline results were interpreted as positive (Interpretation 1) and also as negative (Interpretation 2). This provided two sets of bioMérieux Rapidec® Carba NP results.

Example 11.2

Isolates

Two hundred ninety four (294) isolates plus three quality control strains were tested. The test isolates comprised 236 isolates of Enterobacteriaceae, *Pseudomonas aeruginosa* and *Acinetobacter baumannii* producing a single carbapenemase, 7 (seven) producing 2 (two) carbapenemases, and 51 negative controls. A summary of the types of isolates (numbers of isolates of each species plus resistance mechanism group) is provided in Table 1.1, Table 1.2 and Table 1.3. The mechanism key for Tables 1.1-1.3 are provided in Table 1.3.

The isolates were obtained from:

The FDA/CDC Challenge panel of carbapenemase- and non-carbapenemase-producing gram-negative rods;

Well-characterized isolates of carbapenemase- and non-carbapenemase-producing gram-negative rods provided by GKID Inc.; and ATCC Quality Control isolates:

*K. pneumoniae* BAA-1705 (positive, KPC)—used for both tests

*K. pneumoniae* ATCC 700603 (negative)—used for both tests *E. coli* ATCC BAA 2452 (positive, NDM-1)—used for BD Phoenix™ CPO Detect only.

These were not routine clinical isolates. They were chosen to provide an extreme test of diagnostic capability. The reference standard was prior characterizations by molecular, phenotypic and biochemical tests. There were 110 producers of Class A carbapenemases including KPC, NMC-A, IMI and SME enzymes, 91 producers of Class B carbapenemases (metallo-β-lactamases) including NDM, GIM, SPM, IMP, and VIM enzymes, 35 producers of Class D carbapenemases including OXA-23, 40, 48, 58, 72, 181, and 232, and 7 (seven) isolates producing 2 (two) carbapenemases. The 51 negative controls (35 AmpC and 16 other non-AmpC) produced ESBLs, AmpCs (including hyperproducers), K1, broad spectrum β-lactamases and porin mutants.

TABLE 1.1

Isolates Expressing Class A Carbapenemase

| Organism | Class A Carbapanemases (n = 110) | No. |
|---|---|---|
| A. baumannii | KPC* | 1 |
| C. freundii | KPC | 4 |
| C. amalonaticus | KPC | 1 |
| E. cloacae | KPC | 21 |
| E. coli | KPC | 6 |
| H. alvei | KPC | 1 |
| K. pneumoniae | KPC | 42 |
| K. oxytoca | KPC | 4 |
| K. ozaenae | KPC | 1 |
| Kluyvera ascorbata | KPC | 1 |
| M. morganii | KPC | 1 |
| P. mirabilis | KPC | 2 |
| P. aeruginosa | KPC | 3 |
| R. ornitholytica | KPC | 1 |
| S. marcescens | KPC | 1 |
| K. pneumoniae | KPC-4 | 2 |
| P. aeruginosa | KPC-5 | 2 |
| K. pneumoniae | KPC-6 | 1 |
| K. pneumoniae | KPC-8 | 2 |
| E. cloacae | IMI | 2 |
| E. cloacae | NMC-A | 1 |
| S. marcescens | SME | 10 |

TABLE 1.2

Isolates Expressing Class B and Class D Carbapenemases

| Organism | | |
|---|---|---|
| Class B Carbapenemases (n = 91) | | |
| E. aerogenes | IMP | 1 |
| K. pneumoniae | IMP | 2 |
| A. baumannii | IMP-1 | 1 |
| P. aeruginosa | IMP-1 | 1 |
| S. marcescens | IMP-1 | 1 |
| A. baumannii | IMP-4 | 1 |
| P. aeruginosa | IMP-7 | 3 |
| E. cloacae | IMP-8 | 1 |
| K. pneumoniae | IMP-8 | 1 |
| P. aeruginosa | IMP-14 | 1 |
| P. aeruginosa | IMP-18 | 1 |
| P. mirabilis | IMP-27 | 1 |
| A. baumannii | NDM* | 3 |
| Citrobacter sp. | NDM | 4 |
| E. cloacae | NDM | 3 |
| E. coli | NDM | 12 |
| K. pneumoniae | NDM | 18 |
| M. morganii | NDM | 1 |
| P. mirabilis | NDM | 1 |
| P. rettgeri | NDM | 2 |
| S. seftenberg | NDM | 1 |
| S. marcescens | NDM | 1 |
| E. coli | NDM-5 | 2 |
| E. coli | NDM-6 | 1 |
| E. cloacae | VIM * | 1 |
| K. pneumoniae | VIM | 6 |
| P. aeruginosa | VIM | 5 |
| A. baumannii | VIM-2 | 2 |
| P. aeruginosa | VIM-2 | 8 |
| P. aeruginosa | VIM-3 | 1 |
| P. aeruginosa | VIM-4 | 1 |
| P. aeruginosa | VIM-7 | 1 |
| P. aeruginosa | SPM* | 2 |
| Class D carbapenemases (n = 35) | | |
| A. baumannii | OXA-23 | 8 |
| A. baumannii | OXA-40 | 3 |
| E. aerogenes | OXA-48 | 1 |
| K. pneumoniae | OXA-48 | 12 |
| A. baumannii | OXA-58 | 2 |
| A. baumannii | OXA-72 | 1 |
| K. ozaenae | OXA-181 | 1 |
| K. pneumoniae | OXA-181 | 5 |
| K. pneumoniae | OXA-232 | 2 |

TABLE 1.3

Isolates with Two Carbapenemases and Non-Carbapenemase Isolates

| Organism | | |
|---|---|---|
| Two Carbapenemases (n = 7) | | |
| A. baumannii | OXA-23, OXA-40 | 1 |
| A. baumannii | OXA-23, NDM | 1 |
| K. pneumoniae | OXA-181, NDM | 2 |
| K. pneumoniae | OXA-232, NDM | 1 |
| E. cloacae | KPC-18, VIM-1 | 2 |
| Non-carbapanemases (n = 50) | | |
| C. freundii | High chromosomal AmpC | 1 |
| E. aerogenes | High chromosomal AmpC +/− ESBL* | 4 |
| E. cloacae | High chromosomal AmpC | 7 |
| E. coli | High chromosomal AmpC | 5 |
| E. coli | Plasmid-mediated AmpC* | 6 |
| M. morganii | High chromosomal AmpC | 2 |
| M. morganii | Wildtype AmpC | 1 |
| K. oxytoca | Plasmid-mediated AmpC | 1 |
| K. pneumoniae | Plasmid-mediated AmpC +/− ESBL +/− porin mutation | 7 |
| P. mirabilis | Plasmid-mediated AmpC | 1 |
| K. oxytoca | High K1 | 1 |
| K. pneumoniae | SHV | 1 |

TABLE 1.3-continued

Isolates with Two Carbapenemases
and Non-Carbapenemase Isolates

| Organism | | |
|---|---|---|
| K. pneumoniae | ESBL +/− porin mutation | 7 |
| K. pneumoniae | porin mutation | 2 |
| S. marcescens | ESBL | 1 |
| E. coli | High TEM-1 | 1 |
| E. coli | ESBL | 3 |

Mechanism Key*
KPC = KPC-like, KPC-2 or KPC-3
NDM = NDM-like or NDM-1
VIM = VIM-like or VIM-1
SPM = SPM-like or SPM-1
Plasmid-mediated AmpC = ACT-1, ACT-like, CMY (CMY-like, CMY-2, CMY-2-like) CMY-16, DHA-1, DHA-like, FOX-1, FOX-5, LAT-4, MIR-like, MOX-1
ESBL = CTX-M-1, CTX-M-2CTX-M-9, CTX-M-12, CTX-M14, CTX-M-15, CTX-M-15-like, CTX-M-28, SHV ESBL, SHV-5, SHV-5-like, SHV-12, SHV-12-like, SHV-18, TEM ESBL, OXA-45

Example 11.3

Sensitivity of Detection of All Carbapenemases

Given the extreme diagnostic difficulty of some of the test isolates, these results obtained for both BD Phoenix™ CPO Detect and bioMérieux Rapidec® Carba NP in terms of overall sensitivities for detection of all types of carbapenemases were outstanding.

The BD Phoenix™ CPO Detect achieved a sensitivity of 97.1% (236 of 243 CPOs detected). Sensitivity for the bioMérieux Rapidec® Carba NP test was 98.8% using Interpretation 1 and 97.1% using Interpretation 2.

Example 11.4

Sensitivity of Detection of Molecular Class of Carbapenemase

Sensitivities of detection of both BD Phoenix™ CPO Detect and bioMérieux Rapidec® Carba NP were very good with respect to each molecular class of carbapenemases. The BD Phoenix™ CPO Detect aborted its panel for one isolate P. aeruginosa G15303. In a routine clinical lab, a repeat test would be immediately performed for this isolate to yield a result.

Sensitivity of Class A Carbapenemase Detection

The BD Phoenix™ CPO Detect achieved 97.3% (107/110 isolates) sensitivity of detection of Class A carbapenemase producers. The bioMérieux Rapidec® Carba NP achieved 100.0% (110/110 isolates) sensitivity using Interpretation 1 and 98.2% (108/110 isolates) sensitivity using Interpretation 2. The detection of 97.3% of Class A producers in this highly challenging evaluation is a signification accomplishment.

In regard to the BD Phoenix™ CPO Detect's sensitivity of Class A detection, three KPC (Class A) producers yielded false negative results, which were:

C. freundii G1706—This isolate had a relatively low ertapenem MIC of 1 μg/ml (most CPOs were >1 μg/ml). The meropenem MIC (0.25 μg/ml) was unusually low for a CPO. The imipenem MIC was notably elevated (2 μg/ml) but not in the resistant range. This type of CPO is difficult to detect with tests that cannot detect carbapenem hydrolysis. It would not have aroused suspicion if meropenem was the only carbapenem tested.

KPC-4-producing K. pneumoniae G1511-KPC-4 is a weakly active enzyme. Because the MICS were distinctly elevated (ertapenem>1; imipenem 4; meropenem 2 μg/ml), the isolate would not be falsely reported as susceptible to carbapenems. This is an extremely difficult isolate for most phenotypic tests to confirm as a CPO.

K. oxytoca 0147—This isolate had high, off-scale carbapenem MICS of ertapenem>1; imipenem>8; meropenem>8 μg/ml and would not be falsely reported as susceptible to carbapenems. It is unclear why its potential for carbapenemase production was not recognized.

These three isolates are less common types of CPOs for which there may currently be only limited data available to generate a strong algorithm. Two of them would be unequivocally reported as nonsusceptible to carbapenems and therefore would not be candidates for carbapenem therapy.

Sensitivity of Class B Carbapenemase Detection

The BD Phoenix™ CPO Detect achieved 95.6% (87/91 isolates) sensitivity of detection of Class B producers. The bioMérieux Rapidec® Carba NP achieved 98.9% (90/91 isolates) sensitivity using Interpretations 1 and 2.

In regard to the BD Phoenix™ CPO Detect's sensitivity of Class B detection, four Class B (metallo-β-lactamase) producers yielded false negative results. Three (two P. aeruginosa and one P. mirabilis) had high carbapenem MICS and would not have been reported as carbapenem-susceptible. Their phenotypes resembled those conferred by non-carbapenemase mechanisms, which may have made them difficult to recognize as CPOs. The fourth isolate, E. cloacae G1691 had a low MEM MIC and may not have aroused suspicion as a CPO if this was the only carbapenem tested.

The four isolates were:

IMP-8-producing E. cloacae G1691: despite the elevated MICS of ERT>1; IMP 4; and MEM 0.5 μg/ml, the unusual phenotype of this organism, especially the low but elevated MEM MIC, may have contributed to the false negative test.

VIM-producing P. aeruginosa G15557 and VIM-2-producing P. aeruginosa: these had identical phenotypes— ERT>1; IMP>8; MEM 4 μg/ml. This is the frequently encountered phenotype associated with diminished OprD porin production. This may have contributed to the false negative test.

The fourth isolate was IMP-27-producing Proteus mirabilis: the carbapenem MICS of ERT>1; IMP 8; MEM>8 μg/ml were distinctly different from the intrinsic reduced susceptibility of this species to imipenem but not other carbapenems. The atypical phenotype should have triggered suspicion of carbapenemase production but IMP-27 is an extremely difficult carbapenemase to detect with phenotypic tests.

Sensitivity of Class D Carbapenemase Detection

Both BD Phoenix™ CPO Detect and the bioMérieux Rapidec® Carba NP were excellent for detecting Class D carbapenemase production by Acinetobacter spp. and Enterobacteriaceae.

The BD Phoenix™ CPO Detect achieved 100% (35/35 isolates) sensitivity of detection of Class D producers. This is particularly unprecedented given that Class D produces present the most difficult diagnostic challenge as Class D carbapenemases are only weakly active and very difficult/almost impossible to detect with some current tests.

The bioMérieux Rapidec® Carba NP achieved 94.3% (33/35 isolates) using Interpretations 1 and 2. The bioMérieux Rapidec® Carba NP missed two OXA-48-like producers.

Sensitivity of Detection of Isolates Producing Two Carbapenemases

All seven isolates producing two carbapenemases were reported as carbapenemase positive by both BD Phoenix™ CPO Detect and the bioMérieux Rapidec® Carba NP.

Example 11.5

Specificity of Detection of All Carbapenemases

The extremely challenging nature of the negative control isolates contributed to the lower than usual specificities. The BD Phoenix™ CPO Detect yielded 68.6% 35/51 isolates) specificity. The bioMérieux Rapidec® Carba NP yielded a specificity of 60.8% (31/51 isolates) using Interpretation 1 and a specificity of 78.4% (40/51 isolates) using Interpretation 2.

Both tests had problems with both AmpC producers and non-AmpC producers. For AmpC producers, the BD Phoenix™ CPO Detect yielded a specificity of 74.3% (26/35 isolates), and the bioMérieux Rapidec® Carba NP yielded a specificity of 57.1% (20/35 isolates) using Interpretation 1 and a specificity of 77.1% (27/35 isolates) using Interpretation 2.

For other non-AmpC producers, the BD Phoenix™ CPO Detect yielded a specificity of 43.8% (7/16 isolates), and the bioMérieux Rapidec® Carba NP yielded a specificity of 62.5% (10/16 isolates) using Interpretations 1 and 2.

Table 2 lists the isolates yielding falsely positive results, their resistance mechanism characterizations and their carbapenem MICS. False positive results due to high level AmpC production are a problem for many carbapenemase detection tests. High level AmpC production on its own does not explain the false positive results with the BD Phoenix™ CPO Detect test. The test gave correctly negative calls for the very high level AmpC producers E. coli G1634 and G1700. This tends to eliminate AmpC production as the explanation for the false positive results with other AmpC producers. Similarly, it is unlikely that the false positive results for the ESBL producers were caused by ESBL production in itself. A more likely explanation is the false positive results for these isolates were due to porin mutations. A remotely possible explanation is production of extended spectrum AmpCs that hydrolyze carbapenems. Another possible explanation is inhibition by the chelator in Class B carbapenemase detection tests. This could cause ESBL or AmpC producers to test falsely positive for Class B carbapenemase production.

The identifications of the isolates listed in Table 2 add support to the likelihood of porin mutations as an explanation. Fifteen of the 17 isolates were K. pneumoniae, E. coli and Enterobacter spp. Of these, K. pneumoniae is the most common member of the Enterobacteriaceae for which porin mutations elevate carbapenem MICS, especially MICS ertapenem and meropenem. E. coli and Enterobacter spp. also have relatively high propensities for porin mutations. In Table 2, all isolates have an elevated off-scale MIC of at least one carbapenem and most have off-scale MICS of all carbapenems. Confirmation of porin mutations is usually not attempted because it is tedious, expensive and technically difficult. Distinguishing between porin mutants and carbapenemase producers is best achieved by tests that detect the presence or absence of carbapenem hydrolysis.

The false positive result for P. mirabilis G1745 could possibly be corrected with a software edit. This isolate is typical of the species with a characteristically higher MIC of imipenem than ertapenem and meropenem. The elevated MIC of only imipenem for this isolate is unlikely to be caused by a carbapenemase.

TABLE 2

Isolates Yielding Falsely Positive Carbapenemase Detection Results

| Species | Strain | Mechanisms | MIC in µg/ml | | |
|---|---|---|---|---|---|
| | | | Ertapenem | Imipenem | Meropenem |
| E. aerogenes | G1614 | High AmpC | >1 | >8 | >8 |
| E. aerogenes | G1648 | High AmpC | >1 | >8 | >8 |
| E. cloacae | G1637 | High AmpC | >1 | >8 | >8 |
| E. cloacae | G1735 | High AmpC, OMP mutant? | >1 | >8 | >8 |
| E. coli | G1693 | High AmpC, S12like | >1 | >8 | >8 |
| E. coli | G164 | High AmpC | >1 | >8 | >8 |
| E. coli | 0058 | ESBL | >1 | ≤0.25 | 0.5 |
| E. coli | 0086 | CTX-M-9 | >1 | >8 | >8 |
| K. pneumoniae | 0044 | CTX-M-15, TEM-1, SHV-1 | >1 | >8 | >8 |
| K. pneumoniae | 0042 | CTX-M-28, OmpK35, OmpK36 | >1 | 1 | 4 |
| K. pneumoniae | 0047 | OmpK35 | >1 | >8 | >8 |
| K. pneumoniae | 0079 | CTX-M-14, OmpK35 | >1 | >8 | >8 |
| K. pneumoniae | G1758 | CLSI MHT negative control | >1 | 4 | 1 |
| K. pneumoniae | 0109 | CTX-M-15, TEM-1, SHV-1 | >1 | 4 | 8 |
| K. pneumoniae | 0043 | SHV-12, OmpK36 | >1 | >8 | >8 |
| M. morganii | G1751 | High AmpC | >1 | 4 | 4 |
| P. mirabilis | G1745 | CMY, TEM-1-like | ≤0.25 | 8 | ≤0.125 |

Example 11.6

Carbapenemase Classification

The classification of carbapenemases into molecular Classes A, B and D is of therapeutic importance. It is also useful for infection control, epidemiology and research. Four BD Phoenix™ CPO Detect algorithms were analyzed for their ability to classify types of carbapenemase production.

The bioMérieux Rapidec® Carba NP test is incapable of carbapenemase classification. The ability of the BD Phoenix™ CPO Detect to classify carbapenemases is currently unique. There are no standards against which to evaluate this type of testing. In practice, any correct classification of a carbapenemase is of potential clinical benefit.

Figure 32:
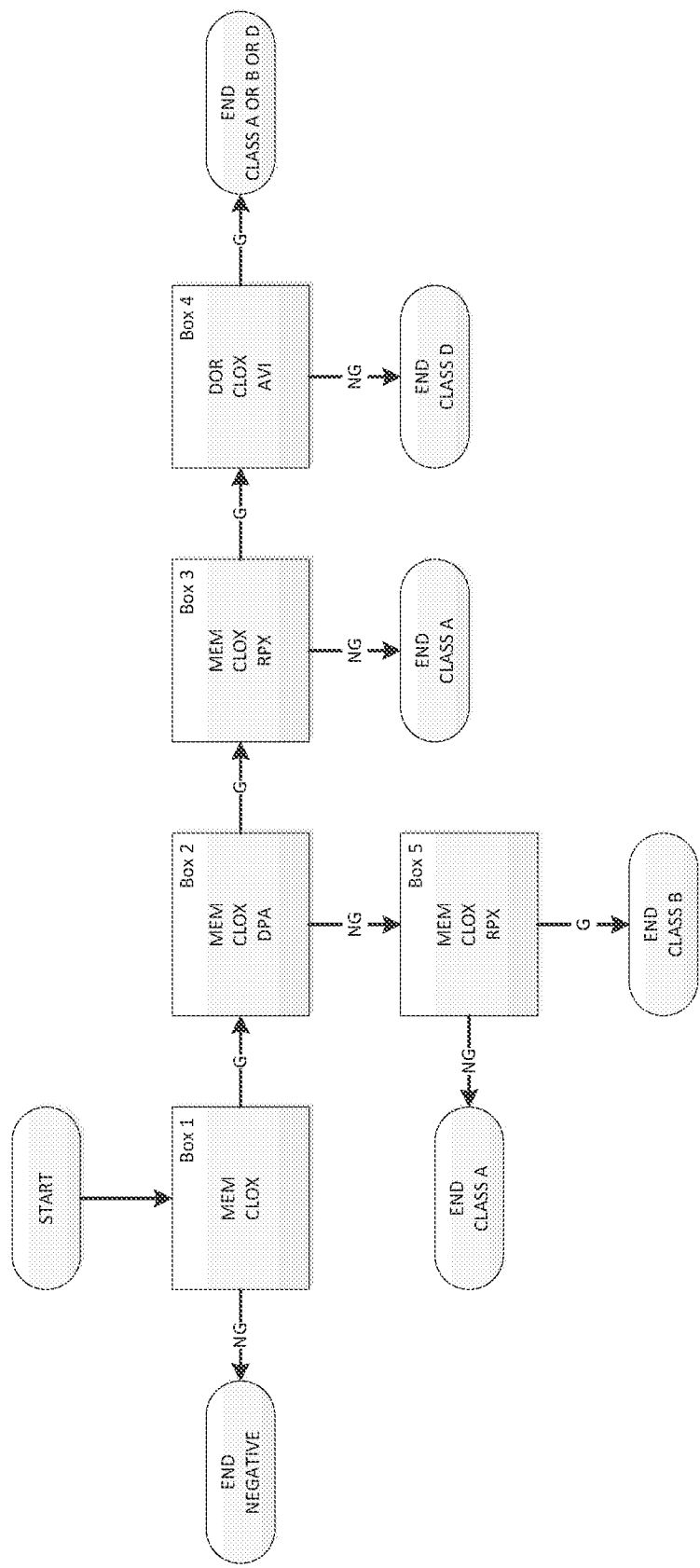
FIG. 32 shows a flowchart of an embodiment of an algorithm for classification of Enterobacteriaceae into Class A, B or D.
Figure 33:
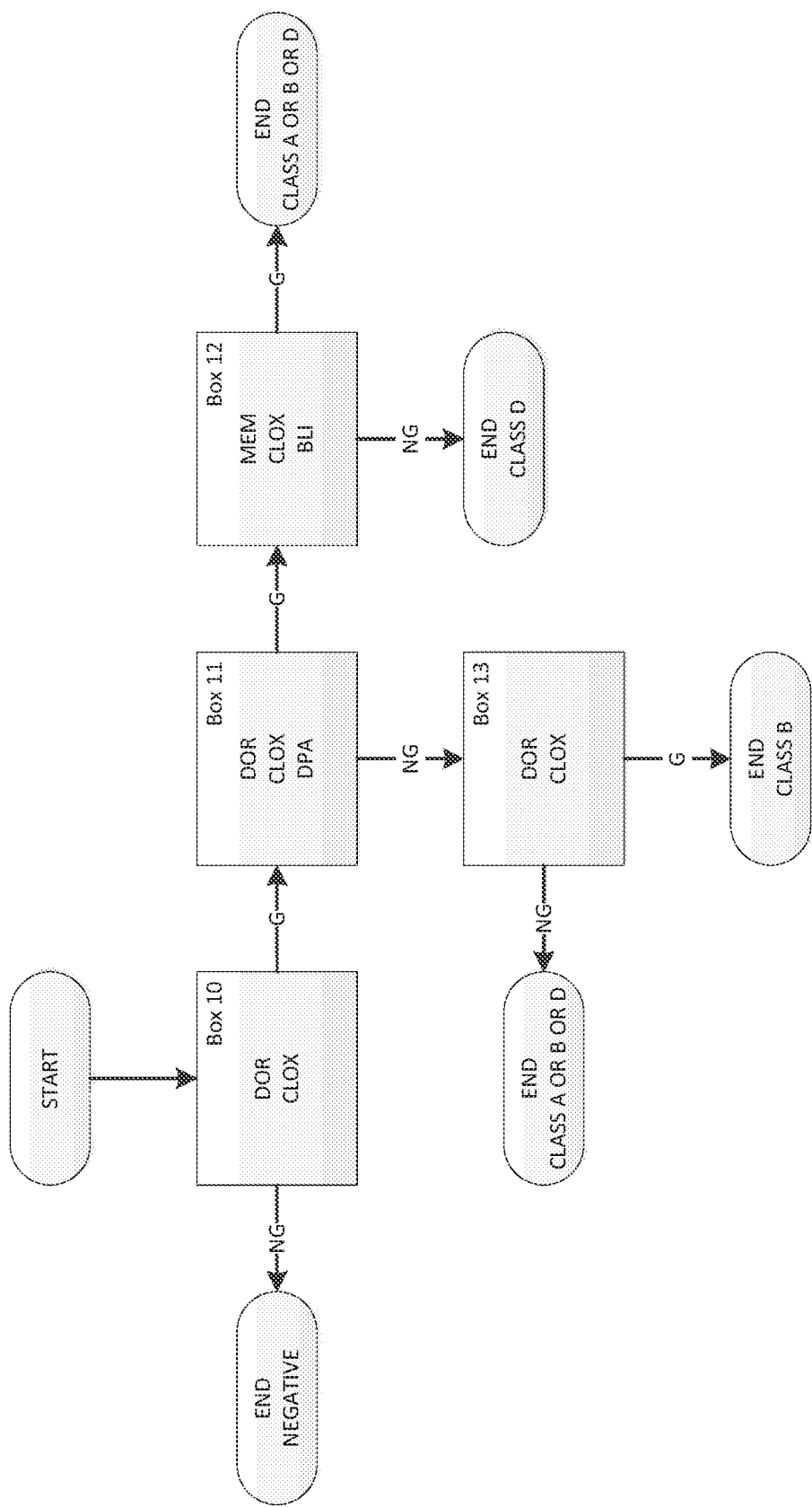
FIG. 33 shows a flowchart of an embodiment of an algorithm for classification of no fermenters into Class B or D.
Figure 34:
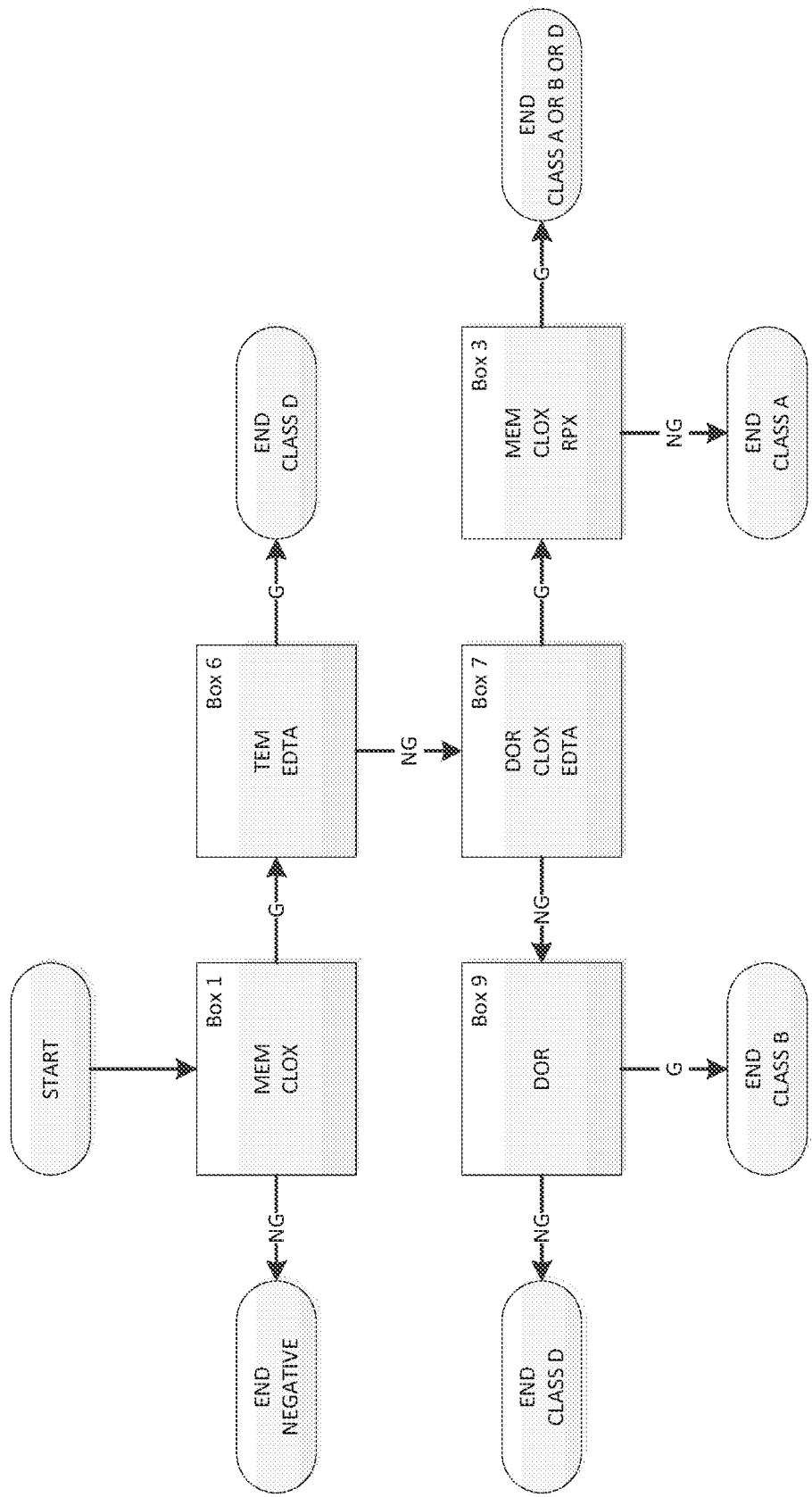
FIG. 34 shows a flowchart of an embodiment of an algorithm for classification of Enterobacteriaceae into Class A, B or D.
Figure 35:
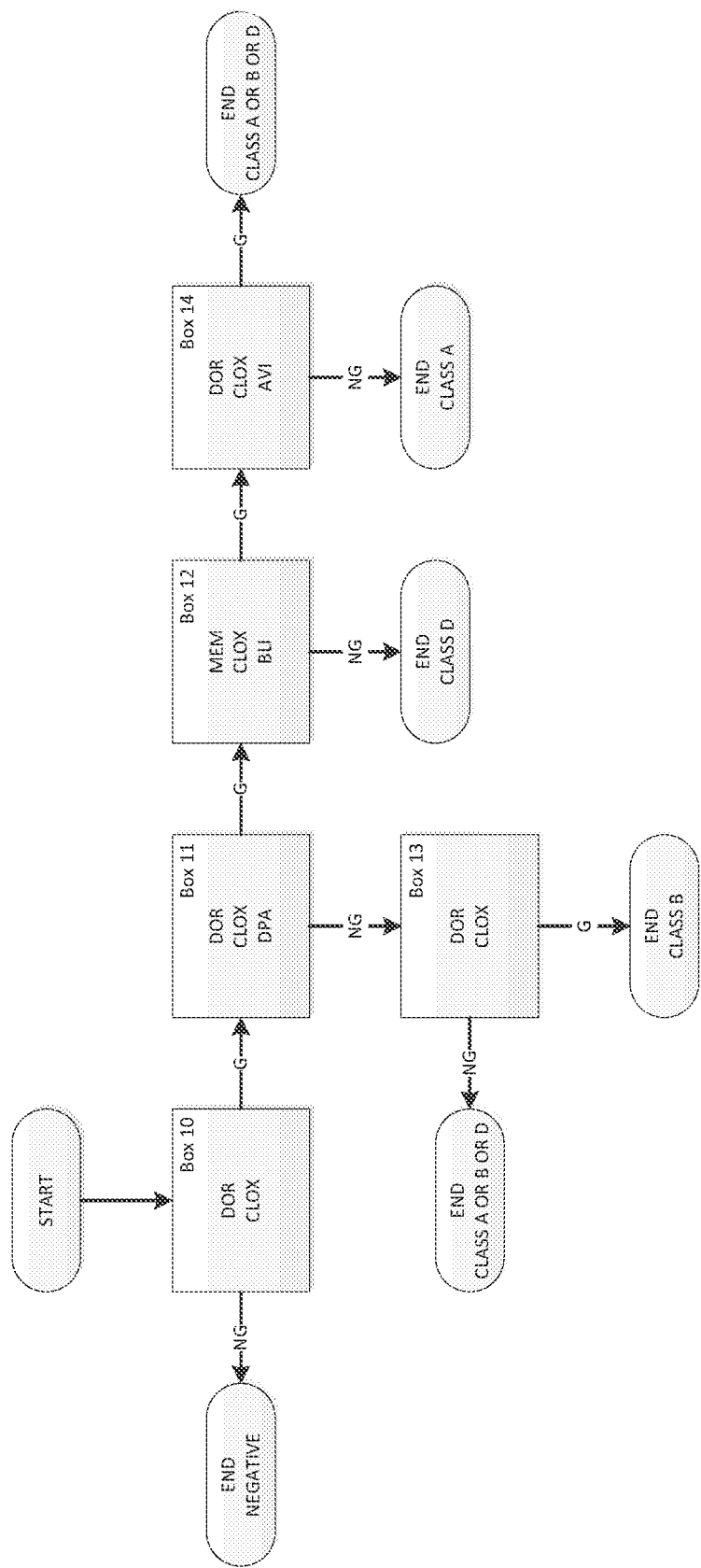
FIG. 35 shows a flowchart of an embodiment of an algorithm for classification of nonfermenters into Class A, B or D.

Algorithm 1 classified Enterobacteriaceae into Class A, B or D (FIG. 32). Algorithm 1 classified nonfermenters into Class B or D only (FIG. 33). Algorithm 2 classified both Enterobacteriaceae (FIG. 34) and nonfermenters (FIG. 35) into Class A, B or D. Algorithm 3 is the same as Algorithm 1 except that the BD Phoenix™ CPO Detect is allowed to give a "no answer" result (FIG. 26 for Enterobacteriaceae and FIG. 29 for nonfermenters). Algorithm 4 is the same as Algorithm 2 except that the BD Phoenix™ CPO Detect is allowed to give a "no answer" result (FIG. 27 for Enterobacteriaceae and FIG. 30 for nonfermenters)

Algorithms 1-4 (FIG. 26, FIG. 27, FIG. 29, FIG. 30 and FIG. 32-FIG. 35) are exemplary and non-limiting. The antibiotic concentrations provided in Algorithms 1-4 (FIG. 26, FIG. 27, FIG. 29, FIG. 30 and FIG. 32-FIG. 35) was within the antibiotic concentration ranges disclosed in Table 2.1. In Algorithms 1-4 (FIG. 26, FIG. 27, FIG. 29, FIG. 30 and FIG. 32-FIG. 35) and Table 2.1, the concentration of CLOX was 100 µg/mL, DPA was 178 µg/mL, AVI was 4 µg/mL, BLI was 5 µg/mL, EDTA was 250 µg/mL, RPX was 8 µg/mL.

TABLE 2.1

Antibiotic Concentration Ranges

| Contents | Antibiotic Concentration Range |
|---|---|
| DOR | DOR 0.0625-0.25 (µg/ml) |
| DOR/CLOX | DOR 0.5-4 (µg/ml) |
| DOR/CLOX/AVI (non-fermenter) | DOR 0.03125-16 (µg/ml) |
| DOR/CLOX/AVI (enteric) | DOR 6-240 (µg/mL) |
| DOR/CLOX/DPA | DOR 0.5-2 (µg/ml) |
| DOR/CLOX/EDTA | DOR 0.03125-0.125 (µg/ml) |
| MEM/CLOX #8 | MEM 0.03125-1 (µg/ml) |
| MEM/CLOX #1 | MEM 0.03125-0.125 (µg/ml) |
| MEM/CLOX/BLI | MEM 2-8 (µg/ml) |
| MEM/CLOX/DPA | MEM 0.03125-0.125 (µg/ml) |
| MEM/CLOX/RPX | MEM 0.015625-0.125 (µg/ml) |
| TEM/EDTA | TEM 32-128 (µg/ml) |

Algorithms 1-4 (FIG. 26, FIG. 27, FIG. 29, FIG. 30 and FIG. 32-FIG. 35) operate as previously described in FIG. 25-FIG. 30. For example, each "Box" in Algorithms 1-4 (e.g., Box 1 in FIG. 32) represents a well (or optionally the average of several identical wells) of the detection tests provided herein comprising an input sample comprising one or more bacteria, one or more detection reagents, and one or more antibiotics with/without one or more carbapenemase inhibitors. The detection test result provided to the system is either positive for growth (G) or no growth (NG) in the one or more wells of the detection tests within a defined time frame. Based on the results provided for a queried well, (growth or no growth), the system proceeds to the next query as defined by the algorithm. The system queries the plurality of test results until the system reaches an output point in the algorithm, at which point the system generates an output result.

Table 3 summarizes the algorithm results for all isolates except the seven dual carbapenemase producers. The good results are on the left of the Table 3, i.e., correct classifications, correct negative results, unclassified carbapenemases (Not Typed), and total correct detections whether classified or not (i.e. Assigned to column "A, B, D or Untyped"/Not Typed).

TABLE 3

Classification of Carbapenemases for Isolates Producing a Single Carbapenemase

| | Numbers of Correct Results and Percent Correct | | | | | Assigned to | Numbers of Incorrect Results | | | | | |
|---|---|---|---|---|---|---|---|---|---|---|---|---|
| Algorithm | A | B | D | Neg | Not Typed | A, B, D or Untyped | A | B | D | Neg | Not Typed | No Answer |
| Alg 1 | 90 | 63 | 28 | 33 | 37 | 217 | 3 | 5 | 20 | 7 | 1 | 0 |
| | 81.2% | 69.2% | 80.0% | 64.7% | | 91.9% | | | | | | |
| Alg 2 | 91 | 63 | 31 | 33 | 35 | 220 | 1 | 13 | 4 | 7 | 9 | 0 |
| | 82.7% | 69.2% | 88.6% | 64.7% | | 93.2% | | | | | | |
| Alg 3 | 90 | 63 | 28 | 33 | 16 | 197 | 3 | 5 | 20 | 7 | 0 | 22 |
| | 81.2% | 69.2% | 80.0% | 64.7% | | 83.5% | | | | | | |
| Alg 4 | 91 | 63 | 31 | 33 | 29 | 214 | 1 | 13 | 4 | 7 | 3 | 12 |
| | 82.7% | 69.2% | 88.6% | 64.7% | | 90.7% | | | | | | |
| No. | 110 | 91 | 35 | 51 | | 236 | | | | | | |

All algorithms performed well identifying at least 80% of Class A-producing CPOs. Algorithms 2 and 4, which correctly classified 91 of 110 Class A producers (82.7%) were marginally more accurate than Algorithms 1 and 3 (81.2%). There was a very low incidence of misclassifications and, of high clinical importance, the isolates misclassified as Class A producers were not Class B producers. Only one isolate, OXA-40-producing *A. baumannii* G1734, generated a falsely positive Class A result with Algorithms 2 and 4. Three isolates, CTX-M-9-producing *E. coli* 0086, CMY-producing *P. mirabilis* G1745 and AmpC hyperproducing *M. morganii* G1751 generated falsely positive Class A results with Algorithms 1 and 3. The high level accuracy of identifying Class A-producing CPOs to indicate possible use of ceftazidime/avibactam therapy meets an important and currently unmet clinical need.

All algorithms correctly classified 63 of 91 Class B producers (69.2%). This is valuable for identifying when ceftazidime/avibactam should not be used. It is a result that can save lives by preventing patients from receiving ineffective ceftazidime/avibactam therapy. The consequences of a falsely positive Class B classification include a possible delay in initiating effective ceftazidime/avibactam therapy or the initiation of alternative anti-CPO therapy. In general, these would be non-life-threatening consequences that may apply only until additional testing (e.g. molecular) is performed. Algorithms 2 and 4 with 13 falsely positive results had more than twice as many false positives as Algorithms 1 and 3. Overall, the performance of BD Phoenix™ CPO Detect in identifying Class B producers provides considerable potential for clinical benefit and minimal potential for placing a patient at serious risk.

Algorithm 2 correctly classified the most Class D producers with 31 of 35 isolates (88.6%). Of all carbapenemases, these are the most difficult to detect, let alone to classify. The performance of all algorithms with Class D producers was superb. Falsely positive Class D calls might lead to unnecessary isolation. Algorithms 2 and 4, with four incorrect calls respectively were superior to algorithms 1 and 3 which each had 20 falsely positive calls. The "no answer" result of algorithms 3 and 4 is also unhelpful in that it confers neither benefit nor harm.

All algorithms correctly reported 33 (64.7%) of the 51 carbapenemase-negative isolates as negative. In routine clinical performance, where the diagnostic difficulty should be considerably lower than in this study, the percent of correct negative results should be significantly higher.

In summary, all algorithms correctly classified at least 80% of the Class A and Class D carbapenemases and almost 70% of Class B carbapenemases. This is an important achievement and a major advance in phenotypic testing.

Overall, Algorithm 2 was marginally better than the other algorithms for correctly classifying carbapenemases and it also provided the most positive tests.

The carbapenemase-producing and non-carbapenemase-producing isolates that caused incorrect classifications and their carbapenem MICS are shown in Table 4.1 and Table 4.2, respectively. In perspective of the very difficult-to-detect CPOs this study, a false negative rate of seven of the 244 CPOs that were tested (2.9%) is not alarming. No carbapenemase detection test is perfect but it is desirable to reduce the false negative rate to 1%. Apart from these seven falsely negative results with each algorithm, the other inaccurate classifications have minimal potential to cause harm.

TABLE 4.1

Carbapenemase-Producing Isolates Incorrectly Classified by Algorithm

| Carbapenemase Producers | | Isolate | Algorithm* | | | | MIC (µg/ml) | | |
|---|---|---|---|---|---|---|---|---|---|
| Organism | Mechanism | No. | 1 | 2 | 3 | 4 | ERT | IPM | MEM |
| E. cloacae | KPC-3, TEM-1 | 0032 | + | B | + | B | >1 | 4 | 2 |
| A. baumannii | OXA-58 | 0052 | B | B | B | B | >1 | >8 | 8 |
| K. ozaenae | KPC | 0096 | + | B | + | B | >1 | >8 | >8 |
| K. pneumoniae | KPC-3 | 0113 | D | U | D | U | >1 | >8 | >8 |
| E. coli | NDM | 0119 | U | D | N | D | >1 | >8 | >8 |
| E. coli | NDM-6 | 0137 | U | D | N | D | >1 | >8 | >8 |
| P. mirabilis | KPC | 0155 | D | U | D | N | >1 | >8 | 8 |
| P. mirabilis | KPC | 0156 | B | B | B | B | 0.5 | 8 | 0.25 |
| P. aeruginosa | KPC-5 | G15 | U | + | U | + | >1 | >8 | >8 |
| S. marcescens | KPC | G153 | D | U | D | N | >1 | >8 | >8 |
| K. pneumoniae | KPC-8 | G157 | D | U | D | U | >1 | >8 | >8 |
| K. pneumoniae | KPC-8 | G158 | D | U | D | U | >1 | >8 | >8 |
| K. oxytoca | KPC | G1640 | B | U | B | U | >1 | >8 | >8 |
| K. pneumoniae | KPC-2, SHV-5-like | G1675 | D | U | D | U | >1 | >8 | >8 |
| K. pneumoniae | KPC | G1725 | D | U | D | U | >1 | >8 | >8 |
| A. baumannii | OXA-40 | G1734 | U | A | U | A | >1 | >8 | >8 |
| K. oxytoca | KPC | 0147 | neg | neg | neg | neg | >1 | >8 | >8 |
| P. aeruginosa | VIM-2 | G15019 | neg | neg | neg | neg | >1 | >8 | 4 |
| K. pneumoniae | KPC-4 | G1511 | neg | neg | neg | neg | >1 | 4 | 2 |
| P. mirabilis | IMP-27 | G15185 | neg | neg | neg | neg | >1 | 8 | >8 |
| P. aeruginosa | VIM-like | G15557 | neg | neg | neg | neg | >1 | >8 | 4 |
| E. cloacae | IMP-8 | G1693 | neg | neg | neg | neg | 0.5 | 4 | 0.5 |
| C. freundii | KPC | G1706 | neg | neg | neg | neg | 1 | 2 | 0.25 |

*Algorithms, 1, 2, 3, 4; Results, +, correct classification; A, B, and D are incorrect molecular classifications; U, untyped carbapenemase; N, no result; neg, falsely negative result

TABLE 4.2

Non-Carbapenemase-Producing Isolates Incorrectly Classified by Algorithms

| Non-Carbapenemase Producers | | Isolate | Algorithm* | | | | MIC (µg/ml) | | |
|---|---|---|---|---|---|---|---|---|---|
| Organism | Mechanism | No. | 1 | 2 | 3 | 4 | ERT | IPM | MEM |
| K. pneumoniae | CTX-M-28, OmpK36, OmpK35 | 0042 | D | U | D | N | >1 | 1 | 4 |
| K. pneumoniae | CTX-M-15, TEM-1, SHV-1, | 0044 | D | U | D | N | >1 | >8 | >8 |
| K. pneumoniae | OmpK35 | 0047 | D | U | D | N | >1 | >8 | >8 |
| E. coli | ESBL | 0058 | D | D | D | D | >1 | ≤0.25 | 0.5 |
| E. aerogenes | High AmpC | G1614 | D | B | D | B | >1 | >8 | >8 |
| E. cloacae | High AmpC | G1637 | U | B | N | B | >1 | >8 | >8 |
| E. coli | High AmpC, SHV-12-like | G164 | D | B | D | B | >1 | >8 | >8 |
| E. aerogenes | High AmpC | G1648 | D | U | D | N | >1 | >8 | >8 |
| E. coli | High AmpC | G1693 | D | B | D | B | >1 | >8 | >8 |
| M. morganii | High AmpC | G1751 | A | U | A | N | >1 | 4 | 4 |

TABLE 4.2-continued

Non-Carbapenemase-Producing Isolates Incorrectly Classified by Algorithms

| Non-Carbapenemase Producers | | Isolate | Algorithm* | | | | MIC (µg/ml) | | |
|---|---|---|---|---|---|---|---|---|---|
| Organism | Mechanism | No. | 1 | 2 | 3 | 4 | ERT | IPM | MEM |
| K. pneumoniae | SHV-12, OmpK36 | 0043 | B | B | B | B | >1 | >8 | >8 |
| K. pneumoniae | CTX-M-14, DHA-1, OmpK35 | 0079 | D | U | D | U | >1 | >8 | >8 |
| E. coli | CTX-M-9 | 0086 | A | B | A | B | >1 | >8 | >8 |
| K. pneumoniae | CTX-M-15, TEM-1, SHV-1 | 0109 | D | U | D | U | >1 | 4 | 8 |
| K. pneumoniae | CMY-2-like | G1685 | D | U | D | N | >1 | >8 | >8 |
| E. cloacae | High AmpC | G1735 | B | B | B | B | >1 | >8 | >8 |
| P. mirabilis | CMY-like, TEM-1-like | G1745 | A | B | A | B | ≤0.25 | 8 | ≤0.125 |
| K. pneumoniae | MHT negative control | G1758 | D | B | D | B | >1 | 4 | 1 |

*Algorithms, 1, 2, 3, 4; Results, +, correct classification; A, B, and D are incorrect molecular classifications; U, untyped carbapenemase; N, no result; neg, falsely negative result Example 11.7

Algorithm Performance for Nonfermenters Versus Enterobacteriaceae

The algorithms described in Example 11.6 were tested for their ability to classify nonfermenters and Enterobacteriaceae producing a single carbapenemase. Nonfermenters such as P. aeruginosa and A. baumannii can be unsuspected reservoirs of Class A and Class B carbapenemases and A. baumannii also possesses intrinsic Class D carbapenemases and can acquire other Class D carbapenemases that are transmissible. Accurate detection of carbapenemases produced by nonfermenters is an important but technically difficult challenge. This is because other mechanisms of carbapenem resistance can produce the same phenotypes as carbapenemases.

As shown in Table 5.1 and Table 5.2, classification of the carbapenemases of Enterobacteriaceae may have achieved a higher level of accuracy than for the nonfermenters. However, the comparison was not an ideal one as there were differences between each organism group in their numbers of isolates and types of β-lactamase production. This is reflected in the very different numbers obtained for Class A producers (5 for nonfermenters versus 105 for Enterobacteriaceae), negative control isolates (0 for nonfermenters versus 51 for Enterobacteriaceae), and total numbers of CPOs (51 for nonfermenters versus 185 for Enterobacteriaceae).

TABLE 5.1

Classification of Carbapenemases of Nonfermenters Producing a Single Carbapenemase

| | Correct Numbers and Percent of Results | | | | | Assigned to | Incorrect | | | | | |
|---|---|---|---|---|---|---|---|---|---|---|---|---|
| Algorithm | A | B | D | Neg | Not Typed | A, B, D, or Untyped | A | B | D | Neg | Not Typed | No Answer |
| 1 | 0 | 19 61.3% | 11 78.6% | 0 | 17 | 47 92.2% | 0 | 1 | 1 | 2 | 0 | 0 |
| 2 | 5 | 19 61.3% | 11 78.6% | 0 | 11 | 46 90.2% | 1 | 1 | 1 | 2 | 0 | 0 |
| 3 | 0 | 19 61.3% | 11 78.6% | 0 | 15 | 45 88.2% | 0 | 1 | 1 | 2 | 0 | 2 |
| 4 | 5 | 19 61.3% | 11 78.6% | 0 | 9 | 44 86.3% | 1 | 1 | 1 | 2 | 0 | 2 |
| No. | 5 | 31 | 14 | 0 | | 51 | | | | | | |

TABLE 5.2

Classification of Carbapenemases of Enterobacteriaceae Producing a Single Carbapenemase

| | Correct Numbers and Percent of Results | | | | | Assigned to | Incorrect | | | | | |
|---|---|---|---|---|---|---|---|---|---|---|---|---|
| Algorithm | A | B | D | Neg | Not Typed | A, B, D, or Untyped | A | B | D | Neg | Not Typed | No Answer |
| 1 | 90 85.7% | 44 73.3% | 17 77.3% | 33 64.7% | 20 | 171 92.4% | 3 | 4 | 19 | 5 | 1 | 0 |
| 2 | 86 81.9% | 44 73.3% | 20 90.9% | 33 64.7% | 24 | 175 94.6% | 0 | 12 | 3 | 5 | 9 | 0 |

TABLE 5.2-continued

Classification of Carbapenemases of Enterobacteriaceae Producing a Single Carbapenemase

| Algorithm | Correct Numbers and Percent of Results | | | | Not Typed | Assigned to A, B, D, or Untyped | Incorrect | | | | No Answer |
|---|---|---|---|---|---|---|---|---|---|---|---|
| | A | B | D | Neg | | | A | B | D | Neg | Not Typed | |
| 3 | 90 | 44 | 17 | 33 | 1 | 152 | 3 | 4 | 19 | 5 | 0 | 20 |
| | 85.7% | 73.3% | 77.3% | 64.7% | | 82.2% | | | | | | |
| 4 | 86 | 44 | 20 | 33 | 20 | 170 | 0 | 12 | 3 | 5 | 3 | 10 |
| | 81.9% | 73.3% | 90.9% | 64.7% | | 91.9% | | | | | | |
| No. | 105 | 60 | 22 | 51 | | 185 | | | | | | |

Algorithm 2 appeared to be the best overall algorithm for both groups of organisms. It performed well with Class A producers, correctly classifying all five in the nonfermenter group and 81.9% in the Enterobacteriaceae group. It correctly classified the Class B producers of the Enterobacteriaceae (73.3% correct) better than the nonfermenters (61.3%) and was also more accurate in classifying the Class D producers of the Enterobacteriaceae (90.9% versus 78.6%).

Example 11.7

Algorithm Performance for Isolates Producing Two Carbapenemases

The seven isolates producing two carbapenemases were:
A. baumannii 0063: OXA-23+OXA-40
A. baumannii 0083: OXA-23+NDM
K. pneumoniae 0068: OXA-181+NDM
K. pneumoniae 0153: OXA-232+NDM
K. pneumoniae G15406: OXA-181+NDM
E. cloacae G6809: KPC-18+VIM-1
E. cloacae G6810: KPC-18+VIM-1.

The distribution of carbapenemase classifications for each algorithm is shown in Table 6.

TABLE 6

Classification of Carbapenemases of Seven Isolates Producing Two Carbapenemases

| Algorithm | B | D | Not Typed | No Answer |
|---|---|---|---|---|
| 1 | 0 | 1 | 6 | 0 |
| 2 | 1 | 4 | 2 | 0 |
| 3 | 0 | 1 | 1 | 5 |
| 4 | 1 | 4 | 2 | 0 |

Each isolate was correctly reported as carbapenemase-positive in the positive/negative phase of testing. Algorithms 1, 2 and 4 assigned all isolates to either a molecular class or to the carbapenemase-positive, untyped category. Algorithms 2 and 4 classified five of the seven isolates as producers of a specific carbapenemase class and algorithms 1 and 3 each assigned only one isolate to a specific class. Algorithm 3 assigned five isolates to the "No Answer" category.

In each case where the algorithm assigned a CPO to a specific class of carbapenemase production, it was the correct class for one of the two carbapenemases or, in the case of A. baumannii 0063 which produced two Class D carbapenemases, it was correct for both carbapenemases. There were not enough isolates to analyze trending of the classifications for dual carbapenemase producers, but there appeared to be a possible preference to assign the carbapenemases to Class D.

Example 11.8

Workflow Comparison

The BD Phoenix™ CPO Detect required less hands-on time than the bioMérieux Rapidec® Carba NP test and involved no wait time as the test requires no operator involvement after loading a panel into the instrument. The BD Phoenix™ CPO Detect hands-on time per test was 1 minute 34 seconds compared to the bioMérieux Rapidec® Carba NP hands-on time per test of 2 minutes 3 seconds for a test that is positive (i.e. completed) after the 30-minute incubation period and 2 minutes 24 seconds for a test that is negative at 30 minutes and therefore requires additional handling and incubation. A summary of the workflow analysis is provided in Table 7.

TABLE 7

Workflow Analysis

| | Time in Hours (h), Minutes (m), Seconds (s) | | |
|---|---|---|---|
| Test Component | BD Phoenix CPO Detect | Rapidec Carba NP 30-minute Test | 2-hour Test |
| Hands-on time per test | 1 m 34 s | 2 m 3 s | 2 m 24 s |
| Hands-on time per 10 tests | 16 m 50 s | 20 m 20 s | 24 m 0 s |
| Wait time | Not applicable | 1 h 5 m | 2 h 35 m |

Example 11.9

Perspectives/Summary/Conclusions

This Example provides the results of a study that was designed to compare the ability of the automated BD Phoenix CPO Detect test and the bioMérieux Rapidec® Carba NP test to detect and classify carbapenemase-producing organisms (CPOs). The BD Phoenix™ CPO Detect is an innovative test that is integrated with susceptibility panels to detect and classify carbapenemases. The bioMérieux Rapidec® Carba NP test is a standalone carbapenemase detection test. The 294 study isolates of Enterobacteriaceae, Pseudomonas aeruginosa and Acinetobacter baumannii were chosen to provide extreme diagnostic difficulty. They had been previously characterized by molecular, phenotypic and biochemical tests for types of β-lactamase production.

Both tests were blinded and performed according to the manufacturers' recommendations.

This study provided an extremely tough assessment of the ability of the BD Phoenix™ CPO Detect and the bioMérieux Rapidec® Carba NP tests to detect carbapenemases. Both tests exhibited very high sensitivity. The detection by the BD Phoenix™ CPO Detect of 100% of Class D-producing CPOs cannot be improved on and should be recognized as a remarkable accomplishment because these are the most difficult of all carbapenemases to detect. The extremely challenging nature of the carbapenemase-negative isolates contributed to lower than usual specificities. In normal clinical use, the types of isolates that caused the falsely positive tests should be encountered infrequently and the specificity should be significantly higher.

The BD CPO Detect can provide two results: a positive/negative result for carbapenemase detection, followed by a classification for positive isolates according to the molecular class of the carbapenemase. In the positive/negative phase of testing, both tests exhibited high sensitivity of carbapenemase detection (97.1% for BD Phoenix™ CPO Detect and 97.1% to 98.8% for the bioMérieux Rapidec® Carba NP test). Both tests exhibited lower than usual specificities due to the extremely challenging nature of the carbapenemase-negative isolates in the study.

The BD Phoenix™ CPO Detect is the first automated test that can detect carbapenemases and can be included in the routine susceptibility test. This is a major technological advance as it avoids reliance on individuals to decide if a carbapenemase detection test should be set up. The test can also assign carbapenemases to different molecular classes. In the current study, the BD Phoenix™ CPO Detect demonstrated high ability to detect and distinguish between CPOs producing Class A and Class B carbapenemases. This diagnostic attribute is clinically important for determining the appropriateness of ceftazidime/avibactam as a potential therapeutic choice. Three of the four investigational algorithms correctly classified over 90% of carbapenemases as either A, B, D and positive untyped carbapenemases, with slightly superior performance by Algorithm 2.

In the classification stage of testing, the BD Phoenix™ CPO Detect correctly classified over 90% of carbapenemases as either Class A, B, D or positive untyped carbapenemases. It demonstrated high ability to detect and distinguish between CPOs producing Class A and Class B carbapenemases, a diagnostic feature that is clinically important for determining the appropriateness of ceftazidime/avibactam as a potential therapeutic choice. The bioMérieux Rapidec® Carba NP test did not have the capability to classify carbapenemases. Overall, the BD Phoenix™ CPO Detect is a completely new type of phenotypic test with a range of capabilities unmatched by currently marketed tests. It represents a significant advance in meeting an important clinical need.

The production of multiple carbapenemases is currently rare and its detection is an important diagnostic and therapeutic challenge. Research is currently hindered by the scarcity of available isolates of this type. Until good tests are available it will be important for current tests to provide results that protect patients from inappropriate ceftazidime/avibactam therapy for infections by multiple carbapenemase producers. In this study the two *E. cloacae* isolates producing KPC-18+VIM-1 were classified as producers of a Class B carbapenemase, thereby correctly contraindicating therapy with ceftazidime/avibactam. The two *A. baumannii* isolates that produced both a Class B and a Class D carbapenemase were both classified as Class D producers. This result should also have prevented a patient receiving inappropriate ceftazidime/avibactam therapy.

Example 12

Multi-Center Evaluation of BD Phoenix™ CPO Detect Test in the BD Phoenix™ Automated Microbiology System for the Detection and Classification of Carbapenemase Producing Organisms in Clinical Isolates The purpose of this study was to evaluate the performance of the BD Phoenix™ CPO Detect test (CPO Detect) (BD Life Sciences, Sparks Md.), a growth based carbapenemase screening assay described in Example 11, to detect and classify carbapenemase production by clinical isolates of Enterobacteriaceae, *Pseudomonas aeruginosa*, and *Acinetobacter baumannii*.

A total of 1034 fresh and frozen isolates, including 722 Enterobacteriaceae and 312 non-fermenters (*Pseudomonas aeruginosa* and *Acinetobacter baumannii*), were evaluated across 3 clinical sites for carbapenemase production by the BD Phoenix™ CPO Detect test. Isolates were evaluated in parallel by the modified Carbapenemase Inactivation Method (mCIM) and meropenem and ertapenem MIC as reference methods. Carbapenemase Ambler classification (Class A, B, or D) was determined by multiplex PCR, performed by BD. Positive and negative percent agreements (PPA and NPA, respectively) between results of the CPO Detect and reference methods were determined. Discordant results were repeated in duplicate in the BD Phoenix System and appropriate reference methods. Data are presented in Table 8.1 (for Enterobacteriaceae), Table 8.2 (for non-fermenters) and Table 8.3 (Enterobacteriaceae and non-fermenters combined).

TABLE 8.1

Data for Enterobacteriaceae

| | | Reference System Result | | | | |
|---|---|---|---|---|---|---|
| | | Positive Class A | Positive Class B | Positive Class D | Positive Class Unk. | Negative |
| Phoenix System Result | Positive Class A | 93 | 0 | 0 | 3 | 0 |
| | Positive Class B | 2 | 82 | 1 | 0 | 5 |
| | Positive Class D | 0 | 2 | 97 | 2 | 1 |
| | Positive Class Unk. | 11 | 24 | 3 | 0 | 10 |
| | Negative | 2 | 0 | 0 | 0 | 384 |

TABLE 8.2

Data for non-fermenters

| | | Reference System Result | | | | |
|---|---|---|---|---|---|---|
| | NFGNR | Positive Class A | Positive Class B | Positive Class D | Positive Class Unk. | Negative |
| Phoenix System Result | Positive Class A | 16 | 0 | 2 | 0 | 2 |
| | Positive Class B | 2 | 47 | 0 | 1 | 2 |

TABLE 8.2-continued

Data for non-fermenters

| NFGNR | | Reference System Result | | | | |
|---|---|---|---|---|---|---|
| | | Positive Class A | Positive Class B | Positive Class D | Positive Class Unk. | Negative |
| | Positive Class D | 0 | 0 | 41 | 5 | 3 |
| | Positive Class Unk. | 3 | 10 | 10 | 8 | 1 |
| | Negative | 0 | 6 | 0 | 0 | 153 |

TABLE 8.3

Combined data for Enterobacteriaceae and non-fermenters

| Enterics and NFGNR Combined | | Reference System Result | | | | |
|---|---|---|---|---|---|---|
| | | Positive Class A | Positive Class B | Positive Class D | Positive Class Unk. | Negative |
| Phoenix System Result | Positive Class A | 109 | 0 | 2 | 3 | 2 |
| | Positive Class B | 4 | 129 | 1 | 1 | 7 |
| | Positive Class D | 0 | 2 | 138 | 7 | 4 |
| | Positive Class Unk. | 14 | 34 | 13 | 8 | 11 |
| | Negative | 2 | 6 | 0 | 0 | 537 |

These results show that for Enterobacteriaceae there was 99.4% PPA (when reference system detects a carbapenemase, % Phoenix detects a carbapenemase), 96.0% NPA (when reference system does not detect a carbapenemase, % Phoenix does not detect a carbapenemase) and 98.2% Classification Accuracy (when Phoenix and reference system are both positive and provide a classification, % Phoenix is correct). For non-fermenters, there was 96.0% PPA (when reference system detects a carbapenemase, % Phoenix detects a carbapenemase), 95.0% NPA (when reference system does not detect a carbapenemase, % Phoenix does not detect a carbapenemase) and 96.3% Classification Accuracy (when Phoenix and reference system are both positive and provide a classification, % Phoenix is correct). For the combined results, there was 98.3% PPA (when reference system detects a carbapenemase, % Phoenix detects a carbapenemase), 95.7% NPA (when reference system does not detect a carbapenemase, % Phoenix does not detect a carbapenemase) and 97.7% Classification Accuracy (when Phoenix and reference system are both positive and provide a classification, % Phoenix is correct).

Results are provided for 1034 compliant clinical isolates tested and analyzed for detection of carbapenemase by CPO Detect. After discrepant analysis, PPA and NPA in Enterobacteriaceae were 99.4% and 96.0%, respectively. Sixteen (2.2%) false positives and 2 false negatives (0.3%) were observed. For non-fermenters, PPA and NPA were 96.0% and 95.0%, respectively, with 8 false positive results (2.6%) and 6 false negative results (1.9%). Of the compliant isolates tested, 385 CPO Detect results were compared with multiplex PCR for carbapenemase classification. Overall class accuracy was 98.2% (272/277) for Enterobacteriaceae and 96.3% (104/108) for non-fermenters.

The BD Phoenix™ CPO Detect test, accessibly incorporated into the BD Phoenix automated AST test system, provides a novel and reliable method for the detection and classification of carbapenemases from Enterobacteriaceae, *P. aeruginosa*, and *A. baumannii*.

ABBREVIATIONS

CLOX Cloxacillin
EDTA Ethylene diamaine tetraacetic acid
DPA Dipicolinic acid
RPX Vaborbactam (RPX-7009)
AVI avibactam
BLI BLI (BLI-489, beta lactamase inhibitor)
DOR Doripenem
MEM Meropenem
TEM Temocillin
GAM Generalized Additive Model
ERT Ertapenem
IPM Imipenem Definitions As used herein, MIC refers to minimum inhibitory concentration.

As used herein, GAM refers to Generalized Additive Model, which is a transformation of instrument readings into a measurement of growth.

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting.

As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

It should be understood, however, that this detailed description, while indicating embodiments of the invention, is given by way of illustration only, since various changes and modifications within the spirit and scope of the invention will become apparent to those skilled in the art.

The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

What is claimed is:

1. A method for determining the presence of none, one or more Ambler class carbapenemases expressed by enteric bacteria, the method comprising:
   providing a sample comprising the enteric bacteria,
   applying the enteric bacteria in the test sample to a plurality of at least four test compositions for a duration of time, wherein each of the plurality of at least four test compositions comprises a growth medium and an antibiotic, and at least one of the at least four test compositions further comprises at least one carbapenemase inhibitor, and
   determining the presence of none, one or more Ambler class carbapenemases expressed by the enteric bacteria by detecting a presence or an inhibition of growth of the enteric bacteria in each of the plurality of at least four test compositions after the duration of time, wherein the method further comprises a determination selected from the following:
   a) determining the one or more Ambler class carbapenemases expressed by enteric bacteria is Class A by detecting:
      the inhibition of growth in a first test composition, wherein the antibiotic and inhibitor comprise a first concentration of temocillin (TEM), and a carbapenemase inhibitor of ambler class B,
      the presence of growth in a second test composition, wherein the antibiotic and inhibitors comprise a first concentration of doripenem (DOR), a carbapenemase inhibitor of ambler class C, and a carbapenemase inhibitor of ambler class B, and
      the inhibition of growth in a third test composition, wherein the antibiotic and inhibitors comprise a first concentration of meropenem (MEM), a carbapenemase inhibitor of ambler class C, and a carbapenemase inhibitor of ambler class A;
   b) determining the one or more Ambler class carbapenemases expressed by enteric bacteria is Class B by detecting:
      the inhibition of growth in a first test composition, wherein the antibiotic and inhibitors comprise a first concentration of TEM as the antibiotic and further comprising a carbapenemase inhibitor of ambler class B,
      the inhibition of growth in a second test composition, wherein the antibiotic and inhibitors comprise a first concentration of DOR, a carbapenemase inhibitor of ambler class C, and a carbapenemase inhibitor of ambler class B, and
      the presence of growth in a fourth test composition, wherein the antibiotic comprises a second concentration of DOR;
   c) determining the one or more Ambler class carbapenemases expressed by enteric bacteria is Class D by detecting:
      the inhibition of growth in a first test composition, wherein the antibiotic and inhibitor comprise a first concentration of TEM, and a carbapenemase inhibitor of ambler class B,
      the inhibition of growth in a second test composition, wherein the antibiotic and inhibitors comprise a first concentration of DOR, a carbapenemase inhibitor of ambler class C, and a carbapenemase inhibitor of ambler class B, and
      the inhibition of growth in a fourth test composition, wherein the antibiotic comprises a second concentration of DOR;
   d) determining the presence of one or more Ambler class carbapenemases expressed by enteric bacteria, wherein the Ambler class is not identified, by detecting:
      the inhibition of growth in a first test composition, wherein the antibiotic and inhibitor comprise a first concentration of TEM, and a carbapenemase inhibitor of ambler class B,
      the presence of growth in a second test composition, wherein the antibiotic and inhibitors comprise a first concentration of DOR, a carbapenemase inhibitor of ambler class C, and a carbapenemase inhibitor of ambler class B, and
      the presence of growth in a third test composition of the plurality of at least four test compositions, wherein the antibiotic and inhibitors comprise a first concentration of MEM as the antibiotic and further comprising a carbapenemase inhibitor of ambler class C and a carbapenemase inhibitor of ambler class A;
   e) determining the presence of one or more Ambler class A, B or D carbapenemases expressed by enteric bacteria by detecting:
      the inhibition of growth in a first test composition, wherein the antibiotic and inhibitor comprise a first concentration of TEM, a carbapenemase inhibitor of ambler class B,
      the presence of growth in a second test composition, wherein the antibiotic and inhibitors comprise a first concentration of DOR, a carbapenemase inhibitor of ambler class C, and a carbapenemase inhibitor of ambler class B, and
      the presence of growth in a third test composition, wherein the antibiotic and inhibitors comprise a first concentration of MEM, a carbapenemase inhibitor of ambler class C, and a carbapenemase inhibitor of ambler class A;
   f) determining that no answer is obtained regarding identifying the one or more Ambler class carbapenemases expressed by enteric bacteria by detecting:
      the inhibition of growth in a first test composition, wherein the antibiotic and inhibitor comprise a first concentration of TEM, and a carbapenemase inhibitor of ambler class B,
      the presence of growth in a second test composition, wherein the antibiotic and inhibitors comprise a first concentration of DOR, a carbapenemase inhibitor of ambler class C, and a carbapenemase inhibitor of ambler class B, the presence of growth in a third test composition of the plurality of at least four test compositions wherein the antibiotic and inhibitors comprise a first concentration of MEM, a carbapenemase inhibitor of ambler class C, and a carbapenemase inhibitor of ambler class A, and the inhibition of growth in a fifth test composition, wherein the antibiotic and inhibitor comprise a third concentration of MEM, and a carbapenemase inhibitor of ambler class C; or g) determining the presence of one or more Ambler class A, B or D carbapenemases expressed by enteric bacteria by detecting:

the inhibition of growth in a first test composition, wherein the antibiotic and inhibitor comprise a first concentration of TEM, and a carbapenemase inhibitor of ambler class B, the presence of growth in a second test composition, wherein the antibiotic and inhibitors comprise a first concentration of DOR, a carbapenemase inhibitor of ambler class C, and a carbapenemase inhibitor of ambler class B, the presence of growth in a third test composition, wherein the antibiotic and inhibitors comprise a first concentration of MEM, a carbapenemase inhibitor of ambler class C, and a carbapenemase inhibitor of ambler class A, and the presence of growth in a fifth test composition, wherein the antibiotic and inhibitor comprise the third concentration of MEM, and a carbapenemase inhibitor of ambler class C.

2. The method of claim 1, comprising determining the one or more Ambler class carbapenemases expressed by enteric bacteria is Class A by detecting:

the inhibition of growth in a first test composition, wherein the antibiotic and inhibitor comprise a first concentration of TEM, and a carbapenemase inhibitor of ambler class B, the presence of growth in a second test composition, wherein the antibiotic and inhibitors comprise a first concentration of DOR, a carbapenemase inhibitor of ambler class C, and a carbapenemase inhibitor of ambler class B, and the inhibition of growth in a third test composition, wherein the antibiotic and inhibitors comprise a first concentration of MEM, a carbapenemase inhibitor of ambler class C, and a carbapenemase inhibitor of ambler class A.

3. The method of claim 1, comprising determining the one or more Ambler class carbapenemases expressed by enteric bacteria is Class B by detecting:

the inhibition of growth in a first test composition, wherein the antibiotic and inhibitors comprise a first concentration of TEM as the antibiotic and further comprising a carbapenemase inhibitor of ambler class B, the inhibition of growth in a second test composition, wherein the antibiotic and inhibitors comprise a first concentration of DOR, a carbapenemase inhibitor of ambler class C, and a carbapenemase inhibitor of ambler class B, and the presence of growth in a fourth test composition, wherein the antibiotic comprises a second concentration of DOR.

4. The method of claim 1, comprising determining the one or more Ambler class carbapenemases expressed by enteric bacteria is Class D by detecting:

the inhibition of growth in a first test composition, wherein the antibiotic and inhibitor comprise a first concentration of TEM, and a carbapenemase inhibitor of ambler class B, the inhibition of growth in a second test composition, wherein the antibiotic and inhibitors comprise a first concentration of DOR, a carbapenemase inhibitor of ambler class C, and a carbapenemase inhibitor of ambler class B, and the inhibition of growth in a fourth test composition, wherein the antibiotic comprises a second concentration of DOR.

5. The method of claim 1, comprising determining the presence of one or more Ambler class carbapenemases expressed by enteric bacteria, wherein the Ambler class is not identified, by detecting:

the inhibition of growth in a first test composition, wherein the antibiotic and inhibitor comprise a first concentration of TEM, and a carbapenemase inhibitor of ambler class B, the presence of growth in a second test composition, wherein the antibiotic and inhibitors comprise a first concentration of DOR, a carbapenemase inhibitor of ambler class C, and a carbapenemase inhibitor of ambler class B, and the presence of growth in a third test composition of the plurality of at least four test compositions, wherein the antibiotic and inhibitors comprise a first concentration of MEM as the antibiotic and further comprising a carbapenemase inhibitor of ambler class C and a carbapenemase inhibitor of ambler class A.

6. The method of claim 1, comprising determining the presence of one or more Ambler class A, B or D carbapenemases expressed by enteric bacteria by detecting:

the inhibition of growth in a first test composition, wherein the antibiotic and inhibitor comprise a first concentration of TEM, a carbapenemase inhibitor of ambler class B, the presence of growth in a second test composition, wherein the antibiotic and inhibitors comprise a first concentration of DOR, a carbapenemase inhibitor of ambler class C, and a carbapenemase inhibitor of ambler class B, and the presence of growth in a third test composition, wherein the antibiotic and inhibitors comprise a first concentration of MEM, a carbapenemase inhibitor of ambler class C, and a carbapenemase inhibitor of ambler class A.

7. The method of claim 1, comprising determining that no answer is obtained regarding identifying the one or more Ambler class carbapenemases expressed by enteric bacteria by detecting:

the inhibition of growth in a first test composition, wherein the antibiotic and inhibitor comprise a first concentration of TEM, and a carbapenemase inhibitor of ambler class B, the presence of growth in a second test composition, wherein the antibiotic and inhibitors comprise a first concentration of DOR, a carbapenemase inhibitor of ambler class C, and a carbapenemase inhibitor of ambler class B, the presence of growth in a third test composition of the plurality of at least four test compositions wherein the antibiotic and inhibitors comprise a first concentration of MEM, a carbapenemase inhibitor of ambler class C, and a carbapenemase inhibitor of ambler class A, and the inhibition of growth in a fifth test composition, wherein the antibiotic and inhibitor comprise a third concentration of MEM, and a carbapenemase inhibitor of ambler class C.

8. The method of claim 1, comprising determining the presence of one or more Ambler class A, B or D carbapenemases expressed by enteric bacteria by detecting:

the inhibition of growth in a first test composition, wherein the antibiotic and inhibitor comprise a first concentration of TEM, and a carbapenemase inhibitor of ambler class B, the presence of growth in a second test composition, wherein the antibiotic and inhibitors comprise a first concentration of DOR, a carbapenemase inhibitor of ambler class C, and a carbapenemase inhibitor of ambler class B, the presence of growth in a third test composition, wherein the antibiotic and inhibitors comprise a first concentration of MEM, a carbapenemase inhibitor of ambler class C, and a carbapenemase inhibitor of ambler class A, and the presence of growth in a fifth test composition, wherein the antibiotic and inhibitor comprise the third concentration of MEM, and a carbapenemase inhibitor of ambler class C.

9. The method of claim 1, the method further comprising a method for identifying none, one or more Ambler class carbapenemases expressed by non-fermenting bacteria, the method comprising:

providing a sample comprising the non-fermenting bacteria, applying the non-fermenting bacteria in the test sample to a composition for a duration of time, wherein the test composition comprises a growth medium and an antibiotic and a carbapenemase inhibitor, and determining the presence of none, one or more Ambler class carbapenemases expressed by non-fermenting bacteria by detecting a presence or an inhibition of growth of the non-fermenting bacteria in the test compositions after the duration of time.

10. The method of claim 1, the method further comprising a method for determining the presence of none, one, or more Ambler class carbapenemases expressed by non-fermenting bacteria, the method comprising:

providing a sample comprising the non-fermenting bacteria, applying the non-fermenting bacteria in the test sample to a plurality of at least three test compositions for a duration of time, wherein each of the plurality of at least three test compositions comprises a growth medium and an antibiotic, and at least one of the at least three test compositions further comprises at least one carbapenemase inhibitor, and determining the presence of none, one, or more one or more Ambler class carbapenemases expressed by the non-fermenting bacteria by detecting a presence or an inhibition of growth of the non-fermenting bacteria in each of the plurality of at least three test compositions after the duration of time.

11. The method of claim 1, wherein the carbapenemase inhibitor is an ambler class D carbapenemase inhibitor selected from the group consisting of avibactam (AVI), Clavulanic acid, boronic acid, tazobactam, sulbactam, vaborbactam (RPX-7009) and BLI-489.

12. The method of claim 1, wherein the carbapenemase inhibitor is an ambler class B carbapenemase inhibitor selected from the group consisting of ethylenediaminetetraacetic acid (EDTA), dipicolinic acid (DPA) and deferoxamine.

13. The method of claim 1, wherein the carbapenemase inhibitor is an ambler class C carbapenemase inhibitor selected from the group consisting of cloxacillin (CLOX), dicloxacillin and flucloxacillin.

14. The method of claim 1, wherein the carbapenemase inhibitor is an ambler class A carbapenemase inhibitor selected from the group consisting of vaborbactam (RPX-7009), AVI, Clavulanic acid, boronic acid, tazobactam, sulbactam, and BLI-489.

* * * * *